(12) United States Patent
Pervan et al.

(10) Patent No.: US 11,878,324 B2
(45) Date of Patent: Jan. 23, 2024

(54) DIGITAL THERMAL BINDER AND POWDER PRINTING

(71) Applicant: Ceraloc Innovation AB, Viken (SE)

(72) Inventors: Darko Pervan, Viken (SE); Tony Pervan, Stockholm (SE)

(73) Assignee: Ceraloc Innovation AB, Viken (SE)

(*) Notice: Subject to any disclaimer, the term of this patent is extended or adjusted under 35 U.S.C. 154(b) by 178 days.

(21) Appl. No.: 17/673,445

(22) Filed: Feb. 16, 2022

(65) Prior Publication Data

US 2022/0274131 A1 Sep. 1, 2022

Related U.S. Application Data

(63) Continuation of application No. 16/946,312, filed on Jun. 16, 2020, now Pat. No. 11,285,508, which is a
(Continued)

(51) Int. Cl.
*B41J 3/407* (2006.01)
*B05D 1/12* (2006.01)
(Continued)

(52) U.S. Cl.
CPC ............ *B05D 1/12* (2013.01); *B05D 1/02* (2013.01); *B05D 1/36* (2013.01); *B05D 3/002* (2013.01); *B05D 3/065* (2013.01); *B05D 3/067* (2013.01); *B05D 3/12* (2013.01); *B05D 5/06* (2013.01); *B05D 7/50* (2013.01); *B05D 7/52* (2013.01); *B05D 7/53* (2013.01); *B32B 3/06* (2013.01); *B32B 3/30* (2013.01); *B32B 21/02* (2013.01); *B32B 29/002* (2013.01); *B41F 17/00* (2013.01); *B41F 19/002* (2013.01); *B41F 19/02* (2013.01); *B41J 2/01* (2013.01); *B41J 2/14088* (2013.01); *B41J 2/32* (2013.01); *B41J 2/325* (2013.01); *B41J 3/28* (2013.01); *B41J 3/407* (2013.01);
(Continued)

(58) Field of Classification Search
None
See application file for complete search history.

(56) References Cited

U.S. PATENT DOCUMENTS 3,083,116 A 3/1963 Berndt
3,397,496 A 8/1968 Sohns
(Continued)

FOREIGN PATENT DOCUMENTS

CN 1795107 A * 6/2006 .............. B41M 5/52
DE 10 2007 015 907 A1 10/2008
(Continued)

OTHER PUBLICATIONS

Jonckheree, Machine TranslationofCN-1795107-A, 2006 (Year: 2006).*
(Continued)

*Primary Examiner* — Scott A Richmond
(74) *Attorney, Agent, or Firm* — Boone IP Law

(57) ABSTRACT

A method of forming a digital print on a surface by applying powder of dry ink including colourants on the surface, bonding a part of the dry ink powder to the surface by a digital heating print head such that the digital print is formed by the bonded dry ink colourants and removing non-bonded dry ink from the surface.

19 Claims, 15 Drawing Sheets

Related U.S. Application Data continuation of application No. 16/787,771, filed on Feb. 11, 2020, now Pat. No. 10,723,147, which is a continuation of application No. 16/225,065, filed on Dec. 19, 2018, now Pat. No. 10,596,837, which is a continuation of application No. 15/840,056, filed on Dec. 13, 2017, now Pat. No. 10,189,281, which is a continuation of application No. 15/585,482, filed on May 3, 2017, now abandoned, which is a continuation of application No. 15/150,471, filed on May 10, 2016, now abandoned, which is a continuation of application No. 14/152,356, filed on Jan. 10, 2014, now Pat. No. 9,371,456.

(60) Provisional application No. 61/751,418, filed on Jan. 11, 2013.

(51) Int. Cl.

| | | |
|---|---|---|
| *C09D 7/40* | (2018.01) | |
| *B05D 1/02* | (2006.01) | |
| *B05D 1/36* | (2006.01) | |
| *B05D 3/00* | (2006.01) | |
| *B05D 3/06* | (2006.01) | |
| *B05D 3/12* | (2006.01) | |
| *B05D 5/06* | (2006.01) | |
| *B05D 7/00* | (2006.01) | |
| *B32B 3/06* | (2006.01) | |
| *B32B 3/30* | (2006.01) | |
| *B32B 21/02* | (2006.01) | |
| *B32B 29/00* | (2006.01) | |
| *B41F 17/00* | (2006.01) | |
| *B41F 19/00* | (2006.01) | |
| *B41F 19/02* | (2006.01) | |
| *B41J 2/01* | (2006.01) | |
| *B41J 2/14* | (2006.01) | |
| *B41J 2/32* | (2006.01) | |
| *B41J 2/325* | (2006.01) | |
| *B41J 3/28* | (2006.01) | |
| *B41J 3/54* | (2006.01) | |
| *B41J 11/00* | (2006.01) | |
| *B41M 1/38* | (2006.01) | |
| *B41M 3/00* | (2006.01) | |
| *B41M 5/00* | (2006.01) | |
| *B41M 5/50* | (2006.01) | |
| *B44C 1/24* | (2006.01) | |
| *B44C 5/04* | (2006.01) | |
| *C08K 3/22* | (2006.01) | |
| *C09D 11/02* | (2014.01) | |
| *C09D 11/037* | (2014.01) | |
| *C09D 11/103* | (2014.01) | |
| *C09D 161/28* | (2006.01) | |
| *C09D 197/02* | (2006.01) | |
| *E04F 15/02* | (2006.01) | |
| *B05D 5/02* | (2006.01) | |
| *B05D 7/06* | (2006.01) | |
| *B32B 27/14* | (2006.01) | |
| *B41J 2/005* | (2006.01) | |
| *B41M 1/22* | (2006.01) | |

(52) U.S. Cl.
CPC .............. *B41J 3/54* (2013.01); *B41J 11/002* (2013.01); *B41J 11/0015* (2013.01); *B41M 1/38* (2013.01); *B41M 3/00* (2013.01); *B41M 5/00* (2013.01); *B41M 5/0017* (2013.01); *B41M 5/0023* (2013.01); *B41M 5/0029* (2013.01); *B41M 5/50* (2013.01); *B41M 5/502* (2013.01); *B41M 5/506* (2013.01); *B44C 1/24* (2013.01); *B44C 5/04* (2013.01); *C08K 3/22* (2013.01); *C09D 7/69* (2018.01); *C09D 11/02* (2013.01); *C09D 11/037* (2013.01); *C09D 11/103* (2013.01); *C09D 161/28* (2013.01); *C09D 197/02* (2013.01); *E04F 15/02* (2013.01); *B05D 5/02* (2013.01); *B05D 7/06* (2013.01); *B05D 2401/32* (2013.01); *B32B 27/14* (2013.01); *B32B 2255/12* (2013.01); *B32B 2262/067* (2013.01); *B32B 2307/4023* (2013.01); *B32B 2607/00* (2013.01); *B41F 19/007* (2013.01); *B41J 2/005* (2013.01); *B41M 1/22* (2013.01); *B41M 5/0041* (2013.01); *B41M 5/0076* (2013.01); *C08K 2003/2227* (2013.01); *Y10T 428/24066* (2015.01); *Y10T 428/24901* (2015.01)

(56) References Cited

U.S. PATENT DOCUMENTS

| | | | |
|---|---|---|---|
| 3,440,076 | A | 4/1969 | Vaurio |
| 3,446,184 | A | 5/1969 | Johnson |
| 3,545,997 | A | 12/1970 | Hochberg |
| 3,634,975 | A | 1/1972 | Hensley |
| 3,648,358 | A | 3/1972 | Cannady et al. |
| 3,880,687 | A | 4/1975 | Elmendorf et al. |
| 3,911,160 | A | 10/1975 | Neuberg |
| 4,050,409 | A | 9/1977 | Duchenaud et al. |
| 4,227,200 | A | 10/1980 | Mansukhani |
| 4,233,387 | A | 11/1980 | Mammino et al. |
| 4,312,268 | A | 1/1982 | King et al. |
| 4,467,007 | A | 8/1984 | Elgie |
| 4,504,523 | A | 3/1985 | Miller et al. |
| 4,689,259 | A | 8/1987 | Miller et al. |
| 4,796,402 | A | 1/1989 | Pajala |
| 4,833,530 | A | 5/1989 | Kohashi |
| 4,880,689 | A | 11/1989 | Park et al. |
| 4,943,816 | A | 7/1990 | Sporer |
| 5,204,055 | A | 4/1993 | Sachs |
| 5,380,392 | A | 1/1995 | Imamura et al. |
| 5,498,466 | A | 3/1996 | Navarro |
| 5,594,484 | A | 1/1997 | Furukawa |
| 5,597,434 | A | 1/1997 | Kukoff |
| 5,627,578 | A | 5/1997 | Weintraub |
| 5,718,753 | A | 2/1998 | Suzuki et al. |
| 5,778,789 | A | 7/1998 | Krishnan et al. |
| 6,094,882 | A | 8/2000 | Pervan |
| 6,200,410 | B1 | 3/2001 | Kukoff |
| 6,387,457 | B1 | 5/2002 | Jiang et al. |
| 6,394,595 | B1 | 5/2002 | Jiang et al. |
| 6,402,317 | B2 | 6/2002 | Yanagawa et al. |
| 6,422,696 | B1 | 7/2002 | Takahashi et al. |
| 6,439,713 | B1 | 8/2002 | Noguchi et al. |
| 6,488,994 | B1 | 12/2002 | Haller et al. |
| 6,579,616 | B1 | 6/2003 | Beckman |
| 6,773,799 | B1 | 8/2004 | Persson et al. |
| 7,311,802 | B2 * | 12/2007 | Gane .................... C09B 63/005 162/137 |
| 7,383,768 | B2 | 6/2008 | Reichwein et al. |
| 7,632,561 | B2 | 12/2009 | Thiers |
| 7,721,503 | B2 | 5/2010 | Pervan |
| 7,908,815 | B2 | 3/2011 | Pervan |
| 8,114,513 | B2 | 2/2012 | Rentschler |
| 8,337,947 | B2 | 12/2012 | Camorani |
| 8,353,140 | B2 | 1/2013 | Pervan |
| 8,371,456 | B2 | 2/2013 | Scadden |
| 8,464,489 | B2 | 6/2013 | Pervan |
| 8,465,804 | B2 | 6/2013 | Provoost et al. |
| 8,544,230 | B2 | 10/2013 | Pervan |
| 8,621,814 | B2 | 1/2014 | Cappelle |
| 8,763,341 | B2 | 7/2014 | Pervan |
| 8,808,556 | B2 | 8/2014 | Kukoff |
| 9,079,212 | B2 | 7/2015 | Pervan et al. |
| 9,140,010 | B2 | 9/2015 | Pervan |

(56) References Cited

U.S. PATENT DOCUMENTS

| | | |
|---|---|---|
| 9,279,058 B2 | 3/2016 | Pervan et al. |
| 9,321,925 B2 | 4/2016 | Pervan et al. |
| 9,346,303 B2 | 5/2016 | Grinberg |
| 9,371,456 B2 | 6/2016 | Pervan et al. |
| 9,446,602 B2 | 9/2016 | Pervan |
| 9,528,011 B2 | 12/2016 | Pervan et al. |
| 9,630,404 B2 | 4/2017 | Pervan et al. |
| 9,670,371 B2 | 6/2017 | Pervan et al. |
| 9,738,095 B2 | 8/2017 | Pervan et al. |
| 9,873,803 B2 | 1/2018 | Pervan et al. |
| 10,016,988 B2 | 7/2018 | Pervan et al. |
| 10,029,484 B2 | 7/2018 | Pervan et al. |
| 10,035,358 B2 | 7/2018 | Pervan et al. |
| 10,041,212 B2 | 8/2018 | Pervan |
| 10,189,281 B2 | 1/2019 | Pervan et al. |
| 10,239,346 B2 | 3/2019 | Vermeulen |
| 10,369,814 B2 | 8/2019 | Pervan et al. |
| 10,384,471 B2 | 8/2019 | Pervan |
| 10,414,173 B2 | 9/2019 | Pervan |
| 10,556,447 B2 | 2/2020 | Pervan |
| 10,596,837 B2 | 3/2020 | Pervan et al. |
| 10,723,147 B2 | 7/2020 | Pervan et al. |
| 10,800,186 B2 | 10/2020 | Pervan et al. |
| 10,988,901 B2 | 4/2021 | Pervan |
| 11,014,378 B2 | 5/2021 | Pervan et al. |
| 11,065,889 B2 | 7/2021 | Pervan |
| 11,130,352 B2 | 9/2021 | Pervan et al. |
| 11,285,508 B2 | 3/2022 | Pervan et al. |
| 2001/0005542 A1 | 6/2001 | Graab et al. |
| 2001/0022607 A1 | 9/2001 | Takahashi et al. |
| 2002/0149137 A1 | 10/2002 | Jang et al. |
| 2003/0108718 A1 | 6/2003 | Simon et al. |
| 2003/0138618 A1 | 7/2003 | Courtoy |
| 2003/0173695 A1 | 9/2003 | Monkhouse |
| 2003/0207083 A1 | 11/2003 | Hansson |
| 2004/0101619 A1 | 5/2004 | Camorani |
| 2004/0142107 A1 | 7/2004 | Eriksson et al. |
| 2004/0153204 A1 | 8/2004 | Blanco |
| 2004/0170912 A1 | 9/2004 | Brennan |
| 2004/0177788 A1 | 9/2004 | Rick et al. |
| 2004/0180181 A1 | 9/2004 | Franzoi et al. |
| 2004/0180980 A1 | 9/2004 | Petter et al. |
| 2004/0217186 A1 | 11/2004 | Sachs |
| 2005/0093194 A1 | 5/2005 | Oriakhi |
| 2005/0128274 A1 | 6/2005 | Matsushima |
| 2005/0176321 A1 | 8/2005 | Crette et al. |
| 2005/0229353 A1 | 10/2005 | Azmoun et al. |
| 2005/0249923 A1 | 11/2005 | Reichwein et al. |
| 2006/0144004 A1 | 7/2006 | Nollet |
| 2006/0179773 A1 | 8/2006 | Pervan |
| 2006/0188670 A1 | 8/2006 | Kojima |
| 2006/0192180 A1 | 8/2006 | Ichitani |
| 2006/0246266 A1 | 11/2006 | Hall |
| 2006/0276367 A1 | 12/2006 | Shah et al. |
| 2007/0049047 A1 | 3/2007 | Fujimoto |
| 2007/0091160 A1 | 4/2007 | Kis |
| 2007/0107344 A1 | 5/2007 | Kornfalt |
| 2007/0193174 A1 | 8/2007 | Vogel et al. |
| 2007/0224438 A1 | 9/2007 | Van Benthem et al. |
| 2007/0231583 A1* | 10/2007 | Ilzuka .................... B32B 27/10 428/411.1 |
| 2007/0240585 A1 | 10/2007 | Vaish et al. |
| 2007/0283648 A1 | 12/2007 | Chen |
| 2007/0299196 A1 | 12/2007 | Ohkoshi et al. |
| 2008/0010924 A1 | 1/2008 | Pietruczynik et al. |
| 2008/0075859 A1 | 3/2008 | Baker et al. |
| 2008/0098659 A1 | 5/2008 | Sung |
| 2008/0185092 A1 | 8/2008 | Blenkhorn |
| 2008/0241472 A1 | 10/2008 | Shiao et al. |
| 2008/0261003 A1 | 10/2008 | Lewis et al. |
| 2008/0292885 A1 | 11/2008 | Dohring |
| 2009/0010682 A1 | 1/2009 | Camorani |
| 2009/0031662 A1 | 2/2009 | Chen et al. |
| 2009/0047480 A1 | 2/2009 | Juers et al. |
| 2009/0116966 A1 | 5/2009 | Althoff et al. |
| 2009/0151866 A1 | 6/2009 | Endert |
| 2009/0155612 A1 | 6/2009 | Pervan et al. |
| 2009/0252925 A1 | 10/2009 | Provoost |
| 2010/0009282 A1 | 1/2010 | Katoh et al. |
| 2010/0046010 A1 | 2/2010 | Bauer |
| 2010/0092731 A1 | 4/2010 | Pervan et al. |
| 2010/0134895 A1 | 6/2010 | Hoffman et al. |
| 2010/0166997 A1 | 7/2010 | Chisaka et al. |
| 2010/0192793 A1 | 8/2010 | Verhaeghe |
| 2010/0196678 A1 | 8/2010 | Vermeulen |
| 2010/0300020 A1 | 12/2010 | Vermeulen |
| 2010/0300030 A1 | 12/2010 | Pervan et al. |
| 2010/0307677 A1 | 12/2010 | Buhlmann |
| 2010/0323187 A1 | 12/2010 | Kalwa |
| 2011/0024938 A1 | 2/2011 | Tripp et al. |
| 2011/0038826 A1 | 2/2011 | Kimball et al. |
| 2011/0129640 A1 | 6/2011 | Beall |
| 2011/0171412 A1 | 7/2011 | Döhring |
| 2011/0176901 A1 | 7/2011 | Chait et al. |
| 2011/0177354 A1 | 7/2011 | Ziegler et al. |
| 2011/0189448 A1 | 8/2011 | Lindgren et al. |
| 2011/0189471 A1 | 8/2011 | Ziegler et al. |
| 2011/0190904 A1 | 8/2011 | Lechmann et al. |
| 2011/0237739 A1 | 9/2011 | Tada |
| 2011/0247748 A1 | 10/2011 | Pervan et al. |
| 2011/0250404 A1 | 10/2011 | Pervan et al. |
| 2011/0261464 A1 | 10/2011 | Hoffman et al. |
| 2011/0268937 A1 | 11/2011 | Schacht et al. |
| 2011/0293906 A1 | 12/2011 | Jacobsson |
| 2012/0176443 A1 | 7/2012 | Robertson et al. |
| 2012/0196081 A1 | 8/2012 | Gleich |
| 2012/0263878 A1 | 10/2012 | Ziegler et al. |
| 2012/0263965 A1 | 10/2012 | Persson et al. |
| 2012/0264853 A1 | 10/2012 | Ziegler et al. |
| 2012/0269983 A1 | 10/2012 | Grinberg |
| 2013/0043211 A1 | 2/2013 | Vermeulen |
| 2013/0108873 A1 | 5/2013 | Shiao et al. |
| 2013/0243460 A1 | 9/2013 | Makiura et al. |
| 2014/0017452 A1 | 1/2014 | Pervan et al. |
| 2014/0023832 A1 | 1/2014 | Pervan et al. |
| 2014/0028772 A1 | 1/2014 | Pervan |
| 2014/0196618 A1 | 7/2014 | Pervan et al. |
| 2014/0198168 A1 | 7/2014 | Pervan et al. |
| 2014/0198170 A1 | 7/2014 | Pervan et al. |
| 2014/0199495 A1 | 7/2014 | Pervan et al. |
| 2014/0199513 A1 | 7/2014 | Pervan et al. |
| 2014/0199531 A1 | 7/2014 | Pervan et al. |
| 2014/0220318 A1 | 8/2014 | Pervan |
| 2015/0030817 A1 | 1/2015 | Wiegelmann |
| 2015/0274997 A1 | 10/2015 | Pervan et al. |
| 2015/0298492 A1 | 10/2015 | Palumbo |
| 2016/0144612 A1 | 5/2016 | Pervan et al. |
| 2016/0208116 A1 | 7/2016 | Pervan et al. |
| 2016/0250853 A1 | 9/2016 | Pervan et al. |
| 2016/0325559 A1 | 11/2016 | Pervan et al. |
| 2016/0368280 A1 | 12/2016 | Pervan |
| 2017/0066255 A1 | 3/2017 | Pervan et al. |
| 2017/0204281 A1 | 7/2017 | Pervan et al. |
| 2017/0232761 A1 | 8/2017 | Pervan et al. |
| 2017/0348984 A1 | 12/2017 | Pervan et al. |
| 2018/0111390 A1 | 4/2018 | Pervan et al. |
| 2018/0127605 A1 | 5/2018 | Pervan et al. |
| 2018/0178553 A1 | 6/2018 | Pervan |
| 2018/0298216 A1 | 10/2018 | Pervan et al. |
| 2018/0320321 A1 | 11/2018 | Pervan |
| 2019/0119513 A1 | 4/2019 | Pervan et al. |
| 2019/0284819 A1 | 9/2019 | Pervan et al. |
| 2019/0345348 A1 | 11/2019 | Pervan et al. |
| 2019/0351685 A1 | 11/2019 | Pervan |
| 2020/0079114 A1 | 3/2020 | Pervan et al. |
| 2020/0139726 A1 | 5/2020 | Pervan et al. |
| 2020/0171849 A1 | 6/2020 | Pervan et al. |
| 2021/0001647 A1 | 1/2021 | Pervan |
| 2021/0070065 A1 | 3/2021 | Pervan |

(56) References Cited

U.S. PATENT DOCUMENTS

| | | |
|---|---|---|
| 2021/0214898 A1 | 7/2021 | Pervan |
| 2021/0379907 A1 | 12/2021 | Pervan et al. |

FOREIGN PATENT DOCUMENTS

| | | |
|---|---|---|
| DE | 10 2010 036 454 A1 | 1/2012 |
| EP | 0 403 264 A2 | 12/1990 |
| EP | 0 657 309 A1 | 6/1995 |
| EP | 0 769 535 A2 | 4/1997 |
| EP | 0 769 535 A3 | 9/1997 |
| EP | 1 020 303 A1 | 7/2000 |
| EP | 1 020 765 A1 | 7/2000 |
| EP | 1 209 199 A1 | 5/2002 |
| EP | 1 584 378 A1 | 10/2005 |
| EP | 1 961 556 A1 | 8/2008 |
| EP | 2 106 903 A1 | 10/2009 |
| EP | 2 108 524 A1 | 10/2009 |
| EP | 2 213 476 A1 | 8/2010 |
| EP | 2 264 259 A2 | 12/2010 |
| EP | 2 363 299 A1 | 9/2011 |
| GB | 1 215 551 A | 12/1970 |
| GB | 1 344 197 A | 1/1974 |
| GB | 2 065 556 A | 7/1981 |
| GB | 2 128 898 A | 5/1984 |
| GB | 2 419 110 A | 4/2006 |
| GB | 2 452 545 A | 3/2009 |
| JP | S51-128409 A | 11/1976 |
| JP | H05-320541 A | 12/1993 |
| JP | H06-183128 A | 7/1994 |
| JP | H06-287467 A | 10/1994 |
| JP | H09-216351 A | 8/1997 |
| JP | H09-216453 A | 8/1997 |
| JP | H10-095165 A | 4/1998 |
| JP | 2000-158796 A | 6/2000 |
| JP | 2001-311254 A | 11/2001 |
| JP | 2005-097339 A | 4/2005 |
| JP | 2006-036559 A | 2/2006 |
| JP | 2006-167651 A | 6/2006 |
| JP | 2008-156573 A | 7/2008 |
| JP | 2008-265229 A | 11/2008 |
| JP | 2009-173003 A | 8/2009 |
| JP | 2010-209325 A | 9/2010 |
| JP | 2011-522138 A | 7/2011 |
| KR | 2009-0112326 A | 10/2009 |
| WO | WO 99/65699 A1 | 12/1999 |
| WO | WO 01/47724 A1 | 7/2001 |
| WO | WO 02/42373 A1 | 5/2002 |
| WO | WO 2005/120847 A1 | 12/2005 |
| WO | WO 2006/125036 A2 | 11/2006 |
| WO | WO 2007/033031 A2 | 3/2007 |
| WO | WO 2007/060298 A1 | 5/2007 |
| WO | WO 2008/042088 A1 | 4/2008 |
| WO | WO 2008/121749 A1 | 10/2008 |
| WO | WO 2009/030935 A2 | 3/2009 |
| WO | WO 2009/124704 A1 | 10/2009 |
| WO | WO 2010/070485 A2 | 6/2010 |
| WO | WO 2011/064075 A2 | 6/2011 |
| WO | WO 2011/129757 A1 | 10/2011 |
| WO | WO 2012/078533 A1 | 6/2012 |
| WO | WO 2012/141651 A1 | 10/2012 |
| WO | WO 2014/014400 A1 | 1/2014 |
| WO | WO 2014/014400 A9 | 1/2014 |
| WO | WO 2014/037823 A1 | 3/2014 |
| WO | WO 2014/109703 A1 | 7/2014 |

OTHER PUBLICATIONS

U.S. Appl. No. 15/845,828, Darko Pervan and Tony Pervan, filed Dec. 18, 2017, (Cited herein as US Patent Application Publication No. 2018/0127605 A1 of May 10, 2018).

U.S. Appl. No. 16/428,257, Darko Pervan and Tony Pervan, filed May 31, 2019, (Cited herein as US Patent Application Publication No. 2019/0284819 A1 of Sep. 19, 2019).

U.S. Appl. No. 16/733,493, Darko Pervan and Tony Pervan, filed Jan. 3, 2020, (Cited herein as US Patent Application Publication No. 2020/0139726 A1 of May 7, 2020).

U.S. Appl. No. 17/218,782, Darko Pervan, filed Mar. 31, 2021, (Cited herein as US Patent Application Publication No. 2021/0214898 A1 of Jul. 15, 2021).

U.S. Appl. No. 17/406,424, Darko Pervan and Tony Pervan, filed Aug. 19, 2021, (Cited herein as US Patent Application Publication No. 2021/0379907 A1 of Dec. 9, 2021).

International Search Report issued in PCT/SE2014/050023, dated Apr. 17, 2014, Patent-och registreringsverket, Stockholm, SE, 5 pages.

Extended European Search Report dated Aug. 1, 2016 in EP 14737710.5, European Patent Office, Munich, DE, 8 pages.

International Search Report issued in PCT/SE2014/050019, dated Apr. 17, 2014, Patent-och registreringsverket, Stockholm, SE, 6 pages.

Pervan, Darko, et al., Technical Disclosure entitled Digital Printing and Embossing, IP.com No. IPCOM000224950D, IP.com PriorArtDatabase, Jan. 15, 2013, 89 pages.

Pervan, Darko, Technical Disclosure entitled "Digital Overlay," IP.com No. IPCOM000225271D, IP.com PriorArtDatabase, Feb. 5, 2013, 24 pages.

Hudd, "Chapter 1: Inkjet Printing Technologies," *Chemistry of Inkjet Inks,* 2010, pp. 3-18, World Scientific Publishing Co. PTE. Ltd. , Published in Singapore and Hackensack, NJ.

Owens, James C., "A Tutorial on Printing", *Imaging.org—Resources,* 2010, pp. 1-5, Society for Imaging sciences and Technology, retrieved Jul. 27, 2015 and Dec. 27, 2018 from http://web.archive.org/web/20100706153535/http://www.imaging.org/ist/resources/tutorials/printing.cfm.

Odian, George, "Principles of Polymerization," 1991, Third Edition, 5 pages incl. pp. 122-123, John Wiley & Sons, Inc., New York, NY, USA.

Romano, Frank J., Digital Printing Pocket Primer Series "Mastering On-Demand and Variable Data Printing for Profit," Copyright 2000, 52 pages, Windsor Professional Information, L.L.C., San Diego, CA.

* cited by examiner

KNOWN TECHNOLOGY

DIGITAL THERMAL BINDER AND POWDER PRINTING

CROSS REFERENCE TO RELATED APPLICATIONS

The present application is a continuation of U.S. application Ser. No. 16/946,312, filed on Jun. 16, 2020, which is a continuation of U.S. application Ser. No. 16/787,771, filed on Feb. 11, 2020, now U.S. Pat. No. 10,723,147, which is a continuation of U.S. application Ser. No. 16/225,065, filed on Dec. 19, 2018, issued as U.S. Pat. No. 10,596,837, which is a continuation of U.S. application Ser. No. 15/840,056, filed Dec. 13, 2017, issued as U.S. Pat. No. 10,189,281, which is a continuation of Ser. No. 15/585,482, filed May 3, 2017, which is a continuation of U.S. application Ser. No. 15/150,571, filed May 10, 2016, issued as U.S. Pat. No. 9,670,371 on Jun. 6, 2017, which is a continuation of U.S. application Ser. No. 14/152,356, filed on Jan. 10, 2014, issued as U.S. Pat. No. 9,371,456 on Jun. 21, 2016, which claims the benefit of U.S. Provisional Application No. 61/751,418, filed on Jan. 11, 2013. The entire contents of each of U.S. application Ser. No. 16/946,312, U.S. application Ser. No. 16/787,771, U.S. application Ser. No. 16/225,065, U.S. application Ser. No. 15/840,056, U.S. application Ser. No. 15/585,482, U.S. application Ser. No. 15/150,571, U.S. application Ser. No. 14/152,356 and U.S. Provisional Application No. 61/751,418 are hereby incorporated herein by reference in their entirety.

TECHNICAL FIELD

The disclosure generally relates to the field of digitally created decorative surfaces for building panels such as floor and wall panels. The disclosure relates to a method to apply and bond powder based colourants on a surface such that a digital print is formed.

FIELD OF APPLICATION

Embodiments of the present invention are particularly suitable for use in floors, which are formed of floor panels comprising a core or a body, a decorative layer and preferably a transparent wear resistant structured layer above the decorative layer. Preferred embodiments are conventional laminate floors, powder based floor, wood floors, plastic based LVT floors and ceramic tiles. The following description of techniques, problems of known technology and objects and features of the invention will therefore, as a non-restrictive example, be aimed above all at this field of application and in particular at floorings which are similar to conventional laminated floorings or floorings with a resilient surface layer.

It should be emphasized that embodiments of the invention may be used to produce a digital image and/or a digitally formed structure on any surface but flat panels such as, for example, building panels in general, wall panels, ceilings, furniture components and similar products that generally have large surfaces with advanced decorative patterns are preferred. The basic principles of the invention may be used to apply a print on paper, foils, textiles, metals, solid wood, wood veneer, wood based sheet materials, cork, linoleum, polymer material, ceramics, wall paper and similar surfaces.

BACKGROUND

The following description is used to describe the background and products, materials and production methods that may comprise specific parts of preferred embodiments in the disclosure of this invention.

a) Laminate Floorings.

The majority of all laminate floors are produced according to a production method generally referred to as Direct Pressed Laminate (DPL). Such laminated floors have a core of 6-12 mm fibreboard, a 0.2 mm thick upper decorative surface layer of laminate and a 0.1-0.2 mm thick lower balancing layer of laminate, plastic, paper or like materials.

The surface layer of a laminate floor is characterized in that the decorative and wear properties are generally obtained with two separate layers of paper, one above the other. The decorative layer is generally a printed paper and the wear layer is a transparent overlay paper, which comprises small aluminium oxide particles.

The decor paper is the most critical of the lamination papers as it gives the visual appearance of the laminate. The decor paper weight is generally in the range of 60-150 $g/m^2$.

The overlay paper is generally thinner with a weight of about 20-50 $g/m^2$ and is made of pure cellulose, which is based on delignified pulp. The overlay paper becomes almost completely transparent after lamination and the appearance of the decor paper is visible. Thicker overlay papers with a considerable amount of aluminium oxide particles may give a high wear resistance. The disadvantage is that they are less transparent and the decorative pattern is covered by a grey layer that disturbs the printed pattern.

Printing of decorative papers is very cost efficient. Rotogravure presses with printing cylinders that may have a width of 3 metres and that may run with a speed of up to 600 m/min are used. The printing cylinders are generally produced by conventional mechanical engraving. Recently digital laser engraving has been introduced which allows faster décor development and provides a better décor quality. Solvent-free inks with organic pigments are often used and excess ink is re-cycled.

The printed decorative paper and the overlay are impregnated with melamine formaldehyde resins, generally referred to as melamine resins, and laminated to a HDF core in large discontinuous or continuous laminate presses where the resin cures under high heat (about 170° C.) and pressure (40-60 bars) and the papers are laminated to the core material. An embossed press plate or steal belt forms the surface structure. Sometimes a structured paper is used as a press matrix. The embossing is in high quality floors made in register with the design. The embossing depth is limited to 0.1-0.2 mm (100-200 micron).

Laminated floors may also be produced with direct printing technology. One advantage is that the pressing operation may be avoided and that no printed papers are needed to provide a decorative surface. Hydro printing inks are used to print the décor by a multicolour printing press with rollers onto a pre-sealed core and the print is covered with a protective transparent wear layer that may be an overlay, a plastic foil or a lacquer. The production process is rather complicated and is only cost efficient in very large production volumes.

Direct printing technology may be replaced with digital printing technology that is much more flexible and small production volumes can be economically manufactured. The difference between these two methods is mainly the printing step where the printing rollers are replaced by a digital non-contact printing process.

Digital printing may also be used to print on a paper sheet that is used in conventional laminate production and laminated under heat and pressure. The printing may be made prior or after impregnation. Such printing prior to impregnation is complicated since paper may swell and shrink during the printing and impregnation step and small quantities are not cost efficient to impregnate. Printing after impregnation on a melamine impregnated paper is very difficult since pigments applied on a melamine surface float during the pressing step when the melamine resin is in a liquid state. Such problems may partly be solved with a method where a raw paper, preferably comprising a base colour, is applied and fixed to the core prior to printing and impregnated paper or melamine powder is applied under and/or over the raw paper such that the resins from the impregnated papers penetrate into the raw paper during the pressing step.

Laminate floors may also have a surface of paper foils or plastic foils and such foil materials may also be printed digitally. A protective wear resistant transparent layer that generally is a polyurethane lacquer is used to covers the printed décor.

b) Powder Based Floors (WFF)

Recently new "paper free" floor types have been developed with solid surfaces comprising a substantially homogenous powder mix of fibres, binders and wear resistant particles hereafter referred to as WFF (Wood Fibre Floor).

The powder mix may comprise aluminium oxide particles, melamine formaldehyde resins and wood fibres. In most applications decorative particles such as, for example, colour pigments are included in the mix. In general, all these materials are applied in dry form as a mixed powder on a HDF core and cured under heat and pressure to a 0.1-1.0 mm solid layer. The powder is, prior to pressing, stabilized with moisture and IR lamps such that it forms an upper skin layer similar to a paper layer and this prevents the powder from blowing away during pressing. Melamine formaldehyde powder and wood fibres may be replaced by thermoplastic particles.

Several advantages over known technology and especially over conventional laminate floorings may be obtained such as increased wear and impact resistance, deep embossing, increased production flexibility and lower costs. An embossing depth of 0.2-0.7 mm may easily be reached.

Powder technology is very suitable to produce a decorative surface layer, which is a copy of stone and ceramics. In the past it was more difficult to create designs such as, for example, wood decors. However, recently digital powder printing has been developed and it is possible to create very advanced designs of any type by injecting ink into the powder prior to pressing. Problems related to paper impregnation may be completely eliminated since no impregnation is required. The surface structure is made in the same way as for laminate flooring by a structured press plate, a steal belt or an embossed matrix paper that is pressed against the powder. A major advantage compared to the other digital printing technologies is that the powder provides a base colour and no protective layer is needed above the print since the ink may penetrate into the powder. The penetration is however rather limited since the ink drops will be bonded to the first particle that they hit, mainly the wood fibres. Increased wear resistance may be reached if several printed powder layers are applied on each other or if a powder overlay is used as a protective layer applied over the digital print.

c) Melamine Formaldehyde Resin.

A basic substance in Laminate and WFF floors is the thermosetting melamine formaldehyde resin that is used as a binder. Melamine resin or melamine formaldehyde resin (generally shortened to melamine) is a hard, thermosetting plastic material made from melamine and formaldehyde by polymerization. Such resin, hereafter referred to as melamine, comprises three basic stages. The stages, A-stage, B-stage, C-stage are described in *Principles of Polymerization*, George Odian, 3rd edition, which is hereby incorporated by reference, including particularly pages 122 to 123. The first uncured A-stage is obtained when melamine, formaldehyde and water is boiled to a liquid substance with a dry content of about 50%. The second semi-cured B-stage is obtained when the liquid resin is used to impregnate, for example, an overlay paper that after the application of the liquid resin is dried with heat. The molecules have started to cross link but the resin is still possible to cure in a final stage if the drying of the resin is made during a rather short time, for example, one minute and with a heat of about 90-120° C.

The B-stage may also be obtained by spraying the liquid resin over hot air such that the drops are dried and a dry semi-cured melamine formaldehyde powder is obtained that comprises small round spherical particles with a diameter of about 30-100 microns (0.03-0.10 mm).

The final completely cured C-stage is obtained when, for example, the melamine impregnated paper or the WFF powder is heated to about 160° C. under pressure during 10-20 seconds. The dry melamine formaldehyde resin becomes softer, melts and cures to a fixed form when the temperature increases during the pressing. The curing is dependent on temperature and heating time. Curing may be obtained at lower temperatures and longer time or at higher temperature during shorter time. Spray dried melamine powder may also be cured under high temperature.

d) Wood Floors.

Wood floors are produced in many different ways. Traditional solid wood floors have developed into engineered floors with wood layers applied on a core made of wood lamellas, HDF or plywood. The majority of such floors are delivered as pre-finished floors with a wood surface that is coated with several transparent layers in the factory. The coating may be made with UV cured polyurethane, oil or wax. Recently wood floorings have also been produced with a digitally printed pattern that improves the design of the wood grain structure in wood species that do not have a sufficient surface quality.

e) Ceramic Tiles

Ceramic tiles are one of the major materials used for flooring and wall coverings. The raw materials used to form tiles consist of clay minerals, feldspar and chemical additives required for the shaping process. One common method to produce ceramic tiles uses the following production steps. The raw materials are milled into powder and mixed.

Sometimes, water is then added and the ingredients are wet milled. The water is removed using filter pressing followed by spray drying into powder form. The resulting powder is then dry pressed under a very high pressure (about 400 bars) to a tile body with a thickness of 6-8 mm. The tile body is further dried to remove remaining moisture and to stabilize the tile body to a solid homogenous material. Recently dry pressing of large and thin panels have been introduced. Dry granular material is pressed with very high pressure up to 400 bars and panels with a size of 1*2 m and more and with thicknesses down to a few mm may be produced in a cost efficient way. Such panels may be used for wall panels and worktops. The production time has been reduced from several days to less than an hour. Such panels may be cut and shaped with production tolerances that are superior to the traditional methods and the may even be installed in a floating manner with mechanical locking systems. One or several layers of glaze, which is a glass like substance, are applied on the tile body by dry or wet methods. The thickness of the glazing is about 0.2-0.5 mm. There may be two glazes on the tile, first a non-transparent glaze on the tile body, then a transparent glaze on the surface. The purpose of tile glazing is to protect the tile. The glaze is available in many different colours and designs. Some glazes can create different textures. The tile is after glazing fired in a furnace or kiln at very high temperatures (1,300° C.). During firing, the glaze particles cure and melt into each other and form a wear resistant layer. Roller screens are often used to create a decorative pattern. The contact nature of the rotary screen-printing has many disadvantages such as breakages and long set-up times. Several tile producers have therefore recently replaced this conventional printing technology with digital ink jet printing technology that offers several advantages. Generally oil based inks are used and the print is applied on the pressed tile body or on a base glazing that is applied in wet form and dried prior to printing. A transparent glaze layer may be applied on the digital print in order to improve the wear resistance. Digital non-contact printing means no breakages and possibility to use thinner tile bodies. Short set-up times, randomized printing with no repetition effects and ability to print on surfaces of variable structures and on tiles with beveled edges are other major advantages. Additional circumstances that have contributed to the introduction of the digital printing technology in the tile industry is the fact that ceramic tiles are rather small compared to, for example, laminate and powder based floors that are produced as large pressed boards of about 2.1*2.7 m. Rather small printers with limited number of print heads may be used in the tile industry and the initial investment is rather limited. Oil based inks have a very long drying time and clogging of nozzles may be avoided. Other advantages are related to the glazing that provides a base colour. Generally smaller amounts of pigments are required to form a tile pattern on a base colour than to provide an advanced wood grain design on a HDF or paper material used in laminate floorings where impregnation and lamination creates additional problems.

f) LVT Floorings.

Luxury Vinyl Tiles, generally referred to as LVT floorings, are constructed as a layered product. The name is somewhat misleading since a major part of LVT floors have a plank size with a wood pattern. The base layer is made primarily of several individual base layers comprising different mixtures of PVC powder and chalk filler in order to reduce material costs. The individual base layers are generally about 1 mm thick. The base layer has a thin high quality printed decorative PVC foil on the upper side. A transparent wear layer of vinyl with a thickness of 0.1-0.6 mm is generally applied on the decorative foil. Glass fibres are often used to improve thermal stability. The individual base layers, glass fibres, the decorative foil and the transparent layer are fused together with heat and pressure in continuous or discontinuous presses. The transparent layer may include a coating of polyurethane, which provides additional wear and stain resistance. Some producers have replaced the transparent vinyl layer with a polyurethane layer that is applied directly on the decorative foil. Recently new types of LVT floors have been developed with a base layer thickness of 3-6 mm and with edges comprising mechanical locking systems that allow floating installations. LVT floors offer several advantages over, for example, laminate floors such as deep embossing, flexibility, dimensional stability, moisture resistance and lower sound. Digital printing of LVT floors is only on an experimental stage but would, if introduced, provide major advantages over conventional printing technology.

As a summary it may be mentioned that digital printing is used in several floor types to create a décor. However the volumes are still very small, especially in wood and laminate flooring applications, mainly due to high cost of the ink and high investment cost for the industrial printers. The flexibility that the digital printing technology provides is limited by the embossing that is fixed and not possible to adapt to the variations of the digitally printed décor. It would be a major advantage if the ink cost could be reduced, if more cost efficient printing equipment could be used in an industrial scale, if a higher wear resistance could be reached without separate protective layers and if variations in the embossed structures may be formed that correspond to variations in the digitally printed pattern.

Definition of Some Terms

In the following text, the visible surface of the installed floor panel is called "front side", while the opposite side of the floor panel, facing the sub floor, is called "rear side".

By "up" is meant towards the front side and by "down" towards the rear side. By "vertically" is meant perpendicular to the surface and by "horizontally" parallel to the surface.

By "pigments" is meant a very fine powder of solid colorant particles.

By "pigment ink" is meant an ink comprising pigments that are suspended or dispersed throughout a carrier fluid.

By "binder" is meant a substance that connects or contributes to connect two particles or materials. A binder may be liquid, powder based, a thermosetting or thermoplastic resin and similar. A binder may consist of two components that react when in contact with each other. One of the components may be liquid and the other dry.

By "matrix" also called "mat" is meant a material that forms an embossed surface structure when the material is pressed against a surface.

By "Embossed In Register" or EIR means that a printed décor is in register with an embossed structure.

By "digital ink jet printing" is meant a digitally controlled ejection of drops of fluid comprising a colorant from a print head onto a surface.

By "digital print" is meant a digitally controlled method to position colorant onto a surface.

By "colourant" is meant any material (dye, organic or inorganic pigments, small coloured particles of any material etc.) that may be used to provide a colour on a surface preferably due to selective absorption or reflection of different wavelengths of light.

By "panel" is meant a sheet shaped material with a length and width that is larger than the thickness. This rather broad definition covers, for example, laminate and wood floors, tiles, LVT, sheet shaped wall coverings and furniture components.

Known Technique and Problems Thereof

The generally known technologies, which may be used to provide a digital print and an embossed surface structure, are described below. The methods may be used partly or completely in various combinations with preferred embodiments of the invention in order to create a digital print or a digital embossing according to this disclosure of the invention.

High definition digital ink jet printers use a non-impact digital printing process. The printer has print heads that "fire" drops of ink from the print head to the surface in a very precise manner.

Multipass Printing, also called scanning printing, is a printing method where the printer head moves transverse above the surface many times to generate an image. Such printers are slow but one small print head can generate a bigger image.

Industrial printers are generally based on a Single Pass Printing method, which uses fixed printer heads, with a width that corresponds to the width of the printed media. The printed surface moves under the heads. Such printers have a high capacity and they are equipped with fixed print heads that are aligned one after each other in the feeding direction. In general each head prints one colour. Such printers may be custom made for each application.

FIG. 1a, shows a side view of an industrial single pass digital ink jet printer 35 comprising five digital print heads 30a-e, which are connected with ink pipes 32 to ink containers 31 that are filled with ink of different colours. The ink heads are connected with digital data cables 33 to a digital control unit 34 that controls the application of the ink drops and the speed of the conveyor 21 that must be able to displace the panel under the print heads with high precision in order to guarantee a high quality image comprising several colours.

FIG. 1b shows a top view of a wood grain print P provided on a panel surface 2. The surface of a floor panel is often embossed with a basic structure 17 that is the same for several basic decors as shown in FIG. 1c. Advanced floors use a so-called EIR (Embossed In Register) embossing 17 that is coordinated with the printed pattern P as shown in FIG. 1d.

A normal width of an industrial print head is about 6 cm and any lengths may be printed. Wide areas of 1-2 m may be printed with digital printers comprising several rows of print heads aligned side by side. 166 print heads may be needed to provide a 5-colour print on a 2 m wide laminate floor panel and the print may be destroyed if only a few nozzles in one print head are blocked by dry ink.

Number of dots per inch or DPI is used to define the resolution and the printing quality of a digital printer. 300 DPI is generally sufficient to, for example, print wood grains structures of the same quality presently used in conventional laminate floorings. Industrial printers can print patterns with a resolution of 300-600 DPI and even more and with a speed exceeding 60 m/min.

The print may be a "full print." This means that the visual printed décor is mainly created by the ink pixels applied on the surface. The colour of a powder layer or a base colour of a paper has in such an embodiment, in general, a limited effect on the visible pattern or décor.

The print may also be a "part print". The colour of another underlying layer is one of the colours that are visible in the final décor. The area covered by printed pixels and the amount of ink that is used may be reduced and cost savings may be obtained due to lower use of ink and increased printing capacity compared to a full print design. However a part print is not as flexible as a full print since the base colours are more difficult to change than when a full print is used.

The print may be based on the CMYK colour principle where the white colour is provided by the surface. This is a 4-color setup comprising cyan, magenta, yellow and black. Mixing these together will give a colour space/gamut, which is relatively small. To increase specific colour or the total gamut spot colours may be added. A spot colour may be any colour. The colours are mixed and controlled by a combination of software and hardware (print engine/print heads). The flexibility may also be increased considerably by adding a white colour to the printer.

New technology has been developed by CeraLoc Innovation Belgium BVBA, a subsidiary of Välinge International AB that makes it possible to inject a digital liquid print into a powder layer. This new type of "Digital Injection Print" or DIP is obtained due to the fact that printing is made into a powder that is cured after printing. The ink and the print are embedded into the cured layer and they are not applied on a layer as when conventional printing methods are used. The print may be positioned in several dimensions horizontally and vertically in different depths. This may be used to create 3D effects when, for example, transparent and preferably bleached wood fibres are used. A two-layer print may also be used to increase the wear resistance. No protective layers of, for example, overlay are needed that disturb the original design with grey shadings.

The DIP method may be used in all powder based materials, which may be cured after printing. However, the DIP method is especially suitable to be used when the powder comprises a mix of wood fibres, small hard wear resistant particles and a melamine resin. The surface layer may also comprise thermoplastic material, for example, vinyl particles, which are applied in powder form on a surface. This allows that the print may be injected in the vinyl powder particles. An improved design and increased wear resistance may be reached even in such materials.

A suitable printer head has to be used in order to obtain a high printing quality and speed in powder based layers and other layers as described above. A printer head has several small nozzles that can shoot and apply droplets of inks in a controlled way.

Industrial inkjet systems, are broadly classified as either continuous inkjet (CU) or drop on demand (DOD) systems.

CIJ ejects drops continuously from the print head. The drops pass through a set of electrodes, which impart a charge onto each drop. The charged drops then pass a deflection plate which uses an electrostatic field to select drops that are to be printed and drops to be collected and returned for re-use.

DOD ejects drops from the print head only when required and all drops are applied on the surface.

CIJ is primarily used for coding and marking of products. DOD inkjet technology is currently used in most existing industrial inkjet applications where a high quality décor is required.

A normal size of an ink droplet is about 2-4 picolitres ($=1*10^{-12}$ litre or 0.000001 $mm^3$). The size of each droplet may vary, dependent on ink type and head type, normally between 1-40 picolitres and this corresponds to a droplet that has a diameter of about 10-30 microns. Smaller droplets enable high-resolution images. Some printer heads can shoot different droplet sizes and they are able to print a grey scale. Other heads can only shoot one fixed droplet size. It is possible to design print heads that may fire bigger drops up to 100-200 picolitres or more.

Several technologies may be used to shoot the drops out of the nozzles.

Thermal print head technology generally referred to as bubble jet printing, use print cartridges with a series of tiny chambers each containing a heater. To eject a droplet from each chamber, a pulse of current is passed through the heating element causing a rapid vaporization of the ink in the chamber to form a bubble, which causes a large pressure increase, propelling a droplet of ink out through the nozzle and to the surface. Most consumer inkjet printers use thermal printer heads. Such thermal printers are generally designed to apply water based inks with a viscosity of 2-5 centipoise (cps)

Recently large-scale thermal print heads with a printable width of 223 mm and with a printing speed of about 20 m/min or more have been developed by Memjet. The print head contains 5 ink channels and two rows of nozzles per channel. Each individual nozzle structure is about 30-microns across, enabling 800 dpi, with the second row of nozzles for each colour slightly offset from the first to deliver 1600 dpi in combination. A Memjet print head can continuously fire up to 750 million 2 picolitres drops with a 14 micron drop diameter per second. The print head cost is less than 10% of the costs for conventional Piezo heads with similar capacity. Such thermal printers may apply water based substances with a viscosity of 0.7-1.5 centipoise which is similar to water viscosity (1 centipoise at 20° C.). The Memjet print head comprises a self-cooling system with the heating element in the middle of the ink chamber. As drops are ejected, new ink flows into the chamber and cools the heating element.

Thermal technology imposes the limitation that the ink must be heat-resistant, generally up to 300° C. because the firing process is heat-based. This makes it very difficult to produce pigment based multi colour thermal heads. The Memjet print heads are designed for dye based ink and are therefore not used in the flooring industry and in industrial applications where high quality pigment based inks are required.

Most commercial and industrial inkjet printers and some consumer printers use the piezoelectric printer head technology, which is the major technology used in the flooring industry. A piezoelectric crystal material (generally called Piezo) in an ink-filled chamber behind each nozzle is used instead of a heating element. When a voltage is applied, the piezoelectric material changes shape, which generates a pressure pulse in the fluid forcing a droplet of ink from the nozzle. A Piezo print head configuration may use different basic deformation principles to eject drops from a nozzle. These principles are generally classified in squeeze, bend, push and shear print head technologies. A piezoelectric crystal may also be used to create acoustic waves as it vibrates and to cause the ink to break into droplets at regular intervals. Piezo inkjet allows a wider variety of inks and higher viscosity than thermal inkjet. The ink has generally a viscosity in the range of 2-12 centipoise and is very suitable to apply pigment based ink. In industrial applications print heads that may handle high viscosity inks are often used since the initial viscosity of the ink decreases considerably during production when temperature may increase to 40° C. or more and a low initial viscosity may fall below the minimum level that is required for a proper functioning of the print head.

FIG. 1e shows how ink drops 56 are ejected according to the bend mode of piezoelectric material. A Piezo print head 30 comprises arrays of very small holes generally called jets 50 from which droplets 56 of ink 58, with pigments 12, are ejected on a paper surface.

The ink 58 flows from an ink container via an ink inlet 55 into an ink chamber 52. Electrical pulses bend a Piezo crystal 51 and a membrane 53. This deformation creates a pressure pulse that ejects an ink drop 56 from the nozzle 54. Different drop sizes may be formed by varying the electrical charge. The nozzles are typically about 10 microns in diameter. Typical drop volumes are in the range of 2-5 picoliters producing printed ink spot sizes 57 on a surface in the range of 10-20 microns. Each droplet may contain about 20% pigments. The remaining part is a liquid carrier and resins needed to connect the pigments to the surface.

A digital image contains a grid of a fixed number of rows and columns of pixels, which are the smallest individual element in a digital image. The grid is called a raster. The pixels, which represent images as a computer file, are of a uniform size and shape. They do not overlap and they touch adjacent pixels on all sides. Raster images can be created by a variety of input devices, for example, a digital camera. All known printers use a Raster Image Processing (RIP) software, which takes an image file input and produces a colour profiled, screened, bitmap output that controls the print heads and provides the necessary data that is needed to apply an ink drop on a surface in a pre-determined raster pattern R1-R4 as shown in FIG. 1e.

A lot of ink types may be used. The main components are colourants that provide the colour, a binder that bonds the colourants to the surface and a liquid carrier that transfers the colorant and the binder from the print head in well-defined small drops to a surface with a non-contact application method. The colourant is either a dye or pigment or a combination of both. The carrier fluid may be water-based or solvent based. The carrier fluid evaporates and leaves the colourant on the surface. UV curable inks are similar to solvent based inks but the carrier fluid cures when exposed to strong UV light.

A main problem for all types of inks and print heads is that when ink dries by evaporation it may dry up and clog the nozzles. Industrial printers may be equipped with an ink circulation system that circulates the ink through the jets in order to increase the so called "decap" time which is the amount of time a print head can be left uncapped and idle and still fire ink drops properly. A short decap time or clogging may results in permanent nozzle loss and undesired lines may be formed over the whole surface when single pass printers are used. Especially pigment-based inks comprising polymer binders systems have a tendency to dry out and it would be a major advantage if the decap time could be increased and nozzle clogging could be avoided.

A dye is a colourant that is dissolved fully into the carrier fluid and the ink is a true solution.

Pigments are very fine powder of solid colourant particles that are suspended or dispersed throughout a liquid carrier. Pigment based inks are generally individually mixed together by using colour pigments and several chemicals. Pigments used in digital ink are very small and have an average particle size of about 0.1 micron. The common size of the nozzles is about 10-20 microns, which means that the pigment particles have enough space to pass through the nozzle channels in the print head. The nozzles may still be blocked by the ink itself and pigments that form clusters of particles. High quality pigment ink should keep the pigment suspended in the carrier fluid for a long period of time. This is difficult particularly at the rather low viscosities, which are required for a good functioning of the print heads.

Pigments have a natural tendency to settle out and fall down in the liquid carrier. In high quality pigment ink, no settling out of the pigment should normally occur. Advanced ink circulation systems are used to avoid such problems related to ink with high pigment content.

Pigment inks are generally more light stable, especially when exposed to UV light, and more fade resistant than dye-based inks. They are therefore used in almost all flooring applications. Water based digital inks comprising colour pigments are especially suitable for flooring applications and may provide a high quality printing method in many different materials.

Generally the pigments do not stick to a smooth surface. They are similar to sand particles and may be easily removed from most dry and smooth surfaces. The water based carrier fluid is therefore generally mixed with small amounts of several other additives to provide special ink and print properties such as binders that provide the adhesion of the pigments to a surface, dot gain, pH level, drop formation, corrosion of the print head, fade resistance, etc. The inclusion of resins that serve as binder in the ink composition limits the possible amount of pigments, as both components increases the ink viscosity.

Colour pigments as raw materials are rather cost competitive especially as rather large particles of about one micron but the production of pigment based inks comprising very small particles and other inks for digital printers is very complicated and expensive and this results in a very high cost for the ink that normally may be in the region of about 50-100 EUR/litre. About 50-100 $m^2$ of flooring may be printed with one litre (20-10 $g/m^2$) if a full high quality print is applied and this gives a printing cost of 1-2 $EUR/m^2$. The costs for a conventional printed floor surfaces where printing cylinders are used are only 10% of the cost for digitally printed floor surfaces. This means that digital printing based on conventional pigment based liquid ink is only cost competitive in small series when very high production flexibility is required.

Digital ink jet printers use a non-contact method to apply the ink on a surface. Laser printing however is based on a contact method where a laser beam projects an image on an electrically charged rotating drum, generally called photo conductor drum. Dry ink particles, generally called toner, are then electrostatically picked up by the drum's charged areas. The ink comprises fine and very well defined spherical particles of dry plastic powder such as, for example, styrene acrylate copolymer or polyester resin which is mixed with carbon black or colouring agents. The particles have a diameter of about 8-10 microns when 600 DPI printing resolution is required. Some laser printers use even smaller particles with a diameter of about 5 microns. The thermosetting plastic material acts as a binder. The drum prints the image on a paper by direct contact and heat, which fuses the ink to the paper by bonding the plastic powder to the paper. Colour laser printers use the CMYK principle with coloured dry ink, typically cyan, magenta, yellow, and black that are mixed in order to provide a high quality coloured image.

The laser technology with the impact method is not used for printing of a flat panel surfaces such as a floor panel surfaces.

3D printing is a well-known technology that is used to apply and connect several layers of liquid substance, powder or foils on each other in order to create advanced three dimensional structures. The technology is mainly used for prototype production of small complex products. Several hundred layers may be applied on each other. Several principles are used to build layered structures. According to one main principle powder layers are applied on each other and some parts are bonded by a liquid UV cured substance applied by a digital print head on each powder layer. Non-bonded powder is removed when the whole structure of the product is formed. Another principle uses a small glue gun that applies several layers of hot liquid plastic material in several layers. 3D printers have a very low productivity and construction of even small objects can take several hours. 3D printers are not used to create flat decors on a surface where colourants are applied side by side and where non-bonded powder must be removed after each application of a layer. The structure of the layers applied on each other will be destroyed if pressing is used to cure the layers.

Dye-sublimation printers use a long roll of transparent film of red, blue, yellow, and grey coloured cellophane sheets that are attached together end to end. Embedded in this film of many sheets attached to each other are solid dyes corresponding to the four basic colours cyan, magenta, yellow and black and each sheet comprises only one colour. The "print head" contains thousands of small heating elements that produce varying amounts of heat and the dye is transferred to a coated paper with "sublimation" which means that the dye when heated turns into a gas without first turning into a liquid. Such thermal print heads, hereafter referred to as heating print heads in order to differentiate such heads against the thermal print heads used in bubble jet printing, heats up as it passes over the film, causing the dyes to vaporize before they return to solid form on the paper. This method eliminates the used of liquid ink and may provide a high photo quality with dyes that are transparent and that blend into a continuous-tone colour. However, the method has many disadvantages. Each sheet must have the same size as the printed surface and the whole sheet is used even if a small part of the surface is printed with a specific colour. In order to eliminate some of the disadvantages dye sublimation heat transfer imprinting printers have been developed, which use special inks comprising sublimation particles. A conventional inkjet printer may be used to print an image with such sublimation ink on a special paper or foil. The image is thereafter transferred by pressure and heat to a polyester material or a surface that has a polymer coating.

Thermal printing with heating print heads are also used to create digital prints directly on a heat sensitive paper or indirectly with a thermal transfer printing method where the heat is applied on a heat sensitive transfer film. These printing methods are mainly used to apply one colour on a paper and to print, for example, labels. The heating print heads have several advantages. They are reliable since there are no risks for clogging of inks and the price is cost competitive. The major disadvantages are related to high cost for the paper or transfer film and the colour limitations to mainly one colour. Heating print heads are available in widths of up to 200 mm and may provide a resolution of up to 600 DPI.

Digital printing is a very flexible method that may provide a high quality print but it cannot be fully utilized in industrial application and especially not in floorings due to the high cost for the ink, problems related to drying and clogging of nozzles, especially when pigment based inks are used and the need for special protective layers that are costly and not completely transparent. The high ink costs are primarily caused by the need to mill down the colour pigments to well-defined very small particles and to disperse the particles throughout the carrier fluid. It would be a major advantage if digital images may be created with colour pigments that may be larger, that are not dispersed in a carrier fluid and that are not applied as drops by small nozzles. It would also be a major advantage if digital images may be formed with higher wear resistance and without protective layers.

The majority of all the above-described floors and especially digitally printed floors have an embossed surface structure, especially when the decorative printed décor is a wood pattern. The embossed structure was in the past provided as a separate general structure that was used for many different décor types. Recently most floor producers have introduced the so-called Embossed In Register EIR method where the embossed surface structure is specifically formed for each type of wood species and the embossing is made in register with the printed décor. This provides advanced designs that are difficult to differential from the natural materials such as wood and stone. The embossing is obtained when the surface is pressed against a structured matrix that may be a steal plate, steal belt, metal roller, plastic foil or coated paper. The décor must be positioned with high precision against the pressing matrix. Generally digital cameras and mechanical devices that adjust the final position of the panel such that it matches the décor before pressing are used to obtain such positioning. One specific problem related to laminate flooring is the fact that the printed-paper swells and shrinks in an uncontrolled way during impregnation and the size of the décor may vary between different impregnate paper sheets.

The flexibility of digital printing is also limited in connection with EIR surfaces since the printed décor must always be adapted to the embossed matrix. A common feature for all such floors as described above is that all surfaces in a production batch have the same basic structure and are not possible to adjust and adapt to any changes in the décor. This repetition effect of the embossed structure provides a floor surface that is not similar to a wood floor where practically all panels have different designs and structures due to the wood grain structure of the wood. Copies of stone and other natural materials cannot be produced in a way that is a true copy of the natural material where design and structure generally is perfectly combined and all panels are different.

The digital ink jet technology is mainly used to obtain advantages related to the possibility to create a high-resolution image in a flexible way. However, the other aspects of the technology, mainly related to the possibility to apply a liquid substance very precisely with a non-impact method, have not been fully utilized or developed, especially not in applications where a décor is applied on a large size panel comprising a surface that during production and especially after printing receives it final shape and properties in production steps comprising high pressure and heat.

It is known that powder applied on a liquid substance could be used to create raised portions or an image on mainly a paper substrate and that the liquid substance may be applied digitally by ink jet. 3-D printing comprising several powder layers that are locally connected with a digital device such as an ink head and where excessive non-connected powder particles are removed in a final step is a well-known technology that may be used to create an embossed structure on a panel. It is also known that powder particles may be applied directly with a non-contact method on a surface comprising a binder or indirectly with a contact method where a transfer method is used. Even combinations are known where a non-contact transfer method is used and the powder is detached from the transfer surface with heat or scraping.

U.S. Pat. No. 3,083,116 describes raised printing powder and a raised printing process comprising dusting a powdered resin upon a newly printed sheet, removing therefrom the excess powder which do not adhere to the wet ink, and applying heat to the powder retained on the sheet to fuse it so that particles thereof will flow together and adhere to the sheet. The powder may comprise a phenolic resin such as phenol, urea and melamine.

U.S. Pat. No. 3,440,076 describes a method of forming raised hard printed characters on a sheet of paper. An ink composition is printed on the paper and then contacted with a dry material. One of the ink composition and dry material contains a thermosetting resin and the other material a blowing agent and a curing agent. The dry powder material not adhering to the ink is removed and the resin associated with the printed character is then cured with heat at temperatures sufficient to fuse the powder.

U.S. Pat. No. 3,446,184 describes a method to form a sticky image copy. Toner powder is applied on a liquid forming and a portion of the powder is retained by the liquid coating, forming a visible image. Loose powder is removed and the sheet passes a heating unit where the retained powder is fused to form a permanent image.

U.S. Pat. No. 4,312,268 describes a method by which a water-based ink is applied digitally to a continuous web and fusible single colour powder material is applied to the web and on the ink. Some of the powder material is bonded to the liquid, and non-bonded powder material is removed from the web prior to heating of the web to dry the liquid and to fuse the powder material to the web by melting the powder. It is mentioned that the powder material may have a particle size in the range of 5 to 1000 microns and may have a melting point or fusing point in the range of 50 to 300° C. The powder material may be produced by dissolving or dispersing, respectively, a dye or a pigment in a resin or resin formulation, followed by grinding, spray chilling or the like to reduce the material to a fine powder. The powder material may provide abrasion resistant qualities to the ink that may contain phenolic resin. The liquid material, which is applied through the jets, may be clear and colourless water.

GB 2 128 898 describes a method to form raised decorative portions in a plastic tile. A decorative floor covering in tile form has a design printed on its upper surface. Particles such as inorganic sand particles are positioned on the upper surface of a plastic tile with at least some of the particles being placed on the tile surface in register with the design printed on the tile surface. Excess sand particles are removed. A cured wear layer overlies both the raised particle and the plastic base, whereby the wear layer surface in the areas containing particles and in the areas not containing particles will be of different gloss characteristics. The process requires the sprinkling of particles over an adhesive coated surface to retain the particles in registration with a printed design on the tile surface.

U.S. Pat. No. 6,387,457 describes a method of using dry pigments for printing applications related to automobile painting, security printing, general painting and cosmetics. A binder material is applied to a surface of a substrate uniformly or in a pattern. The binder is applied by ink jet, spraying, screen, off-set or gravure printing. Dry pigment is applied to the binder material in a pattern or uniformly. The dry pigment material comprises flakes of non-metallic material having a particle size less than about 100 micron. The flakes are aligned in a direction parallel with the surface of the substrate and a protective coating may be applied on the flakes.

EP 0 403 264 A2 describes a transfer method to form a multi-colour image on a drum that transfers the image to a paper. A fluid digital latent image is subsequently developed at a development station where coloured powder is applied to the fluent latent image and fixed to produce a visible and permanent image. Several digital print heads may be used that print with dyeless fluids comprising a mixture of water with polyhydric alcohols and their sub-sets of ethylene glycol, glycerol, diethylene glycol and polyethylene glycol. A powder toner is applied across the surface of the paper and a voltage is applied during this development. The voltage is then reversed to remove the toner from the background areas. Fixing is achieved by means of conventional copier fusing methods.

U.S. Pat. No. 5,627,578 describes a method to produce raised lettering and graphics in desktop printing applications by using thermographic powder and an ink jet printer to apply a liquid binder. The method is similar to the above described methods to produce raised text.

EP 0 657 309 A1 describes a multicolour transfer method utilizing a transfer paper carrying a pattern formed by ink jet and powder similar to the above described methods. The transfer method is intended for decorating ceramics.

WO 2007/096746 relates to systems and apparatuses for transferring granular material with a non-contact or contact method to a surface to be decorated, particularly for obtaining decorations on ceramic tiles. A liquid digital pattern is provided by ink jet on a transferring surface that may be a drum or a belt. The granular material is applied and bonded to the transferring surface and only bonded granulate material is moved to a transferring zone where heat is applied on one specific portion of the transferring surface in the transferring zone in order to detach the granular material from the transfer surface and to apply the granular material on the receiving surface. The granules may also be detached by scraping. The major advantage with this method is that only particles that form the final image are applied on the receiving surface. The major disadvantage is that heating must be sudden and the particles must be released from the transferring zone and they must fall down on the receiving surface in a very controlled way in order to obtain a high resolution image. High resolution can only be obtained with rather heavy particles that fall by gravity on the receiving surface. The granular material used in the invention is of the type comprising non-porous granules, such as, for example, grits of vitreous materials or sintered mixtures, sands etc. in the various ranges of granulometry from 30 μm to 800 μm, preferably ranging from 50 μm to 150 μm. A transfer print with a contact method is also described.

WO 2011/107610 describes a method to create an elevation or an embossing on a floor panel in order to avoid the use of expensive press plates. The method is the same as the known methods to create a raised print. It describes a method to produce a floorboard by printing a curable substance for creating an elevation on the panel. The elevation may be applied on a basic decorative pattern that is directly printed or laminated on the panel. The curable substance may comprise wear resistant particles. The curable substance may be digitally printed on the panel by first printing a liquid in a pre-defined pattern and then providing an intermediate substance that may comprise a powder. The curable substance may be cured by UV radiation or may be a varnish.

EP 2 213 476 A1 describes that a pre-determined pattern may be digitally printed on a carrier with curable liquid so as to form an embossing decoration pattern, which is pressed on the overlay. The curable liquid may be a plastic, which becomes rather rigid after curing, for example, a plastic containing ink. This method is not suitable for floor applications. The digital printing head can only print a very thin layer with a thickness of about 10-20 micron. Thicknesses of at least 100-200 micron that are required to form an embossing in laminate and 200-700 micron to match the requirement of powder based floors are not possible to produce in an economic way.

WO 2012007230 describes a method to form a 3-D structure on a furniture or floor panel with a digitally controllable device. A décor is applied with a flat three-dimensional structure of powder based coating material comprising one or more layers, which are locally solidified by a digitally controllable device under the action of light and or heat radiation. Excess non-solidified coating material is removed in a final production step. The three dimensional structure may be digitally printed. A liquid coating material is applied on the 3-D structure as a protective layer.

The majority of the known methods are based on direct application of powder on a surface comprising a binder pattern. They are mainly used to create raised text or three-dimensional decors, which are cured and protected by a liquid coating. Such methods are not suitable for application where the coloured powder must be incorporated into the surface in order to provide sufficient wear resistance. None of these direct application methods are combined with a pressing step that compresses the applied powder and especially not with a pressing step that cures the whole surface layer such that the powder particles are cured or fused into the surface.

Dye-sublimation printers with heating print heads use special coloured films and are not suitable to produce surfaces with high wear resistance such as floor surfaces. Heating print heads are no used to bond powder that is applied on a surface, especially not on a panel surface.

The known methods are not suitable for creating a high quality multi-colour image on a building panel, and especially not on a floor panel where UV resistant pigments must be used and where the image must be incorporated into a wear resistant surface. It is not known that above describe principles may be used to create a digital image on a panel that after the printing step is cured under high heat and pressure and especially not how the known principles should be adapted for printing of floor surfaces similar to laminate and Wood Fibre Floors (WFF) where the powder, the ink and the application methods must be adapted to the specific thermosetting resins, wood fibre materials and pressing parameters which are needed to form a wear, impact and stain resistant high quality multi-colour surface in a cost efficient way.

The above description of various known aspects is the applicants' characterization of such, and is not an admission that the above description is prior art when the described products, methods and equipment are used partly or completely in various combinations.

Objects and Summary

The main objective of at least certain embodiments of the invention is to provide an improved and cost efficient printing method to apply colourants on a surface in well-defined patterns on preferably a floor panel surface by using digital technology.

A specific objective is to provide a method wherein heating print heads that contain a large number of small heating elements that produce varying amounts of heat may be used.

The above objectives are exemplary, and the embodiments of the invention may accomplish different or additional embodiments.

Embodiments of the invention is based on a main principle where conventional digital printing methods are divided in separate steps. Coloured particles are applied on a surface.

Some particles are bonded by a digital heating print head. Other non-bonded particles are removed and the remaining bonded particles form a digital pattern. This process may be repeated and several colours may be applied such that an advanced multi colour high definition digital print may be formed. The coloured particles may be pigment coated wood fibres or mineral particles and very realistic copies of wood and stone designs may be obtained with such decorative materials arranged in advanced high quality patterns. The bonded coloured particles and the panel surface are pressed together and an increased bonding is obtained. The pressing is made under increased temperature such that the coloured particles and the surface are cured to a hard wear resistant layer.

An advantage compared to conventional digital ink jet printing are that the coloured particles are not dispersed in a liquid substance and are not applied by a digital printing head on a surface. Pigment based colourants may be combined with very cost effective and reliable heating print heads where no liquid inks are used that may evaporate and clog the nozzles.

An advantage compared to known Dye-sublimation printers with heating print heads is that no special coloured films have to be used. Colourants and binders may be adapted to specific requirements that must be met in order to produce surfaces with high wear resistance such as floor surfaces.

A first aspect of the invention is a method of forming a digital print on a surface, wherein the method comprises:
applying a powder of dry ink, the dry ink comprising colourants, on the surface;
bonding a part of the powder of dry ink to the surface by a digital heating print head such that the digital print is formed by the bonded colourants of the dry ink; and
removing non-bonded dry ink from the surface.

The dry ink may comprise a heat sensitive resin.

The surface may comprise a heat sensitive resin.

The heat sensitive resin may be a thermosetting or thermoplastic resin.

The heat sensitive resin may be a thermosetting resin comprising melamine.

The digital heating print head may apply heat on a heat transfer foil that is in contact with the digital heating print head and the dry ink particles.

The heat transfer foil may comprise copper or aluminium.

The surface may be a part of a building panel.

The dry ink may comprise mineral particles.

The dry ink may comprise aluminium oxide particles.

The heat transfer foil may comprise individual small elements with high thermal conductivity.

The dry ink may comprise wood fibres.

BRIEF DESCRIPTION OF THE DRAWINGS

The invention will in the following be described in connection to preferred embodiments and in greater detail with reference to the appended exemplary drawings, wherein, FIGS. 1a-e Illustrate know methods to produce a printed and embossed surface.

DETAILED DESCRIPTION OF EMBODIMENTS

The methods that are used to provide a digital print with heating print heads are in this disclosure based on similar technologies that are used to bond powder with thermal digital ink jet print heads. A detailed description of the liquid bonding methods are therefore included. The digital technologies that are based on liquid bonding, heat bonding and conventional ink jet printing may be combined and a panel may for example comprise several colours formed by a combination of such digital printing technologies.

Figure 1A:
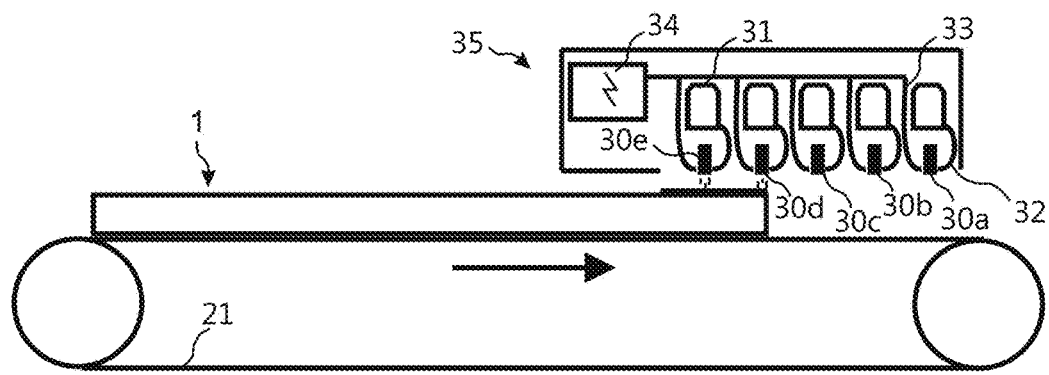
Figure 1B:
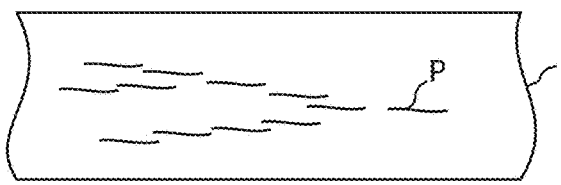
Figure 1C:
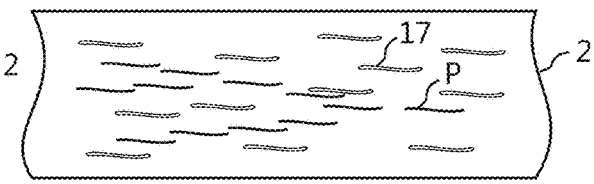
Figure 1D:
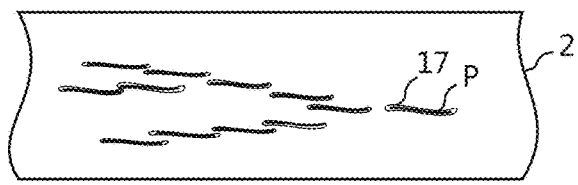
Figure 1E:
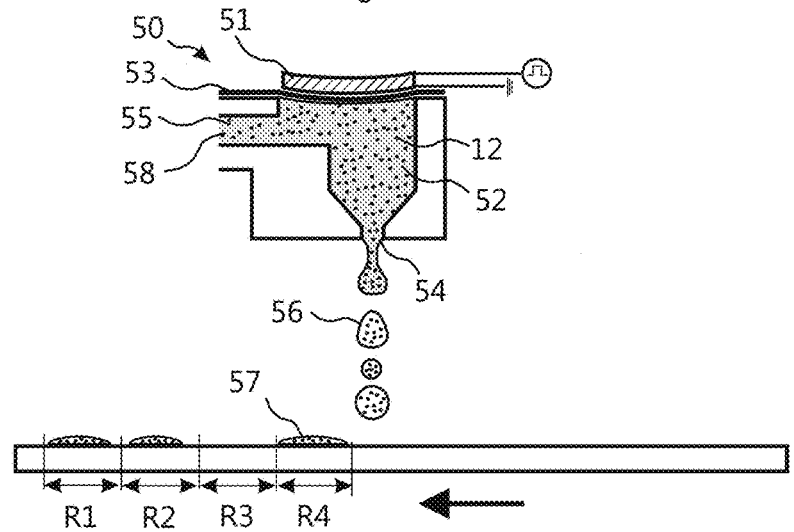
Figure 2A:
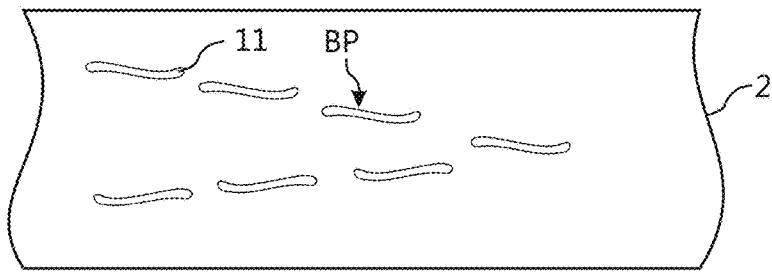
FIGS. 2a-e Illustrate a first principle of an embodiment of the invention.
Figure 2B:
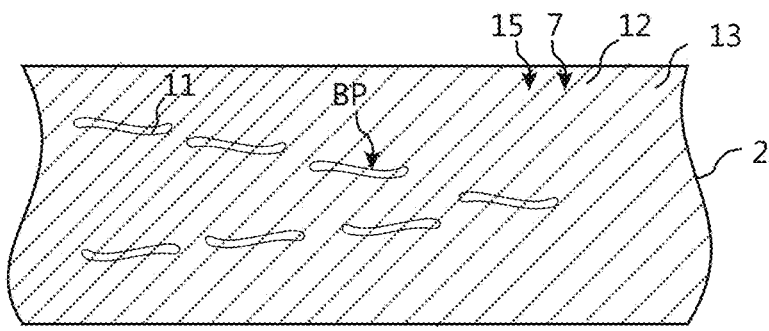
Figure 2C:
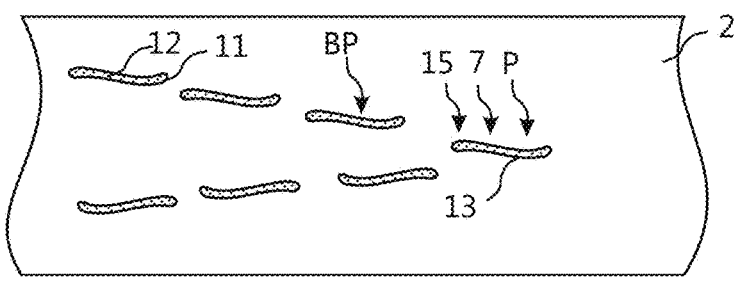

FIGS. 2a-2d show schematically an embodiment of the invention, which is based on a first principle where a binder pattern BP or image is formed digitally by an ink head that preferably only applies a binder 11 on a surface 2 as shown in FIG. 2a. Colourants 7, that may comprise small coloured particles, for example, pigments 12, are applied randomly preferably in dry form by a second device such that they are in contact with the binder pattern BP. FIG. 2b shows a preferred embodiment where pigments 12 in dry form are scattered over the binder pattern BP. FIG. 2c shows that the binder 11 connects some pigments 12 that form the same pattern as the binder 11 and a print P is formed on the surface 2 when other non-bonded pigments 12 are removed from the surface 2 by, for example, vacuum.

This three-step process, hereafter referred to as "print forming cycle", when the process relates to a one colour application, or "Binder And Powder printing", or BAP printing, when the process refers to the whole print and where preferably a liquid binder 11, hereafter referred to as "blank ink" and dry particles comprising colourants 7, hereafter referred to as "dry ink" 15, are applied separately and bonded together and where non-bonded particles are removed, may provide a digital print P with the same or even superior quality as conventional digital printing technology.

The surface 2 may be a paper layer or a foil or a powder layer.

The surface 2 may be a part of a building panel or a floor panel 1.

The binder may be blank ink 11 comprising a liquid substance that is preferably applied by a digital ink head.

The liquid substance may be water based.

The surface 2 with the bonded colourants 7 may be heated and pressed.

The surface 2 and the colourants 7 may be pressed and cured to a hard surface with an embossed structure.

The colourants 7 may be macro colourant particles larger than 20 microns and they may be pressed into the surface 2.

The surface 2 may be a part of a panel 1 that may be a laminate or wood floor, a powder based floor, a tile or a LVT floor.

The liquid blank ink may be replaced with a digital heating process where heat from a digital heating print head or a laser activates a binder included in the dry ink and/or in the surface.

The blank ink and the dry ink may be applied in many alternative ways. The surface 2 may point upwards or downwards and the blank and/or the dry ink may be applied from above or from below. A surface 2 with blank ink may, for example, point downwards and may be brought into contact with a dry ink layer. Non-bonded dry ink may be removed by gravity when the surface is separated from the dry ink layer. In order to simplify the description, the majority of the preferred embodiments show a surface pointing upwards and attached to a panel prior to printing. Separate surfaces 2 without a supporting panel 1 may be printed according to the principles of the invention.

The method is particularly suitable in applications where considerable quantities of colourants, preferably pigments, are applied on a large flat panel in order to form an advanced large print or decorative pattern with preferably high wear, impact and UV resistance and where the pattern preferably is intended to copy a wood or stone design. Such designs are generally formed with one base colour that, for example, gives the wood or the stone the basic appearance and a few spot colours that are used to form the wood grain structure, knots, cracks and various defect which are visible in the wood surface or crystal structures cracks and other defects in a stone design. The method is also very suitable to form a pattern on a tile or to print laminate and powder based floors with a copy of, for example, a tile floor that comprises tiles with different colours and grout lines between the tiles.

Contrary to known methods, the digital ink head, hereafter referred to as "digital drop application head" 30', is not used to apply any type of conventional ink with colour pigments or dyes. This is an advantage since no expensive inks comprising pigment dispersions and binder resins have to be handled by the digital drop application head 30'. The blank ink is preferably an essentially transparent liquid substance that preferably mainly comprises water.

The blank ink, also called liquid substance, comprises preferably no pigments.

A print provided by the blank ink or liquid substance may be referred to as a liquid print P. The liquid print may be formed of drops of the blank ink applied on the surface.

The colourants are preferably bonded to the surface in two steps. The first bonding is an application bonding where the bonding of the colourants should be sufficient to keep the colourants connected to the binder pattern BP in order to allow the remaining excessive colourants that have been applied on areas outside the binder pattern, to be removed.

The second bonding is a permanent bonding intended to connect permanently the application-bonded colourants to the surface 2.

The first application bond and the second permanent bond may comprise an intermediate stabilization step where the structure of the bonded colourants are modified by, for example, heat and/or pressure such that a new print forming cycle may be made. The intermediate stabilization step allows that the new non-bonded colourants that are applied on the surface during a second print forming cycle may be easily removed even on surface parts that comprise colourants from the first print forming cycle.

The first application bonding is preferably obtained with a liquid substance, also referred to as blank ink, that preferably mainly comprises distilled or deionized water. The adhesion of water may in some application, especially when only one colour is applied, connect the colourant to the surface with a force that is sufficient to allow removal of the non-bonded colourants. The production costs for such a liquid substance are extremely low and clogging of the nozzles when a binder dries may be avoided. Some chemicals may be added, for example glycol or glycerine, that are needed to reach the viscosity and surface tension of the liquid substance that may be needed for a proper function of a print head. Water-soluble polyethylene glycol (PEG), that is available in many different molecular weights, is especially suitable to modify water such that a blank ink with an appropriate viscosity that works, for example, with Piezo heads may be obtained. Low monocular weight formulations such as, for example, PEG 400 are especially suitable to use in blank ink and preferably together with dry ink or a surface that comprises thermosetting resins such as melamine. Water and PEG are compatible with melamine resins and allows easy and fast curing when heat and preferably also pressure is applied. A preferred nondrying solvent that is compatible with thermosetting resins should be miscible with water, have a boiling point above 100° C. and a melting point lower than the application temperature. Examples of such, but not restricted to, are ethylene glycol, propylene glycol, polyethylene glycol, diethylene glycol, butane diol and glycerine. Combinations can also be used. In some applications some other minor amounts of chemicals may be included in the blank ink, for example, wetting agents and other chemicals that are needed to prevent bleeding when the blank ink is applied on a surface. The blank ink may also comprise release agents, especially when a direct application of the colourants, hereafter referred to as "direct BAP printing" as described above is replaced by a transfer application hereafter referred to as "transfer BAP printing" where the blank ink and colourants are in a first step applied on a transfer surface and then pressed against and bonded to the surface. Most such additives are cost efficient and the blank ink may have a production cost which is a fraction of the costs for conventional pigment based inks.

Most Piezo print heads are designed to work with a viscosity in the range of 2 to 12 centipoise (cps). The water based blank ink may easily be adapted to meet all possible viscosity requirements.

A suitable blank ink that preferably may be used in a low viscosity print head designed to operate with a viscosity of about 5 cps such as a Kyocera print head may be a water based glycol solution comprising, for example, about 75% (weight) Ethylene Glycol or 55% Diethylene Glycol or 50% Propylene Glycol or 38% Polyethylene Glycol PEG 400. A water based glycerine solution comprising about 40% glycerine may also be used. De-ionized water may also be mixed with Glycerine and Glycol. A suitable blank ink for a low viscosity print head may, for example, comprise about 40% water, 50% Glycerine and 10% Diethylene Glycol.

A suitable blank ink that preferably may be used in a high viscosity print head designed to operate with a viscosity of about 10-12 cps such as a Fuji print head may be a water based Glycol solution comprising, for example, about 95% (weight) Ethylene Glycol or 75% Diethylene Glycol or 70% Propylene Glycol or 50% Polyethylene Glycol PEG 400. A water based Glycerine solution comprising about 65% glycerine may also be used. De-ionized water may also be mixed with Glycerine and Glycol. A suitable blank ink for a high viscosity print head may, for example, comprise about 30% water, 60% Glycerine and 10% Diethylene Glycol.

The water content for blank ink adapted for low and high viscosity Piezo print heads may be increased further if high viscosity glycols are used; for example, Polyethylene Glycol with a higher molecular weight than PEG 400. A preferred blank ink that preferably is suitable for Piezo print heads may comprise 0-70% water and 30-100% Glycol and/or Glycerine. Even more preferred is a formulation comprising 10-70% water and 30-90% Glycol and/or Glycerine. Blank ink that is suitable for thermal bubble jet print heads that are designed for very low viscosities; for example, 2-4 cps may comprise more than 70% water.

All blank ink formulations may comprise small amounts, about 1%, of wetting agents such as BYK or Surfinol and chemicals such as Actidice intended for control of bacteria and fungi.

The blank ink is preferably essentially a non-curable liquid substance that is used to obtain the application bonding and to bond the colorants until the final permanent bonding takes place preferably with heat and pressure and with resins that are a part of the substrate material and/or the dry ink particles. Such blank ink will not bond particles when it dries or when heat is applied.

The blank ink may comprise special curable binders, preferably water based acrylic emulsions, which are compatible with water, glycol or glycerine. Preferable binder content is 5-20%. Acrylic emulsions will bond particles when the water content evaporates and they will create a strong bond under high heat and pressure.

A high water content of at least 50% gives the advantages that the material cost may be low. The decap time will be rather short, less than one hour, since water evaporates. A low water content combined with a high glycol or glycerine content will increase the decap time considerably. Blank ink with a water content below 40% may have a decap time of several hours. Water content below 20% will give a very long decap time that may exceed 6 hours. It is possible to use blank ink that comprises more than 90% glycol and this may increase the decap time to several days. Blank ink may be made without water and high viscosity print heads may handle blank ink that comprises, for example, 100% Ethylene Glycol.

An ink circulation system may be avoided in industrial printers when blank ink is used that does not comprise any pigment dispersions or binders and that is mainly a water based solution as described above. This will decrease the cost for the printing equipment considerably.

Figure 2E:
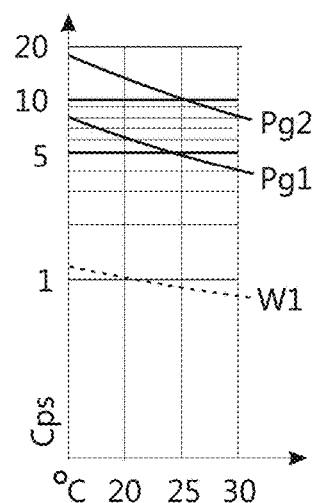

FIG. 2e shows viscosity in cps of aqueous Propylene Glycol (PG) solutions in temperatures 20-30° C. W1 shows viscosity of water. Pg1 comprises 50% PG and 50% water. Pg2 comprises 70% PG and 30% water. Viscosity of blank ink adapted for a low viscosity print head may vary between 4-6 cps within the temperature range of 20-30° C. The viscosity of blank ink adapted to high viscosity print heads may vary between 8-14 cps and this may be outside the normal working conditions of the print head. This problem may be solved with printing equipment that comprises a temperature control system that preferably is combined with a climate control system that controls the humidity. Decap time for water based blank ink may be increased if the relative humidity around the print heads is above 50%.

The binder that bonds the colourants to the surface may comprise two components. The first binder component may be included in the blank ink. The second binder component may be included in the dry ink or the surface and activated by the blank ink. This makes it possible to use, for example, water in order to obtain the application bonding, stabilization and permanent bonding. Water may react with a binder that may be included in the colourants or in the surface. The blank ink may of course comprise a binder that may provide the same bonding as the two components mentioned above.

The blank ink may be applied on any surface 2, for example, a non-transparent paper layer, an essentially transparent overlay, a powder layer, a stabilized powder layer, a wood veneer or wood sheet, a tile glazing, a plastic foil or a base colour applied on a sheet shaped material preferably comprising wood or polymer material.

The application of the surface 2 to a sheet shaped material such as a panel 1 gives several advantages. Handling and positioning of loose layers that may swell and shrink during the application of liquid blank ink may be avoided. The application bonding of the colourants 7 may be made with a very low bonding strength since the surface 2 is supported by the flat panel and may be displaced horizontally on a conveyor directly into a press where the permanent bonding with heat and pressure takes place. Rolling, cutting and stacking of paper and foil surfaces may be avoided. Some surfaces such as uncured powder and tile glazing cannot be handled without a support of a panel 1.

BAP printing on LVT floors may also be made when, for example, the individual base layers, preferably including a glass fibre layer, and a decorative plastic foil with a base colour are fused together to a panel. A transparent protective layer may be fused with heat and pressure on the BAP print and the decorative plastic foil such that the dry ink particles are permanently bonded and fused to the surface. The blank ink may be adapted such that floating of the drops on the smooth plastic foil is avoided. It is an advantage if the blank ink has a high viscosity, preferably 10 cps and higher.

BAP printing on ceramic tiles is preferably made when the powder is pressed to a tile body forming a panel. A glazing with a preferably base colour is applied on the tile and a BAP print is applied on the dry glazing. The BAP print and the tile body is thereafter pressed and a protective transparent glazing is applied on the pressed print. The tile is after glazing fired in a furnace or kiln at very high temperatures such that the dry ink particles cure and melt into the tile body and the glazing.

Embodiments described above are based on the main principles that the BAP print is applied on a surface 2 that forms a part of a panel 1 and that also comprises a material composition such that when heat and pressure is applied, the panel, the surface and the print will be permanently bonded together. Such surfaces may comprise thermosetting resins, preferably melamine formaldehyde resins which generally are used in WFF or paper based laminate floors, curable and fusible mineral materials used in ceramic tiles, or thermoplastic materials used in LVT floors.

Direct and transfer BAP printing may also be used on textile surfaces. Dry ink and blank ink may be specially adapted for various textile surfaces. Binders, dry ink viscosity and the size or the colourants may be adapted to provide an appropriate bonding and removal of the colourants.

Application on some specific surfaces may be improved by a so-called corona treatment, sometimes also referred to as air plasma. This is a surface modification technique that uses low temperature corona discharged plasma to impart changes in the properties of a surface. The corona plasma is generated by the application of high voltage to sharp electrode tips, which forms plasma at the ends of the sharp tips. Materials such as plastics, glass or paper may be passed through the corona plasma curtain in order to change the surface energy of the material. The surface may also be treated with various types of mineral salts.

The surface may comprise a first base colour, which may be used to create a major part of the coloured visible surface. Powder based surfaces, preferably comprising thermosetting resins, may be pre-pressed and formed with a smooth surface that facilitates the application and removal of the colourants. The pre-pressing is preferably made with pressure and heat and during a press cycle time that ensures that the melamine resin is in a semi-cured level and in a B stage as described in the introduction.

The colourant comprises, in a preferred embodiment, mainly colour pigments 12 that are scattered as dry powder layer over the wet binder pattern BP as shown in FIG. 2b. The pigments may be mixed with other particles, for example, melamine powder particles 13 that melt when they are in contact with the liquid binder pattern BP and that bond the pigments to the surface. The dry non-bonded pigments and melamine powder 13 may be removed by, for example, an air stream or gravity and the remaining wet melamine 13 and colour pigments 12 form a print P as shown in FIG. 2c which is essentially identical to the binder pattern BP created by the blank ink. Dry ink may have the same material composition as the surface layer 2 in a powder based WFF floor and may comprise a mix of woof fibres, a dry melamine formaldehyde resin powder, aluminium oxide particles and colour pigments.

The stabilization of the print may be partly or completely obtained by, for example, exposure to IR, hot air, UV lights, microwaves, pre-pressing or similar or combinations of such methods. The binder, that in this preferred embodiment is water or wet melamine, is preferably stabilized by pre-pressing that bonds the colour pigments to the surface 2 by drying the wet melamine or by melting the melamine particles. The pre-pressing compresses the surface of the printed pattern P. A second pattern may be printed with the blank ink on the surface 2 and a second layer of pigments and melamine powder may be applied on the surface and over the first print. This may be repeated and an advanced décor may be created with several colours such that the digital image comprises colourants with different colours positioned horizontally offset in the same plane.

The blank ink is preferably an essentially transparent liquid substance that does not disturb the colour of the bonded colourants. Blank ink with the same liquid substance may be used together with dry ink comprising many different colourants and this allows that, for example, one print head with the same blank ink may be used to apply several different colours that may be applied in several steps with an intermediate application of a digital pattern formed by the blank ink. This allows that the number of print heads may be reduced considerably since one print head with one ink channel applying the same blank ink may be used to apply a practically unlimited number of dry inks with different colours, structures particle sizes etc. The simple composition of the blank ink makes it possible to use more cost efficient print heads since no colour pigments are fired through the small nozzles of the print head.

The stabilization step may in some applications be sufficient to create the permanent bonding. The final permanent bonding may also take place when the surface preferably is pressed and cured under heat and pressure according to the methods that are used to cure a laminate or a powder based surface comprising a thermosetting resin or a surface comprising a thermoplastic layer. An UV curing transparent lacquer that is applied over the colourants and that after application is cured in an UV oven may also be used. This transparent layer may be applied in liquid form by rollers or with digital Piezo heads and in one or several steps with intermediate UV curing. A thermoplastic resin or thermoplastic particles may also be used to obtain the first application bond or the second permanent bonding. Paper based or powder based overlay comprising aluminium oxide and melamine resins may also be used as protective layers and as permanent bonding.

The low cost and the simple chemical composition of the liquid substance applied by the drop application head makes it possible to use rather simple digital print head technology to apply the liquid binder substance. CIJ (continuous inkjet) may be used since water is easy to recycle and the collected drops may even be disposed without any recycling. Cost efficient thermal print heads may be used since water is easy to handle with bubble jet technology. Rather simple Piezo heads with high productivity and with DOD (drop on demand) systems may be used that may have a long life time and that require a minimum of maintenance due to the very favorable composition of the liquid substance that will not cause any production disturbance since there are no pigments and preferably no fast drying resins that must be handled, which is the case when conventional pigment based inks are used.

The binder may comprise a wide variety of thermosetting and thermoplastic materials that may be used as particles or chemicals in the surface, in the dry ink or as dispersions in the blank ink applied by the digital drop application head. The majority of such materials may be produced in dry powder form or as liquid dispersions. It is preferred that the chemical substance that provides the bonding after drying is included in the surface or in the dry ink and that the blank ink is a simple liquid chemical substance without any resins or other chemicals that in dry form may clog the nozzles.

As an alternative to thermosetting materials such as melamine or to thermoplastic materials such as, for example, PVC powder, UV cured polyurethane may, for example, be used in powder form or as dispersion.

UV curable polyurethane substance with a viscosity that is adapted to the digital drop application head 30' may be used. Water-based polyurethane dispersions are preferred as a liquid substance in the digital drop application head since they do not cure until they are exposed to UV light. Polyurethane dispersions are fully reacted polyurethane/polyureas of small and discrete polymer particles and such particles may be produced with a size of about 0.01-5.0 microns and may therefore be handled in a digital print head or other similar heads. Polyurethane dispersions may be blended with, for example, acrylic emulsions and other emulsions in order to reduce costs.

The digital drop application head, that in some applications preferably may be a Piezo head, has preferably a capacity to fire drops with a drop size of about 1-200 picolitres or more. The drop size and drop intensity may be varied and this may be used to vary the intensity of a colour and to create a so-called "grey scale" with the same basic colour. Larger drops will bond thicker layers of dry ink and smaller drops will bond thinner layers.

Water based adhesives may also be used such as soluble adhesives or water dispersed adhesives.

Other UV cured materials such as acrylates of epoxy, urethane, polyester, polyether, amine modified polyether acrylic and miscellaneous acrylate oligomers may be used as binders in powder form or as dispersions.

The blank ink may also be applied on a surface by spray nozzles or by engraved rollers.

Figure 2D:
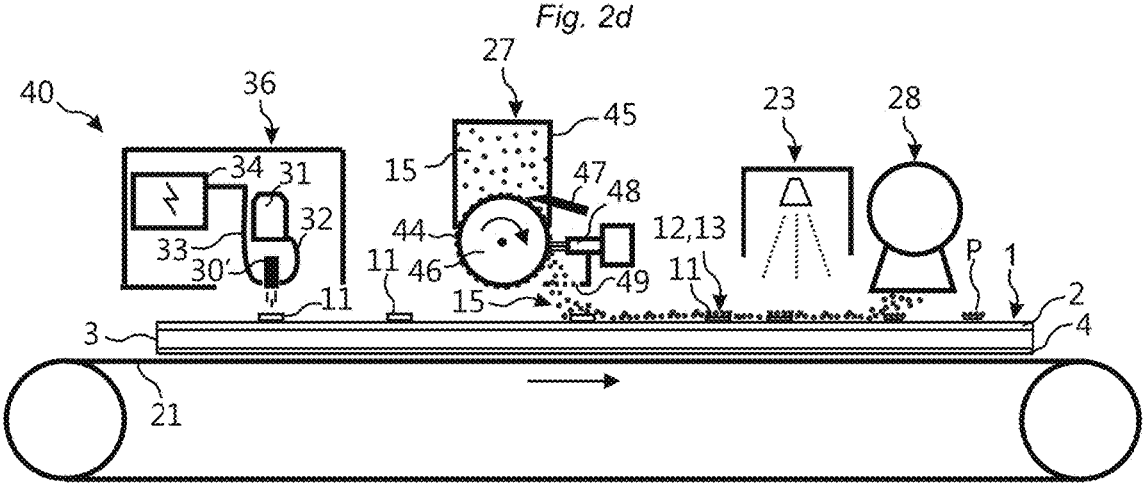

FIG. 2d shows schematically one BAP printing station 40 of a binder printing equipment that may be used to create a digital print P on a panel 1 comprising a surface 2, a core 3, and a backing layer 4. A blank ink application station 36 comprising a digital drop application head 30', that preferably is a Piezo head or a thermal print head, applies a binder pattern BP with blank ink 11. Several heads 30' may be positioned side by side in order to cover the width of the surface that is printed. The binder pattern is created digitally in the same way as in conventional digital printing. The colours are separated and each blank ink application station 36 applies mainly the same liquid substance or blank ink that is used to bond one specific colour in each print forming cycle. The digital drop application head is connected with a feeding pipe 32 to a container 31 with blank ink. The digital drop application heads 30' are digitally connected with preferably data cables 33 or wireless to a digital control unit 34 that controls the application of the drops, the speed of the conveyor 21, the function of a dry ink application unit 27 and all other equipment that is used to bond and remove pigments.

The water based drops of the blank ink 11, which in this embodiment serve as an application binder, should be wet until they pass the dry ink application station 27 that in this preferred embodiment is a scattering station. Dry ink 15, that in this preferred embodiment comprises colourants of colour pigments 12 mixed with a resin of spray dried melamine powder 13, is scattered on the liquid blank ink 11.

The scattering equipment comprises a hopper 45 that contains dry ink 15, a doctor blade 47 that together with a roller 46, preferably comprising an engraved, embossed, etched or sand blasted roller surface 44, acts as a dispensing device that moves a pre-determined amount of dry ink 15 from the hopper 45 and to the surface 2. The roller 46 may also have a roller surface 44 that comprises small needles. Rotating and oscillating rollers may also be used. A material-removing device that may be an oscillating or rotating brush 48 may also be used in some applications together with one or several rotating or oscillating meshes 49 that may oscillate or rotate in different directions.

The doctor blade 47 may be rigid or flexible and may have an edge that is adapted to the structure of the roller surface. The oscillating or rotating meshes 49 may also be formed such that they spread the dry ink 15 in a pre-defined way and they may be combined with one of several nets that may be used to sieve the particles before they are applied as a layer. The rotation of the roller, the position of the doctor blade and the speed of the surface that is intended to be covered with the dry ink may be used to control the layer thickness.

The liquid blank ink 11 and the dry ink with pigments 12 and melted melamine particles 13 is in this embodiment heated and stabilized when it is displaced under preferably a hot IR lamp 23, which is located preferably after the digital drop application head 30' in the feeding direction.

A dry ink removal station 28, that in this embodiment is based on air streams and vacuum, removes pigments 12 and melamine particles 13 that are not wet and not bonded by the binder pattern BP and a perfect colour print P is provided. The dry ink removal station may be located after the IR lights 23 or between the IR lights and the scattering station 27. This production step may be repeated and a second scattering station 27 that comprises another colour may apply a second colour on a binder pattern that may be applied by the same print head or a new print head that is used in a second print forming cycle. The removed dried pigments and melamine particles may pass through a sieve or a filter and they may be recycled and reused again several times.

The panel 1 with the surface 2 is preferably displaced essentially horizontally under the digital drop application head 30', the dry ink application station 27 and the dry ink removal station 28 with one or several conveyors 21. It is obvious that the digital drop application head 30', the dry ink application station 27 and the dry ink removal station 28 may alternatively be displaced over a panel 1 during the BAP printing.

The dry ink may in addition to pigments and melamine particles also comprise wear resistant particles, such as small aluminium oxide particles, and fibres, preferably wood fibres, that preferably may comprise or consist of bleached transparent or semi-transparent fibres. Such dry ink may be used to create a solid print with pigments that are positioned vertically above each other with binders and wear resistant particles above and below the pigments. Small drops of blank ink may due to capillarity and the combination of surface tension and adhesive forces penetrate into the dry ink and bond larger amounts of dry ink than an application with conventional ink where pigments are applied as small drops on a surface.

A preferred embodiment of BAP printing is characterized in that the vertical extension of the colourants exceeds the vertical extension of the blank ink drops. Another preferred embodiment is characterized in that the digitally applied blank ink drops penetrate downwards and upwards from the surface after application. A very wear resistant print may be obtained with a printing method comprising blank ink and dry ink with wear resistant particles preferably incorporated in the dry ink.

Several layers of prints may be position above each other and this may be used to increase the wear resistance further and to create 3D decorative effects.

Static electricity or ultrasound may be used to apply and/or to remove the non-bonded powder particles. Air-streams and vacuum that blows away and/or sucks up particles may preferably be combined with brushes. In general, all dry and wet methods that are used to remove dust may be used separately or in various combinations to remove the non-bonded parts of the dry ink. However, dry and non-contact methods are preferred.

A controlled complete or partial removal of the non-bonded dry ink particles is essential for a high quality print with a pre-defined decorative image. Advanced removal systems may also be used that only removes the colourants, for example, colour pigments while an essential part of the transparent melamine powder particles may remain on the surface. This may be accomplished by, for example, a two-step application where a first layer comprises only melamine resin or particles that are applied to the surface prior to the application of the blank ink with the colourants. This first layer is preferably stabilized. It may be sprayed with water and dried by, for example, IR or hot air. This separate binder layer that preferably comprises melamine may in some applications replace, for example, pre-impregnated paper, that in some application may be used as a surface layer 2, and only non-impregnated paper with or without a base colour may be used as a surface 2 for the print application cycle.

The moisture content of the surface layer should be accurately controlled in order to facilitate the removal of the non-bonded powder particles. Moisture content below 8% or even more preferably not exceeding 6% is preferred. The surface layer 2 may be dried by, for example, IR lamps prior to the application of the blank ink. Special chemical may be applied in order to seal the surface 2 or the upper part of the bonded colourants in order to create a sealing or a release layer that may prevent colourants to stick to specific parts of the surface layer where no blank ink is applied.

The floor panel 1 comprises generally a lower balancing layer 4 of laminate, plastic foils, coated paper or like material. Such balancing layer may also be applied as a dry mix of melamine powder and wood fibres, which are stabilized by moisture and heat prior to pressing. Pigments may be included in the powder mix to provide a base colour. The balancing layer may also comprise only melamine powder or a liquid melamine resin, which is applied directly on the rear side of the core 3, and no paper or wood fibres are needed to balance the surface layer. The melamine content in the surface layer is preferably higher than in the balancing layer. The rear side of the panel is very suitable to provide specific information to the floor installer or end consumer. Conventional digital printing or BAP printing may be used to create a digital pattern or text on the balancing layer. Installation and maintenance instructions, logos, other type of instruction, pictures and information may be included and may replace information that is generally applied on the packaging or in special separate instructions. The digital print and especially the BAP print may be very cost efficient since only one digitally applied colour is generally sufficient in addition to a base colour. The backing layer may also have a digital print that is only decorative.

FIGS. 3a-3d show an embodiment of the invention, which is based on a second principle where dry ink 15, comprising colourants 7 and preferably also a binder that may be melamine 13, in a first step is applied on a surface 2. A digital print is thereafter as a second step formed by the digital drop application head that applies a blank ink pattern BP by means of the blank ink on the dry ink. A main difference between the first and the second principle is the sequence of application of the blank ink and the dry ink. The blank ink 15 is according to the first principle applied in a first step while according to the second principle the blank ink 15 is applied in a second step. The first principle is below referred to as "Binder Under Powder" BUP printing and the second principle is referred to as "Binder On Powder" BOP printing. The BUP and BOP digital print may be a direct print or a transfer print as described above.

These two principles BUP and BOP may provide different images with different colour intensity. The blank ink drops 11 will when applied according to the first BUP principle form ink spots when they hit the surface and such ink spots will cover a much larger area than the diameter of the drops. Only a part of the liquid substance from the ink spots will penetrate from the surface and into the dry ink. When the blank ink drops are applied according to the second BOP principle, they will first penetrate into the dry ink particles that will be bonded together in small particle clusters and a smaller part of the liquid blank ink drops will reach the surface 2 where the small clusters will be bonded to the surface.

Such application may be used to prevent bleeding in some application where the surface has an open structure that distributes a liquid substance. It should be mentioned that bleeding is not always a disadvantage since it may be used to create decorative effects. The application of dry ink must be accurately controlled when the BOP principle is used and the maximum thickness of the dry ink layer should be adapted to the drop size and drop intensity such that the blank ink penetrates through the dry ink layer and to the surface. The thickness of the dry ink layer should preferably not exceed the maximum penetration level of the dry ink drops.

The thickness of the dry ink layer may vary considerably when the first BUP principle is used since excess non-bonded particles above the penetration level of the blank ink drops applied on the surface will automatically be removed and liquid substance on the upper part of the dry ink particles may be dried. The thickness of the dry ink layer may be larger or smaller than the penetration level of the blank ink drops when the BUP principle is used. This provides the possibility to use combinations of blank ink drop intensity and vertical extension of the dry ink to create colour variations.

Both principles have advantages and disadvantages depending on application.

Figure 3A:
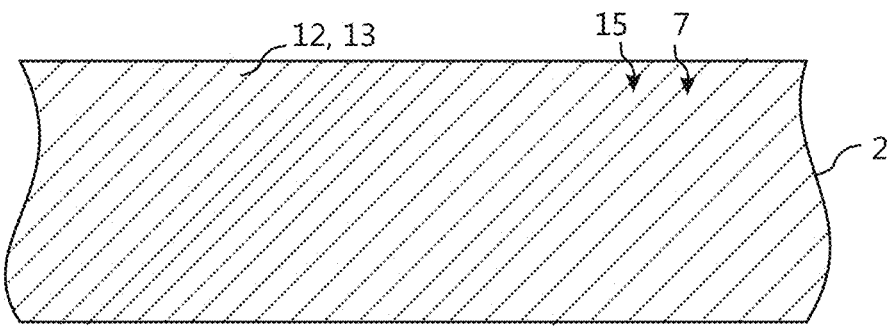
FIGS. 3a-d Illustrate a second principle of an embodiment of the invention.
Figure 3B:
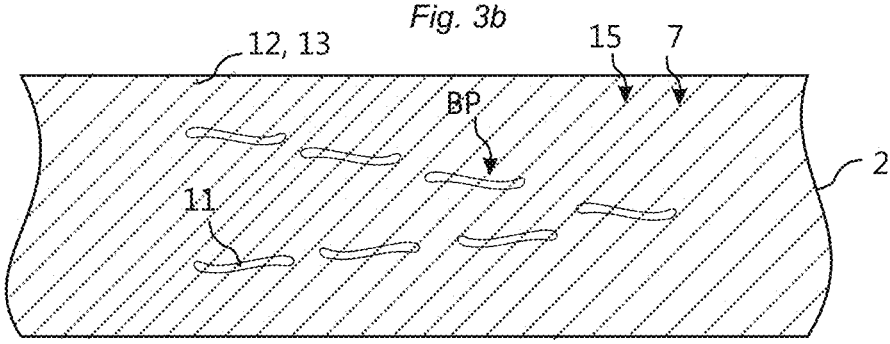
Figure 3C:
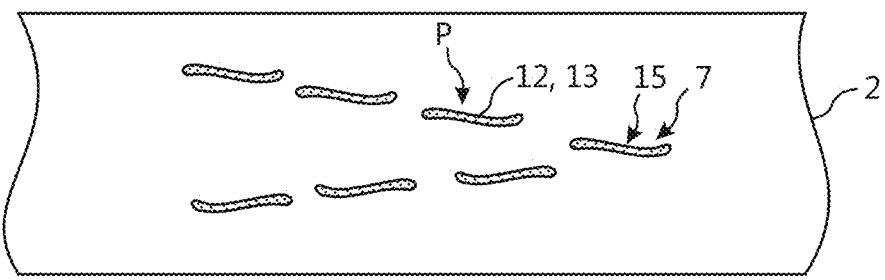
Figure 3D:
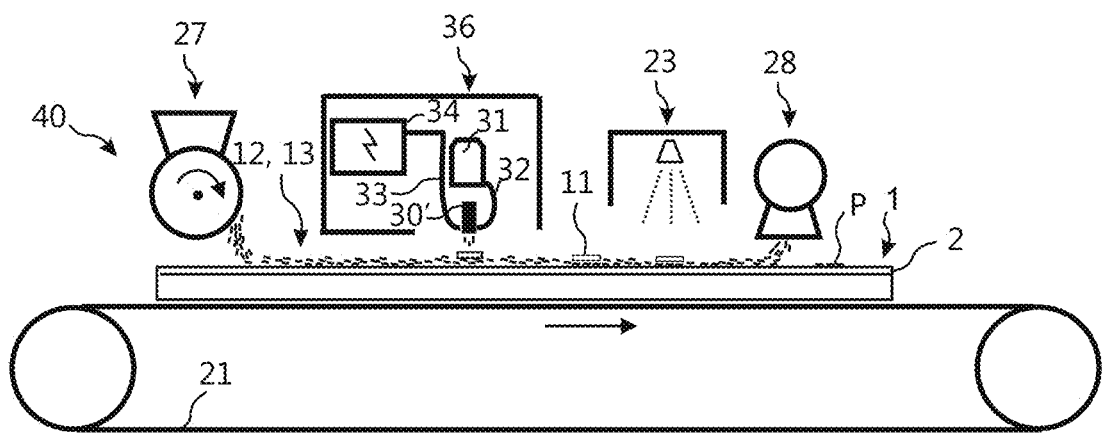

The blank ink 11 may even in this embodiment comprise water that when applied melts, for example, melamine particles 13 mixed with pigments 12 or melamine particles applied under the pigments. The binder connects some pigments that form the same patter as the binder pattern BP while other non-bonded pigments are removed. FIG. 3a shows dry ink 15 comprising a mix of melamine powder 13 and pigments 12 scattered on a surface 2. FIG. 3b shows a digitally applied blank ink pattern BP applied on the dry ink. FIG. 3c shows that non-bonded pigments and in this preferred embodiment also melamine particles 13 have been removed. FIG. 3d shows a BAP printing station 40 comprising a scattering station 27 a blank ink application station 36, an IR oven 23 and a dry ink removal station 28 based on an air stream and vacuum.

The first and the second principles may be combined. Blank ink 11 may be applied prior and after the application of the dry ink 15 and this may be used to bond a thicker layer of colourants and to create a solid print with a large vertical extension and high wear resistance. Binder printing equipment may comprise binder-printing stations that apply dry and blank ink according to the first and the second principle.

Figure 4A:
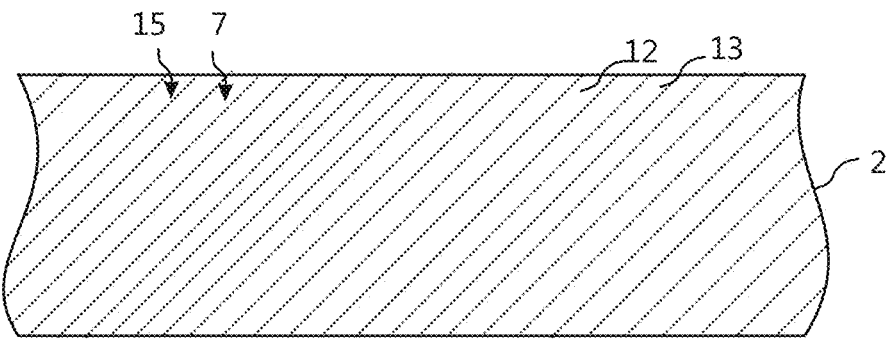
FIGS. 4a-d Illustrate a third principle of an embodiment of the invention.
Figure 4B:
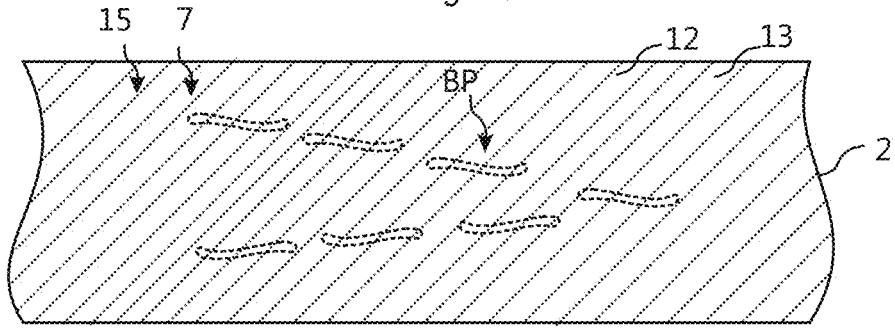
Figure 4C:
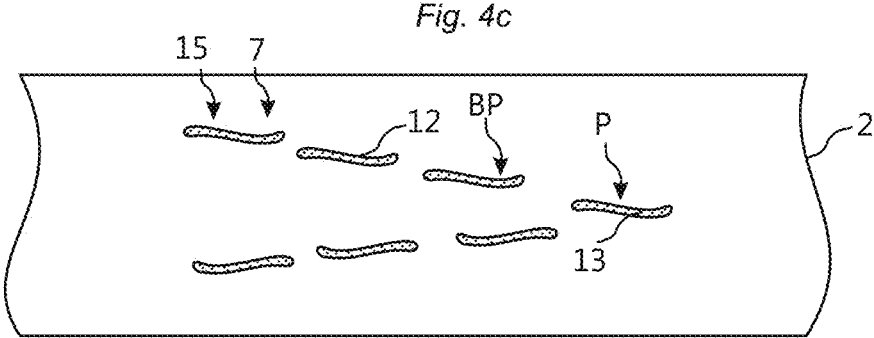
Figure 4D:
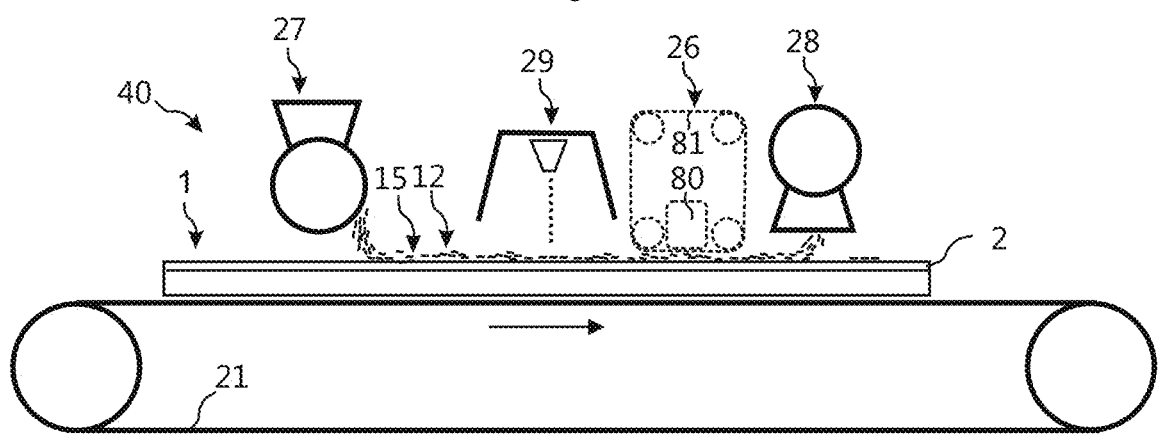

FIGS. 4a-4d show embodiments of the invention, which are based on a third principle where the bonding of the dry ink 15 is accomplished with digitally controlled heat that activates a heat sensitive resin and bonds the dry ink 15 to a surface 2 such that a digital print P is formed when non-bonded dry ink particles are removed. Dry ink 15 comprising colourants 7, preferably pigments 12, may in a first step be applied on a surface 2 as shown in FIG. 4a. A binder pattern BP or image is thereafter formed digitally by dry methods and non-bonded colourants 7 are thereafter removed as shown in FIG. 4c. Several methods may be used. FIG. 4d shows a laser beam 29 that melts or cures a binder, for example a thermosetting or thermoplastic resin 13 that may be mixed with the blank ink or included in the surface 2. The dry ink may also be connected electrostatically to the surface by the laser beam. A digitally created print P is obtained when the non-bonded or non-connected colourants, are removed. The laser beam may be used to create a binder pattern with heat or electrostatically prior and/or after the application of the colourants according to the first and the second principles described above for the application of the blank ink.

FIG. 4d shows a binder printing station 40 comprising a dry ink application station 27, a laser 29 and a dry ink removal station 28 based on an air stream and vacuum. The laser 29 may be replaced with heating lamps that may be used to create images that comprise, for example, rather large areas of the same colour as in some stone designs or base colours in wood grain designs.

FIG. 4d shows also that a heat bonding station 26 with heating print heads 80 comprising several small heating elements may be used to create high-resolution prints with dry bonding methods. The heating print head 80 may apply direct heat that bonds dry ink 15 particles preferably comprising pigments 12 and a heat sensitive resin. The heating print head 80 may also apply indirect heat by heating a heat transfer foil 81 that may be in contact with the heating print head 80 and the dry ink 15 particles. The heat transfer foil 81 may be a copper or aluminium foil and may comprise individual small elements with high thermal conductivity, for example, elements made of copper or aluminium, that are imbedded in a heat insulating carrier that prevents heat to spread between individual elements. The heat transfer foil 81 may be used to increase the printing capacity. A heat pulse from the heating print head will heat a portion of the foil and the heat will be maintained when the foil follows the surface and transfers the heat to the dry ink particles.

Even a conventional laser system based on the above described impact method may be used to apply a digital print partly or completely on a building panel or in combination with the above described binder printing methods.

All the above-described principles may be partly or completely combined and a production line may comprise several digital binder printing station according to the first, second or third principles.

Figure 5A:
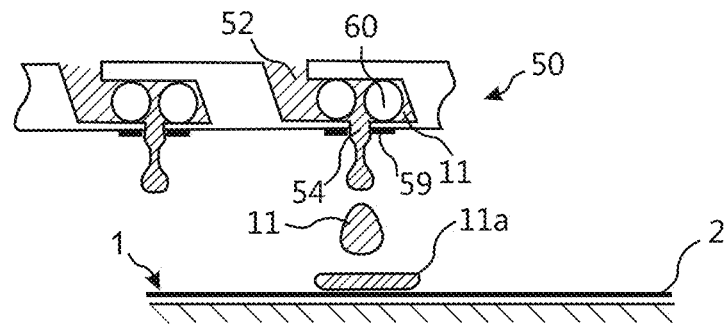
FIGS. 5a-h Illustrate digital application of pigments according to the first principle of an embodiment of the invention.

FIGS. 5a-5h show schematically side views of application of two different colours according to the first BUP principle. A first binder or a spot of blank ink 11a, that in this embodiment comprises essentially water, is applied by a thermal digital drop application ink head on a surface 2 that may be a stabilized powder layer or a paper as shown in FIG. 5a. The jets 50 from the head apply drops of blank ink 11 by the nozzles 54 when the heater 59 creates bubbles 60 in the ink chamber 52 such that the blank ink drops 11 form liquid spots 11a when they hit the surface 2. The digital drop application head may also be a Piezo head and the water based blank ink may also comprise a viscosity increasing substance. The water based blank ink may comprise glycol or glycerine.

Figure 5B:
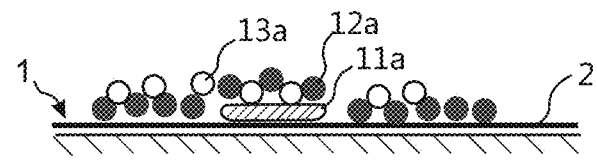
Figure 5C:
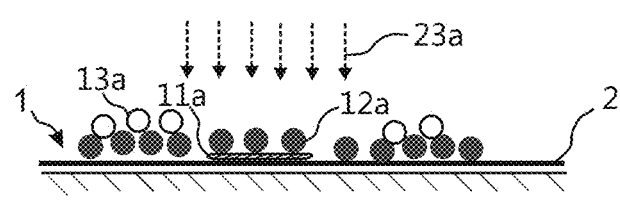
Figure 5D:
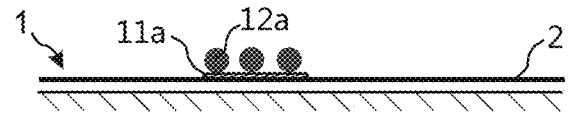
Figure 5E:
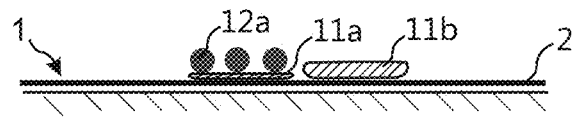
Figure 5F:
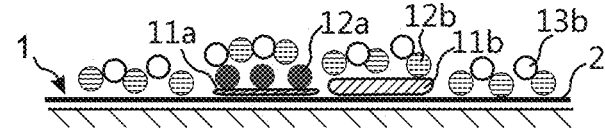
Figure 5G:
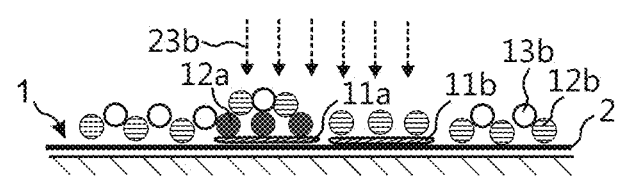
Figure 5H:

A first dry ink layer comprising colour pigments 12a and dry particles of a binder, in this preferred embodiment melamine particles 13a, is applied on the surface 2 and on the liquid blank ink spots 11a as shown in FIG. 5b. Melamine particles 13a that are in contact with the wet water based drops will melt. A first IR lamp 23a may be used to dry the wet melamine and to bond the pigments to the surface as shown in FIG. 5c and the non-bonded melamine and pigment particles are thereafter removed such that a pigment image or décor 12a that corresponds to the applied binder pattern formed by the blank ink drops 11a is obtained as shown in FIG. 5d. FIGS. 5e-5h show that the same application may be repeated with a new application of dry ink comprising pigments 12b having another colour and mixed with melamine particles 13b and a new binder pattern 11b such that a two colour image is obtained with two types of colourants or colour pigments 12a, 12b bonded to two patterns of blank ink 11a, 11b as shown in FIG. 5h.

Figure 6A:
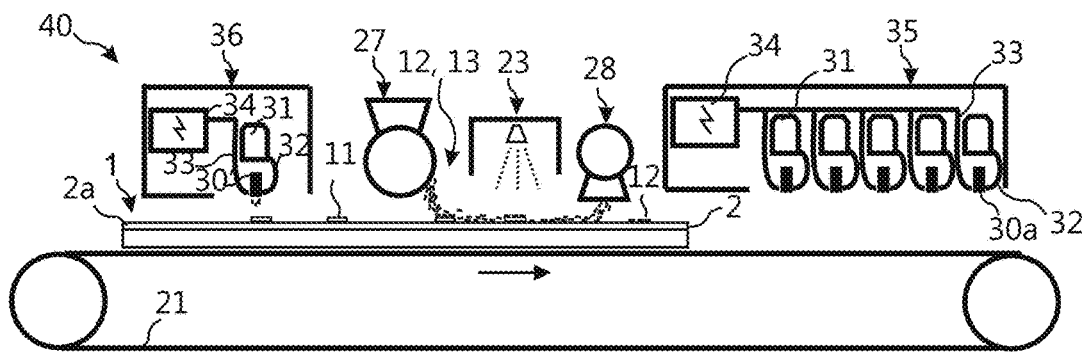
FIGS. 6a-d Illustrate production methods based on the first principle of an embodiment of the invention and a panel with a decorative pattern formed according to an embodiment of the invention.

FIG. 6a shows an embodiment where the digital BAP printing equipment 40 comprises a digital blank ink application station 36, a dry ink application station 27, IR drying or curing 23 and a dry ink removal vacuum station 28. The BAP printing equipment 40 is in this preferred embodiment combined with a conventional ink jet printer 35. The BAP printing method may be used in this combination to create the major part of a digital print while some parts of the final print may be created by a conventional ink jet printer. This may reduce the ink cost considerably since, for example, the cost effective BAP method, where no pigments have to be handled by the digital drop application head, may apply, for example, 90% of the pigments which are needed to create a fully printed digital décor or pattern. Powder based floors are particular suitable for this combined method. A first base colour may be provided by the powder layer 2a. A second coloured pattern may be applied by the BAP printing equipment and a third colour may be applied by conventional digital printing equipment. No stabilization of the second colour is needed since no additional dry colourants will be applied and removed. This embodiment is characterized in that a three-colour image is formed by a base colour, preferably included in powder or in a paper layer, dry colourants and liquid ink. The same type of print heads may be used to apply the blank ink and the conventional liquid ink.

A conventional digital printer may be used to apply blank ink that is used as binder for the dry ink and a conventional liquid ink comprising colourants. One or several ink channels may, for example, be filled with blank ink that has different drying and/or bonding properties than the other channels comprising conventional pigment based ink. The blank ink drops may be wet when the pigment-based drops have dried. The blank ink may be used to apply colourants that form the major parts of the colour of a digital print.

Figure 6B:
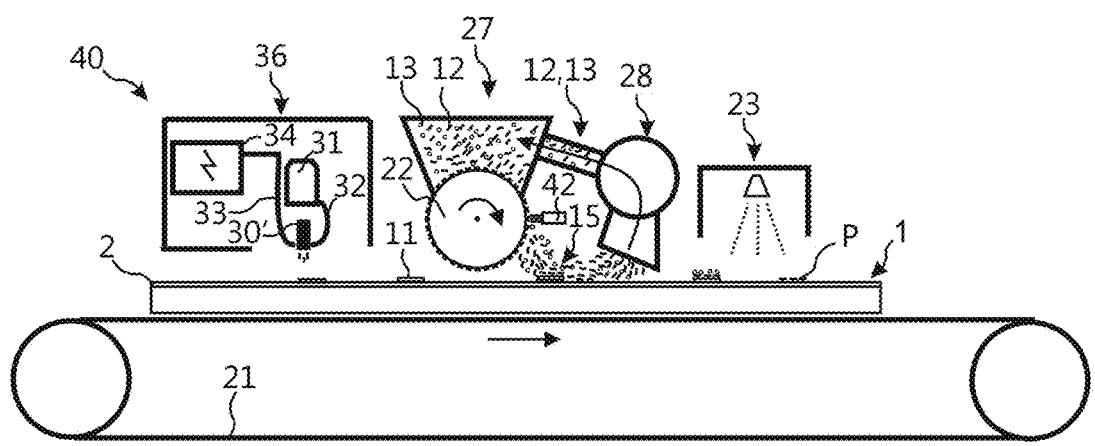

FIG. 6b shows a binder and powder printing equipment 40 where dry ink 15, comprising, for example, a mix of pigments 12 and melamine powder 13 is applied by a scattering station 27 comprising preferably an embossed roller 22 and preferably an oscillating brush 42. The non-bonded colourants, for example, pigments and melamine particles are removed by a dry ink removal station 28 that recycles the mix 12, 13 or the blank ink into the scattering station 27. A pigment/melamine dust cloud may be created by airstreams and only the pigments and melamine powder that come into contact with the wet binder 11 will be bonded to the surface 2.

Figure 6C:
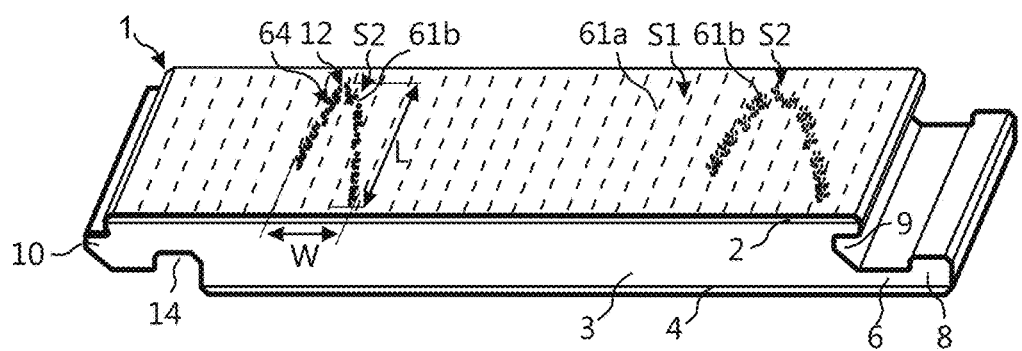

FIG. 6c is a cross section of a floor panel 1 and shows that the BAP printing method is especially suited to apply a digital BAP print on a floor panel with a paper based or powder based surface 2 and with a mechanical locking system comprising a strip 6, with a locking element 8 in one edge that cooperates with a locking groove 14 in an adjacent edge of another panel for horizontal locking of the adjacent edges and a tongue 10 in one edge that cooperated with a tongue groove 9 in another edge for vertical locking of the panels.

Such floor panels have generally advanced embossed wood or stone decors that require large amounts of different colour pigments and a decor that has to be positioned accurately in relation to embossed structures and the panel edges where the mechanical locking system is formed. Generally the décor must be adapted to the edge part of the surface portion that is removed when the locking systems are formed. FIG. 6c shows a wood grain pattern with a first S1 and a second S2 surface portion having different colours. The second surface portion S2 that in this embodiment extends mainly in the length direction L of the floor panel is applied on a basic layer 2 comprising the first surface portion S1.

Figure 6D:
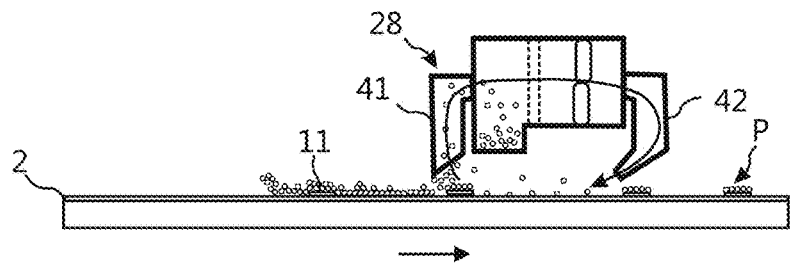

FIG. 6d shows a dry ink removal station 28, that in this embodiment is based on air streams and vacuum that blow away and sucks up particles. One or several vacuum-sucking profiles 41 with openings that cover the whole width of the applied dry ink layer may be used to remove essentially all non-bonded dry ink particles 11. One or several air knifes 42 that also cover the whole width may applies an air pressure on the remaining non-bonded particles such that they are released from the panel surface 2 and blown into the vacuum—sucking profile. The major advantage with this combined method is that high air pressure is more efficient and creates a stronger air stream than vacuum. This method may be used to remove essentially all visible dry ink particles from rough surfaces such as a stabilized powder surface and rough paper surfaces. Even very small particles, for example, small pigments or very small wood fibres may be removed. A two-step process may be used to recycle dry ink. A first removal is made with a dry ink removal station that only comprises a vacuum-sucking device and that removes all very loose particles, which may be about 90% or more of the non-bonded dry ink particles. Such particles are generally very clean and may be reused. A second combination dry ink removal station 28 based on vacuum and air pressure as shown in FIG. 6d may be used to remove the remaining particles that may contain some particles from the powder based surface 2 or from a precious application of another colour. Such particles may not be suitable for a recycling.

All the above-described methods may be partly or completely combined.

Figure 7A:
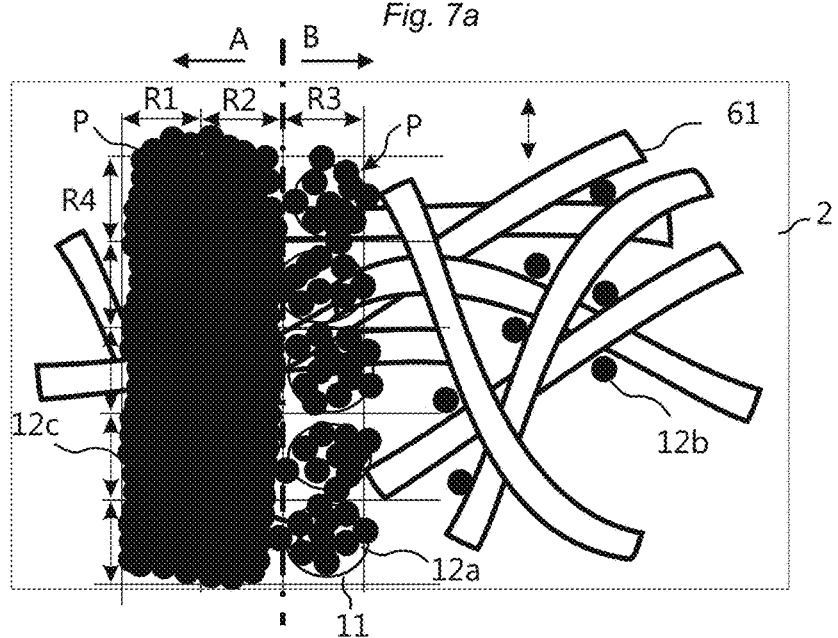
FIGS. 7a-c Illustrate application of colourants on a surface.
Figure 7B:
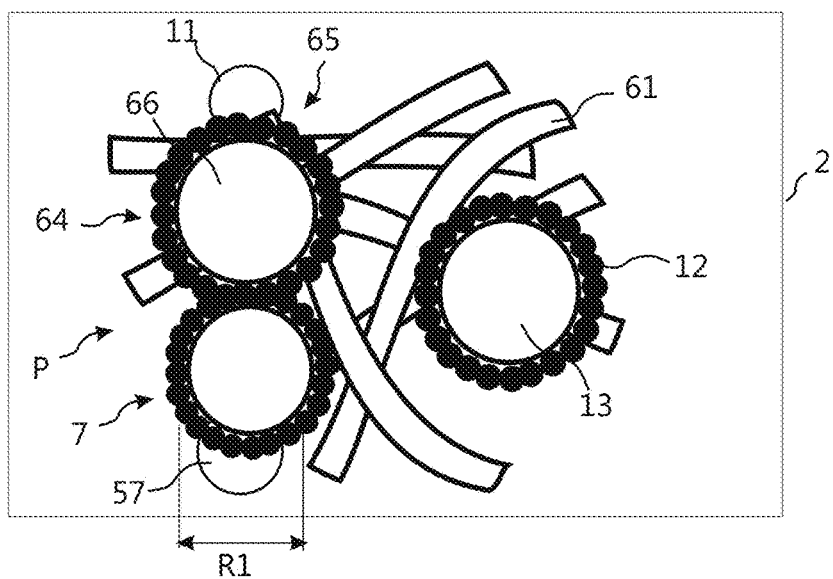
Figure 7C:
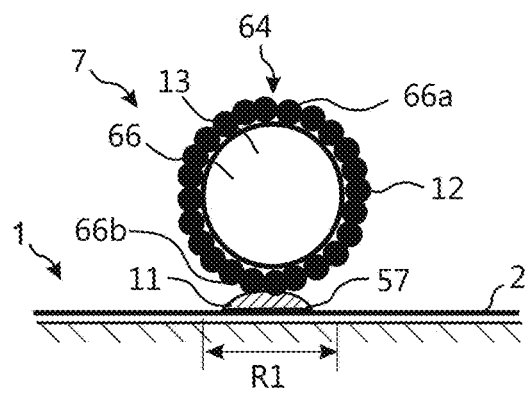

FIGS. 7a-7c describes application and removal of colourants 64 having different sizes and how a solid print P may be formed by pressing together dry ink 11 particles.

Application and removal of colourants are, in some applications, important for a high quality image. In some other application it may be an advantage if some colourants are left on the surface since this may be used to create a more realistic copy of, for example, wood designs where the wood surface generally always comprises some small defects and colour spots that are distributed in a random fashion. Small particles are also difficult to see and will in many applications not disturb the overall impression of the décor, especially if they are not applied in a raster pattern.

FIG. 7a shows that very small particles with a size of 10-20 microns and smaller may have a tendency to stick to a surface 2 that, for example, may be an uncoated paper surface comprising wood fibres 61 with a rather rough fibre structure. FIG. 7a shows also a pressed part A and an unpressed part B of a panel surface 2. The blank ink drops are applied in a raster pattern R1-R4. The unpressed part B show pigments 12a that after the removal of the dry ink are bonded to the blank ink and other pigments 12b that are not bonded by the blank ink but that are still attached to, for example, paper surface after removal due to friction or static electricity. The pressed part A shows pigments 12c that are permanently bonded to the surface 2 by pressure and heat. Pigments 12c that have been applied above each other are pressed to a flat and solid print P with overlapping pigments. A BAP print provides the possibility to create a print that corresponds to a practically indefinite resolution by using a rather low resolution, for example 300 DPI, when applying the blank ink 11. Such a printed pattern may be practically identical to a wood grain structure in real wood or a stone pattern in a real stone where patterns are formed by different natural fibres or crystal structures.

FIG. 7b shows that the sticking problem may be solved with dry ink that comprises colourants 7 that are larger than, for example, conventional pigments 12. The colourants are preferably in the range of 30-100 microns. In some applications colourants with a size of up to 300 microns or more may be used depending on the décor. Such comparatively large macro colourant particles 64 may be formed in many different ways. The macro colourants 64 comprises according to one preferred embodiment pigments 12 attached to a particle body 66. The particle body is in this preferred embodiment a spray dried melamine particle 13. Such macro colourant particles 64 with a size exceeding 20 microns are much easier to scatter and to remove than small pigments with a size of a few microns or smaller. A advantage is that pigments are attached on several parts of the particle body 66—on lower 66a and upper parts 66b—as shown in FIG. 7c, which is a side view of a macro colourant 64 shown from above in FIG. 7b. A spot 57 of a liquid blank ink 11 bonds a macro colourant particle 64 comprising several pigments 12. The pigments 12 are positioned vertically over each other on opposite sides of a particle body 66 and such embodiment may provide a deeper print with increased colour intensity and wear resistance. Another advantage is that a small blank ink spot 57 may be used to bond a large amounts of colourants or pigments that in fact may have a mass or size that is larger than the mass or size of the blank ink spots applied as drops from a digital drop application head 30'. A large amount of pigment or colourants may be bonded in this way with rather small drops of blank ink. For example one gram of blank ink may bond 1-5 grams of colourants. This is a major difference compared to conventional digital printing where the liquid ink generally only comprises 20% pigments and the ink drop comprises always a smaller amount of colourants than the ink drop itself. Generally about 5 grams of conventional pigmented ink must be applies in order to apply 1 gram of pigments on a surface.

Figure 8A:
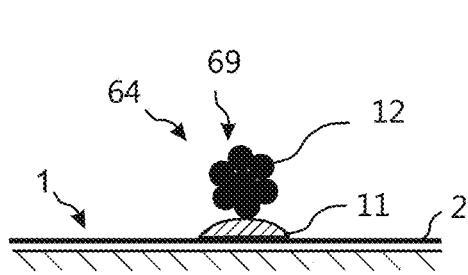
FIGS. 8a-h Illustrate preferred embodiments of macro colourants.

FIGS. 8a-8h show preferred embodiments of macro colourant particles 64. Such particles may comprise or consist of several individual colourant particles 69 that may be connected to each other to macro colourant particles 64 having a specific colour. The macro colourant particles 64 may also be produced by a combination of several materials and chemicals having a particle body 66 and pigments included in the particle body 66 or attached to the surface of the particle body. FIG. 8a shows an embodiment comprising several individual colourants 69, for example pigments 12, that are connected to each other with a binder and that form a macro colourant particle 64. Such macro colourants may be produced by mixing, for example, pigments 12 with a liquid thermosetting resin, for example melamine.

The mix is dried, milled and sieved into macro colourants comprising pigment clusters of a pre-determined size.

Figure 8B:
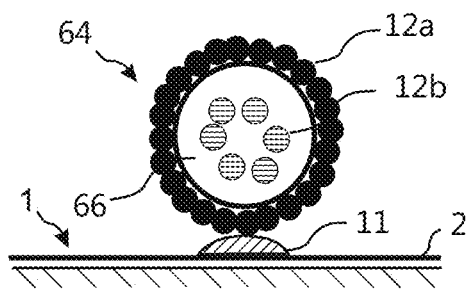

FIG. 8b shows a macro colourant particle 64 having a particle body 66 of a spray dried thermosetting or thermoplastic resin, that comprises pigments 12a, 12b in the particle body 66 and on its surface. The pigments may be of different colours. The colourant in the body 66 may also be a dye. Mixing, for example, a liquid thermosetting resin, for example melamine, with pigments or dyes prior to the spray drying may be used to produce such particles. The pigment on the surface may also be attached by mixing pigments with the spray-dried particles. The pigments wills stick to the surface of the spray dried particle body. The bonding strength may be increased if the mixing is made under increased humidity or heat especially when the particle body comprises melamine. The melamine-based particles may be heated in a final stage where the pigments will be firmly bonded to the body. The curing level of the melamine particles may be increased and this will prevent bleeding of the pigments during a final pressing and curing of the printed surface. The macro colourant particles 64 have preferably a diameter of about 30-100 micron and pigment content may be 10-50% of the total weight. The resin may be melamine or polyacrylate. A binder may also be added to the mix in order to increase the bonding between the pigments and the particle body.

Figure 8C:
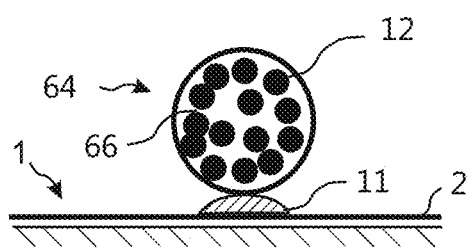

FIG. 8c shows a macro colourant particle 64 comprising a thermosetting or thermoplastic particle body 66 with colour pigment 12 in the particle body 66.

Figure 8D:
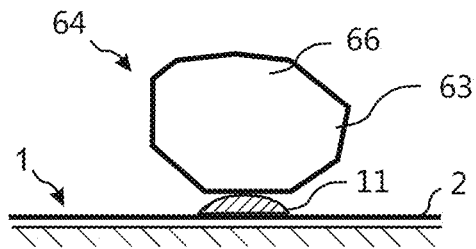

FIG. 8d shows that, for example, macro colourant particles 64 may be mineral particles that comprise natural colours. Sand or stone powder or various types of minerals derived from, for example, oxygen, silicon, aluminium, iron, magnesium, calcium, sodium, potassium and glass powder may be used. A preferred material in some applications that intend to copy stone is sand that is a naturally occurring granular material composed of finely divided rock and mineral particles. The composition and colour of sand is highly variable, depending on the local rock sources and conditions, but the most common types of sand comprises silica (silicon dioxide, or $SiO_2$), usually in the form of quartz.

A preferred embodiment is aluminium oxide 63 that is very suitable to bond and coat with a melamine resin.

Mineral particles and especially coloured glass particles comprising pigments, similar to the glazing powder used in tile production, are very suitable for BAP printing on tiles but may also be used in other BAP applications. A BAP print may be applied on a tile body comprising a basic glaze layer with a base colour. Such basic glaze layer may be pre-pressed or applied in wet form and dried. The BAP print may during firing of the tile melt into the basic glazing layer. A transparent glaze layer may also be applied over the BAP print. A binder may be applied on the basic glaze layer, on the coloured glass particles or in the dry ink such that an application bond may be obtained by exposing the blank and dry ink to, for example, IR light or hot air.

Figure 8E:
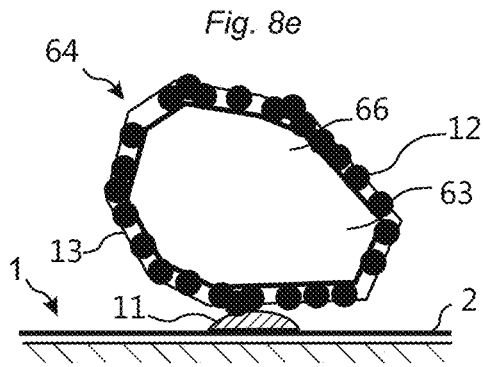

FIG. 8e shows that essentially all minerals, such as, for example, aluminium oxide particles 63, may be coated with a thermoplastic or thermosetting resin, for example, melamine 13. The resin may be used to bond colour pigments 12 to the particle body 66. Such macro colourants 64 are very easy to apply on and remove from a surface and they may provide a very wear resistant print with pigments applied on the upper parts and the lower parts of the particle body 66. A preferred average size of mineral based macro colourants is about 100 microns. This particle size may be used to create a wear resistant print with a particle depth of 100 microns. The binder content is preferably 10-30% and the pigment content is preferably 5-25% of the total weight of the macro colourant particle.

Mineral particles comprising an aluminium oxide particle body 66 coated with pigments and a melamine resin are especially suitable to be used as dry ink when a bonding is made with a heating print head 80. Aluminium oxide particles have a high thermal conductivity and melamine resin may be bonded with a heat of about 100 degrees C.

Figure 8F:
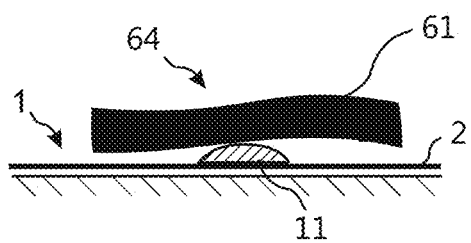

FIG. 8f shows that the macro colourant particles 64 may comprise natural fibres, for example, wood fibres 61. No pigments are needed since the fibres may have natural colours. Fibres from a lot of different wood species may be used, for example, from softwood such as pine and spruce and hardwood such as ash, beech, birch and oak. The colours may be modified by heat treatment. Even cork particles may be used. Such natural colourants may be coated with a binder, preferably a thermoplastic or thermosetting resin, for example melamine. The coating may be used to improve scattering properties and/or as a binder to bond the macro colourant to the surface and the binder pattern created by the blank ink.

Figure 8G:
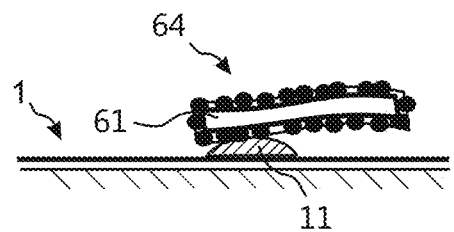
Figure 8H:
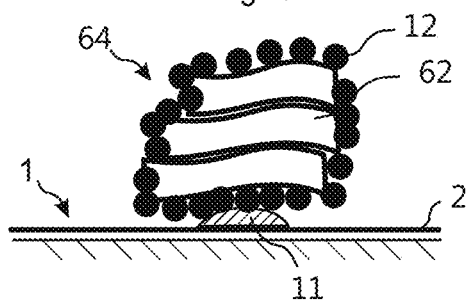

FIGS. 8g and 8h show macro colourant particles 64 comprising wood fibres 61 and wood chips 62 that have been coated with a resin and pigments 12.

Fibre based macro colourants may be used to create an almost identical copy of wood. Wood fibres having different colours form the wood grain pattern in a real wood plank. The BAP printing method allows that the same principles may be used with different fibres that actually form the wood grain pattern and not small ink drops arranged in a raster pattern. This is shown in FIG. 6c. The panel 1 has a surface with a wood grain decor comprising a first surface portion S1 that is formed by a basic layer 2 comprising wood fibres 61a having a first colour. A second surface portion S2 is formed by wood fibres 61b having a second colour. The wood fibres having the second colour are applied on and bonded to the basic layer. The basic layer is preferably continuous. The second surface portion S2 covers preferably a part of the first surface portion S1. The base layer 2 may be a powder mixed with a thermosetting resin, a coloured paper or a coloured wood based core. The fibres in the two surface portions S1, S2 have preferably different average sizes. The fibres in the second surface portion S2 are preferably smaller than the fibres in the first surface portion S1. The second surface portions S2 comprise preferably a pattern with a length L that exceeds the width W.

The coating with resins may be used to bond pigments to the particle body and to bond the macro colourant particle by the blank ink to the surface. The coating may be made in several steps with intermediate drying and curing of the resin. It is preferred that a first coating, drying and curing with a thermosetting resin, for example, a melamine resin is made under higher temperature than the second curing. The first curing may be made such that the melamine resin is cured to an essentially C stage where the melamine will not float during the final pressing operation and this will eliminate bleeding of the pigments. The second coating is preferably cured to a B stage where the melamine is possible to melt with the dry ink. Dry ink particles may be produced from wood fibres 61 that are mixed with pigments and melamine resin and they are thereafter pressed under increased temperature such that the melamine resin cures. The pressed mix may be milled into small particles and coated with liquid melamine resin and dried such that the outer melamine coating is in a B stage. A binder layer may be applied between the pigments and the particle body and on the pigments such that they are completely coated with a binder layer. Several layers of pigments with different colours may be bonded to a particle body of a macro colourant.

Dry ink may comprise a mix of several different types of macro colourant particles, for example, melamine/minerals, melamine/fibres, fibres/minerals etc. and the structure and the size of the macro colourants may be used to create special decors.

The coating of the particle body 66 is preferably made in several steps where, for example, particles such as fibres or minerals in a first step are mixed with a resin, preferably spray dried melamine, and pigments. This mix may be applied as a rather thin layer, with a thickness of, for example, 1-3 mm, on a conveyor. The mix is as a third step sprayed with water and dried by hot air or an IR lamp. The particle body, in this embodiment the fibres or minerals, are coated and impregnated with the wet melamine and the pigments are bonded to the particle body. The small layer thickness makes it possible to dry the layer during a short drying time, for example a minute, and the resin may still be in a semi-cured B-stage. The dry mix is removed from the conveyor by, for example, scraping and the dry flakes are milled and sieved to pre-defined particle sizes. The spray dried melamine particles and water may be replaced with a wet binder, for example wet melamine that may be sprayed on a mix comprising pigments and particles that forms the particle body 66.

The pigments may also be bonded to the particle body 66 with a binder that comprises water based acrylic emulsions.

Macro colourants may provide a print that is very similar to an original wood or stone design especially when fibres are used to copy a wood grain pattern and minerals are used to copy a stone design. Conventional rotogravure methods with a printing cylinder may be used to apply blank ink on a surface. Dry ink comprising macro colourant particles may be applied on the blank ink and non-bonded particles may be removed according to the BAP printing principles described above. Such printing method may be used to provide an advanced print comprising a design that is not possible to create with conventional ink.

Macro colourants may be used to create a pattern, preferably a wood or stone pattern in LVT floors. The BAP printing method may be used to apply a print on the core, on the foil or on the lower or upper side of the transparent protective layer. Colourants may be melted into the layers during the pressing operation. Prints in different layers located vertically above each other may create a 3D effect. Printing on transparent layer may create an even more realistic 3D effect.

Figure 9A:
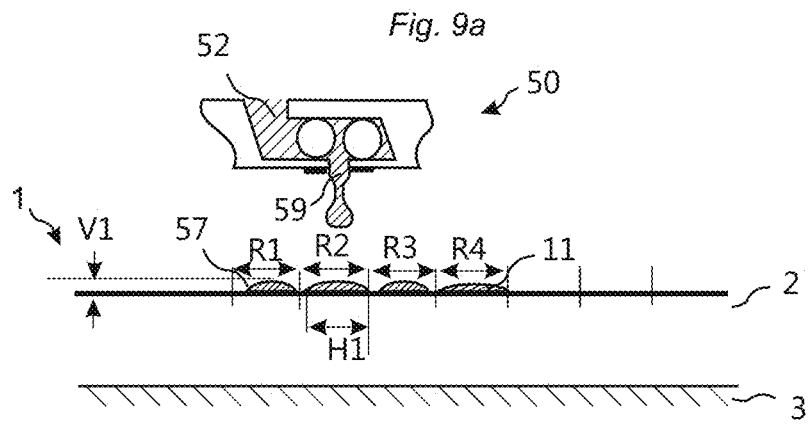
FIGS. 9a-e Illustrate application and pressing of macro colourants.

FIGS. 9a-9e show BAP printing with dry ink comprising macro colourants 64 with a fibre based 61 particle body 66 coated with a melamine resin 13 and pigments 12. Jets 50 from a preferably thermal ink head apply drops of blank ink 11 in a raster pattern R1-R4 that form blank ink spots 57 on a surface 2 that in this embodiment is a pre-pressed powder layer applied on a core 3 as shown in FIG. 9a.

Figure 9B:
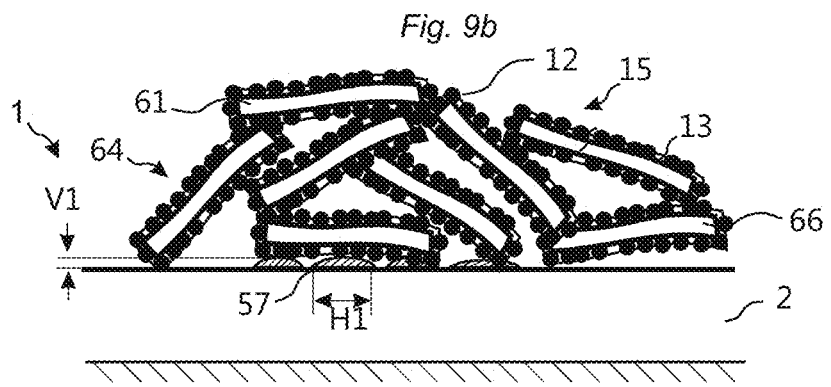
Figure 9C:
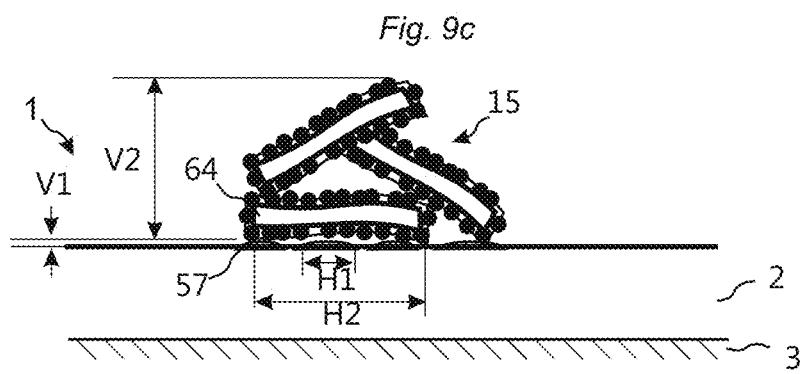

FIG. 9b shows a dry ink layer 15 comprising fibre based macro colourants 64 applied on the surface 2 and FIG. 9c shows the dry ink layer when non-bonded macro colourant particles have been removed. The blank ink 11 penetrates into the dry ink layer 15 from the surface and upwards due to capillarity and the binder properties and several macro colourants located vertically above each other may be bonded by blank ink spots 57. The horizontal extension H2 of individual colourants, preferably macro colourant particles 64, exceeds preferably the horizontal extension H1 of the ink spots 57 and the vertical extension V2 of the dry ink layer, after the removal of the non-bonded particles, exceeds preferably the vertical extension V1 of blank ink spots 57. The vertical extension V1 of the blank ink spots is generally about 10 microns or smaller. The vertical extension V2 of the applied and bonded blank ink layer, after the removal of the non-bonded particles, may be at least 50 microns or even larger, preferably larger than 100 microns. This is a major difference compared to traditional ink jet printing where pigments are included in the ink drops. BAP printing allows that a print comprising larger volumes of colourants may be formed than the volume of the blank ink applied by the digital drop application head.

Figure 9D:
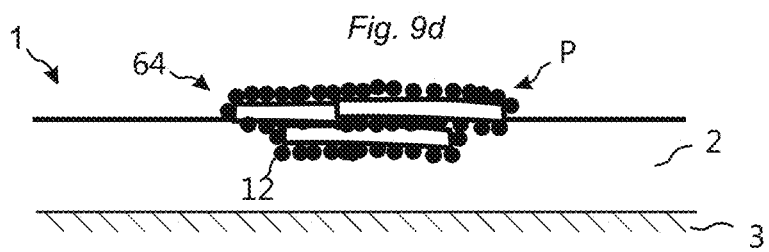

FIG. 9d shows the BAP print P after a stabilization step that in this embodiment is a pre-pressing operation. The macro colourants 64 may be partly pressed into the powder-based surface 2.

Figure 9E:
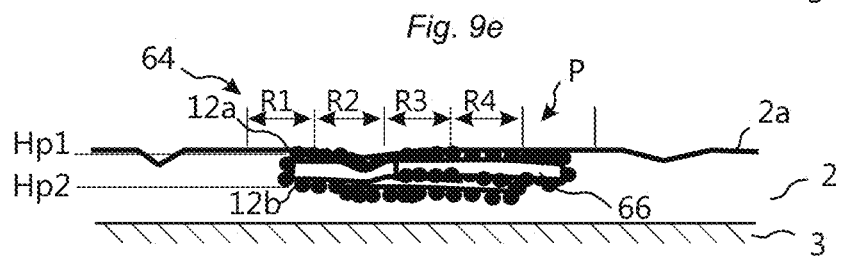

FIG. 9e shows the powder-based surface in a completely cured stage after the final pressing operation. The macro colourants 64 are pressed into the powder based surface 2. The print P comprises pigments 12a, which are located in a first horizontal plane Hp1 at the upper part of the surface 2a and pigments 12b located at a second horizontal plane Hp2 below the particle body 66 and below the first horizontal plane Hp1. The macro colourants 64 comprise pigments 12a, 12b on the upper and lower side of the particle body 66.

The macro colourant particles are applied at random and are preferably offset in relation to the raster pattern R1-R4 where each row and column represent one pixel and one dry ink spot 57. The print P may be a solid print with several macro colourants connected to each other and/or overlapping each other. The BAP print in this preferred embodiment is characterized in that the blank ink 11 is applied in a raster pattern (R1-R4) and that the dry ink 15 is applied at random with overlapping colourants 7 or macro colourants 64. Preferably the size of a macro colourant particle 64 is such that it covers several pixels in a raster pattern.

The thickness (diameter) of the fibres 61 is preferably about 10-50 microns and the length may be 50-150 microns. The length may in some applications also exceed 150 microns and realistic wood grain designs may be formed with fibres having a length of about 100-300 microns.

Figure 10A:
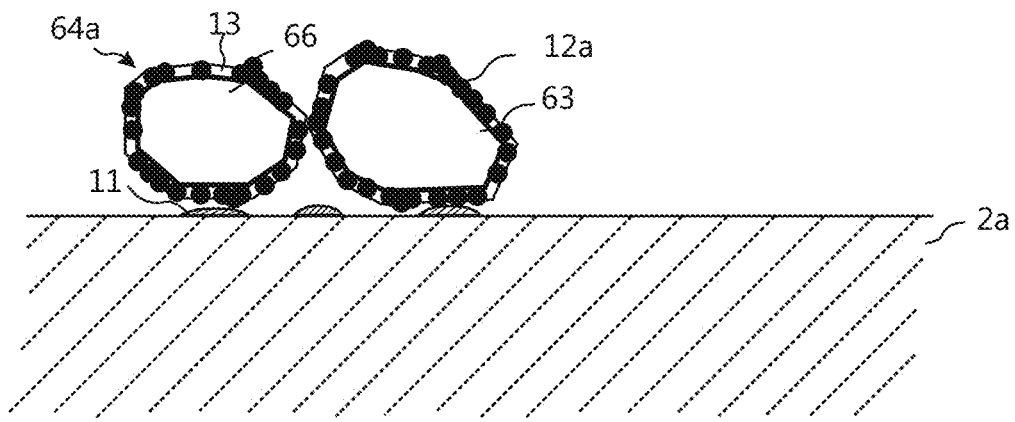
FIGS. 10a-c Illustrate application and pressing of macro colourants.
Figure 10B:
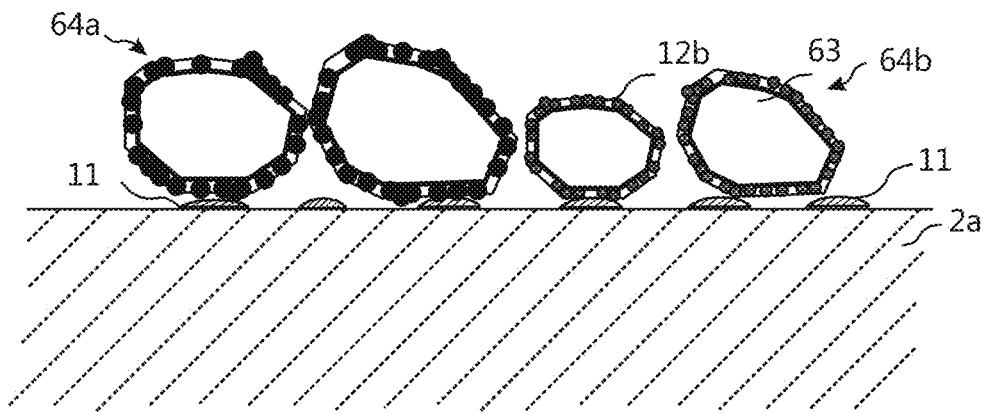
Figure 10C:
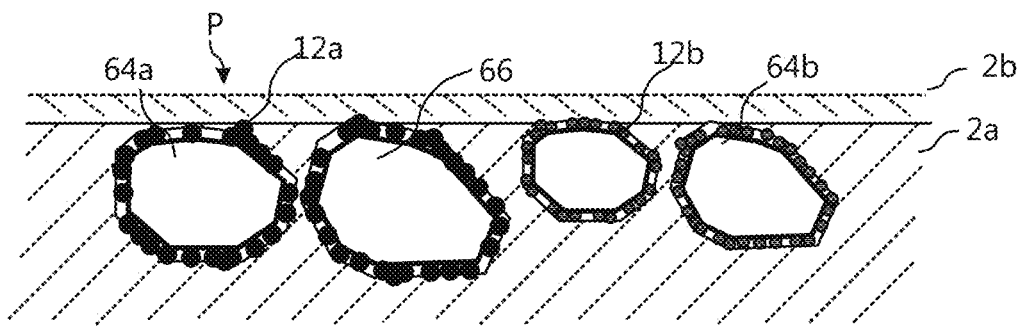

FIG. 10a-10c show a BAP print with a very high wear resistance. Macro colourants 64a comprising a particle body 66 of aluminium oxide particles 63 coated with pigments 12a and a melamine resin 13, are applied on a surface, that in this embodiment is a powder based surface 2a comprising melamine powder and pigments and preferably also wood fibres. The surface includes preferably a base colour. A layer comprising macro colourants that gives the panel a basic colour may also form the surface 2a and may be applied directly on a wood or plastic based core, a tile body or on a surface comprising powder, paper a foil and similar surfaces. FIG. 10a shows macro colourants 64a bonded to the surface 2a by blank ink 11. FIG. 10b shows a second layer of macro colourants 64b comprising pigments 12b with a different colour. FIG. 10c shows the final cured surface with macro colourants that are pressed into the powder based surface 2a and preferably covered with a transparent layer, preferably a melamine layer 2b that may be applied after a pre-pressing operation but prior to the final pressing step. The transparent melamine layer 2b may also comprise bleached transparent wood fibres. It may be an overlay, a lacquer, a foil or a glazing. A high wear resistance may be reached since a considerable part of the surface 2a, 2b, including the particle body 66 of aluminium oxide particles 63, must be worn of before all pigments 12a, 12b in the print P are removed. Aluminium oxide particles with or without pigments (not shown) are preferably also included in the powder base surface layer 2a and/or in the transparent melamine layer 2b. The method may also be used to apply a wear resistant digital print on many other surfaces such as paper, foils, tiles and other surface layers described in this disclosure.

Figure 11A:
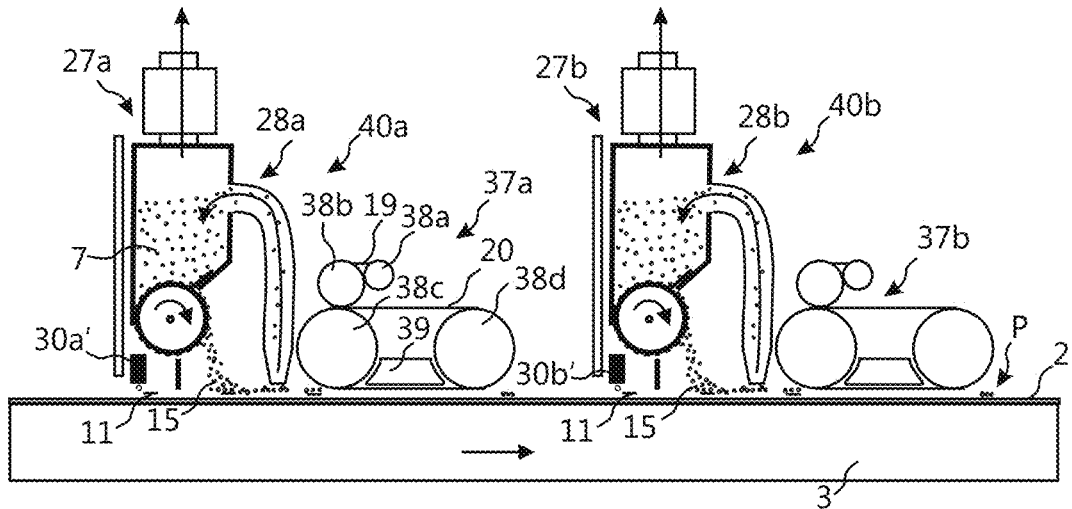
FIGS. 11a-c Illustrate application of several colours with one print head and application and removal of colourants with intermediate pre-pressing.

FIG. 11a shows a BAP equipment comprising several BAP printing stations 40a, 40b that each is used for a print forming cycle that applies one specific colour. Each BAP station comprises a digital drop application head 30'a, 30'b and a combined dry ink application and removal station 27a, 28a 27b, 28b and pre-pressing units 37a, 37b that stabilize the dry ink 15 such that a new dry ink layer may be applied and removed according to the principles describe above. An embodiment of unit may replace an IR lamp. An embodiment of unit 37a comprises preferably a heating 38c and a cooling 38d roller, a belt 20, and a pre-pressing table 39. These parts may in some applications be replaced by just one roller. A liquid release agent 19 may be applied on the belt 20 by rollers 38a, 38b or brushes or similar devices. Preferably the drop applications heads 30a', 30b' use the same blank ink 11 to provide a print P with several colours. This is an advantage compared to conventional printing. The BAP printing method allows in fact that the final printing ink is mixed and produced in line when the blank ink 11 and the colourants 7 from the dry ink 15 are attached to each other on the surface 2.

Figure 11B:
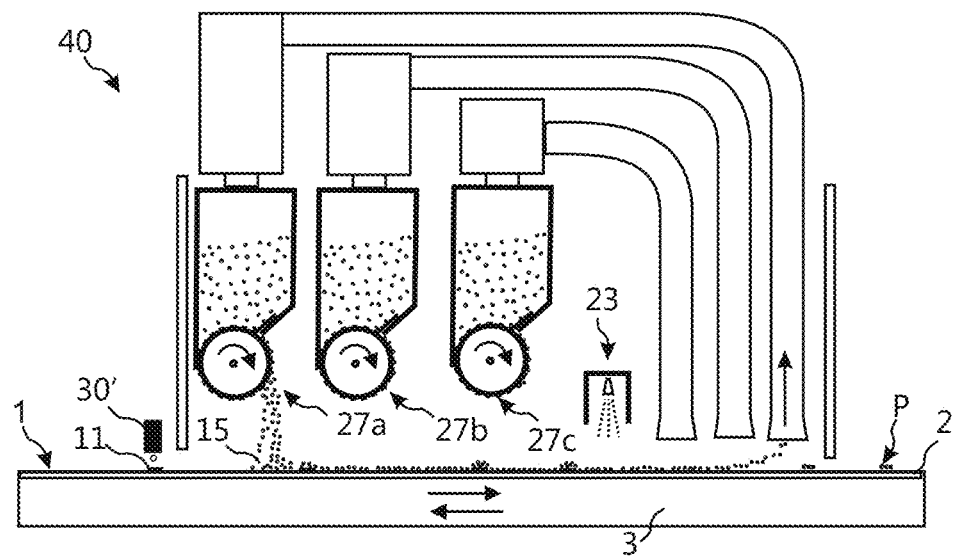

FIG. 11b shows schematically a compact BAP printing station 40 where, for example, one set of digital drop application heads 30' aligned in one row, each comprising one ink channel, and one set of IR lamps 23 or pre-pressing units may be combined with several dry ink 15 application stations 27a, 27b, 27c positioned in the feeding direction after the drop application head 30'. One row of drop application heads 30' may apply colourants with many different colours. The blank ink, that preferably is an essentially transparent liquid substance, comprises preferably a different colour than a first and preferably also a second digital pattern formed by the drop application head 30'. This is a major difference compared to conventional digital printing where each print head applies a specific colour and this colour is always the same as the liquid substance applied by the print head. A surface layer 2 or a surface that is a part of a floor panel 1 may be displaced in two directions and each cycle may be used to apply one specific colour with the same drop application head. The BAP printing station may comprise IR lamps or pre-pressing units and dry ink application stations on both sides of the digital drop application head and different colours may be applied when the surface 2 is displaced under the head 30' in each direction. This means, for example, that three colours may be applied by the same drop application head 30' on a base colour when a panel 1 is displaced under the head 30', back again to its initial position and under the head again. The speed may vary between the various application steps. This may be used to increase the capacity. A wood grain pattern is generally made up of different amounts of specific colourants. The speed may be increased when the amount of a specific colourant is low since only a small amount of blank ink has to be applied on the surface. A digital control system may be used to optimize the capacity and to adapt the speed to the amount of blank ink 11 that is needed to form a specific digital pattern. Several alternatives may be used to combine one blank ink drop application head with several dry ink applications stations and removal stations. A panel may after the first print forming cycle be displaced vertically or sideways to a conveyor that brings it into an initial position. An intermediate stacking unit may also be used. Paper and foil material in rolls may be printed several times with the same drop application head and the same blank ink.

Figure 11C:
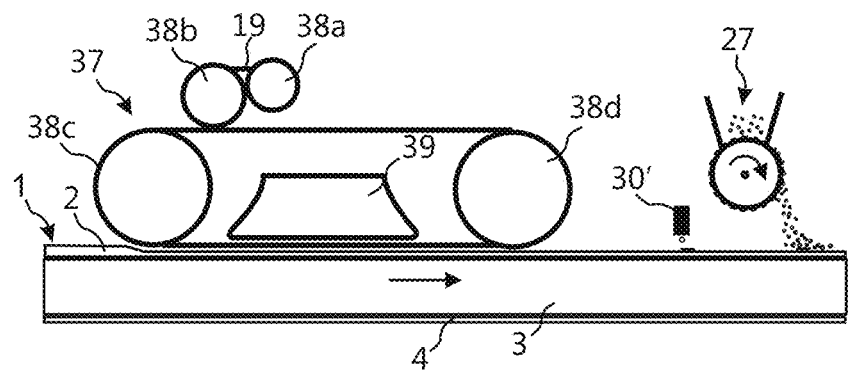

FIG. 11c shows a pre-pressing unit 37 that may be used to pre-press a powder layer with a basic colour prior to the BAP printing. Such a pre-pressing unit may also be used to stabilize the prints or to pre-press and connect a powder based backing layer 4 on rear side of a core 3. When melamine is used as binder, a heating roller 38c and a pre-pressing table 39 may apply a heat of, for example, 90-120° C. and a cooling roller 38d may cool down the semi-cured layer 2 to a temperature preferably below 80° C. The pressing may be made at rather low pressures, for example, 5 bars or lower and the pressing time may be about 10 seconds or shorter. The melamine will be pre-pressed to a semi-cured B-stage that may be further pressed and cured in a final pressing operation. A sheet material with a pre-pressed powder base surface and backing layer may be produced and used as a pre-finished panel. Other binders, for example, thermoplastic binders may be pre-pressed with other temperatures specifically adapted to the binder properties.

Figure 12A:
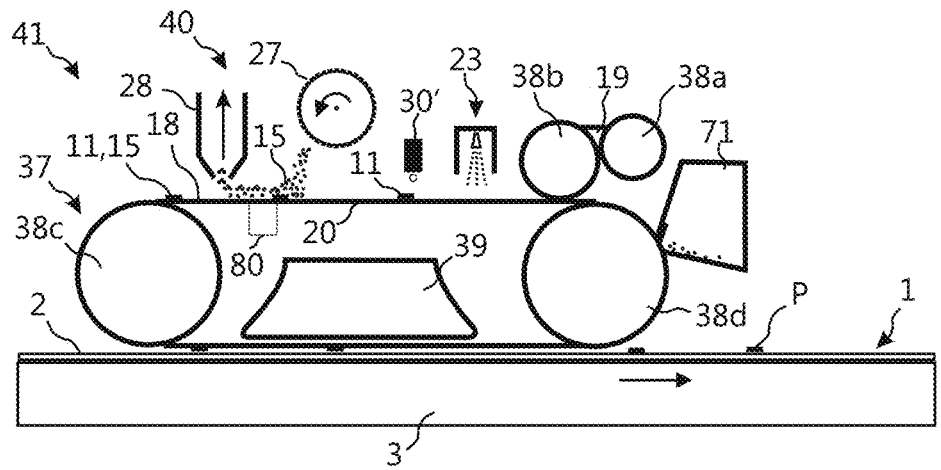
FIGS. 12a-d Illustrate transfer printing methods and panels with preferred surfaces.

FIG. 12a shows that a BAP printing station 40 and a pre-pressing unit 37 may be combined into a BAP transfer printing station 41 and used in combination to create a digital BAP transfer print P on a surface 2. Blank ink 11 and dry ink comprising colourants 7, preferably pigments 12, are applied on a transfer surface 18 that may be, for example, a steal or plastic belt or similar. The print P is pressed on a surface 2 by rollers 38c, 38d and preferably by a pre-pressing table 38. The BAP transfer printing unit may comprise a cleaning device 71, rollers 38a, 38b or brushes that apply a release agent 19 and preferably also an IR lamp 23 that dries the release agent prior to the application of the blank ink 11. The release agent may also be mixed into the dry ink 15.

The BAP transfer printing method provides the advantages that blank and dry ink may be applied on a pre-defined transfer surface 18 that may be specially adapted for a high definition application of blank ink without any risks for bleeding and an easy application and removal of dry ink. This allows, for example, that a BAP print may easily be applied on rather rough surfaces such as, for example, textiles, carpets, various board materials and similar surfaces. The BAP transfer print may be combined with all other described methods, for example, the method described in FIG. 11b where one drop application head 30' is used to apply several colours.

Figure 12B:
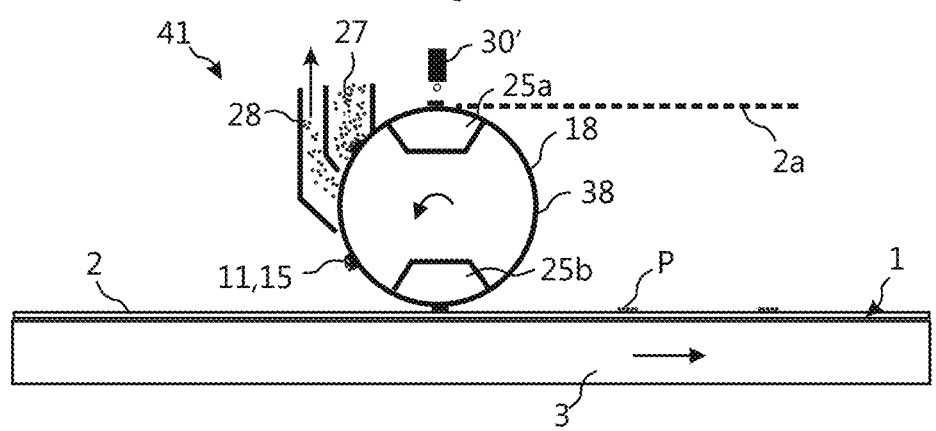

FIG. 12b shows a BAP transfer printing station 41 where the belt has been replaced by a roller 38 comprising a transfer surface 18. The roller comprises preferably heating 25a and cooling 25b zones. The non-bonded dry ink may be removed by gravity that may be combined with ultrasound, vibrations or air streams. This method may also be used to apply a direct BAP print on a flexible surface 2a that may be a paper, a foil or similar. The application may be made in line with a pressing operation or as a separate production step.

Figure 12C:
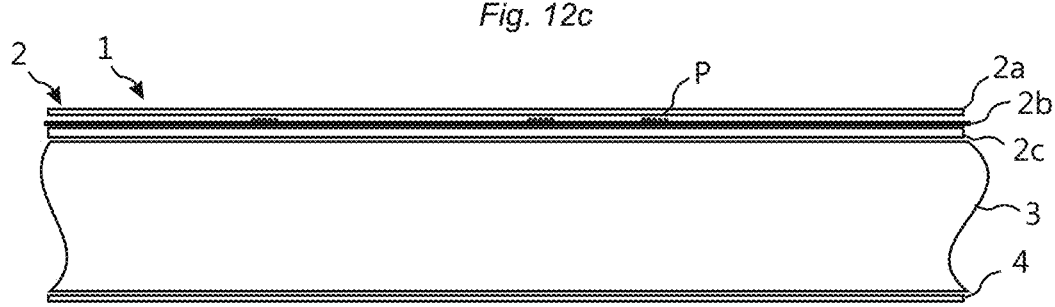

FIG. 12c shows a preferred embodiment of a floor panel 1 according to the invention. The panel 1 comprises a backing layer 4 on the rear side of the core 3 and a surface 2 on the upper part of the core comprising a sub layer 2c, a paper or foil 2b and a wear layer 2a over the paper. The backing layer 4 and the sub layer 2c may be applied as dry melamine formaldehyde powder and the wear layer may be applied as a dry melamine formaldehyde powder comprising aluminium oxide particles. The paper may comprise a base colour. A BAP print or a conventional digital print may be applied on the paper. Such a dry process may be used to form a very cost efficient panel without any impregnation of a decorative paper or a protective overlay. The spray dried melamine particles will melt during pressing and impregnate the paper. It is obvious that this dry method may be used to save costs even when a conventional decorative paper is used.

Figure 12D:
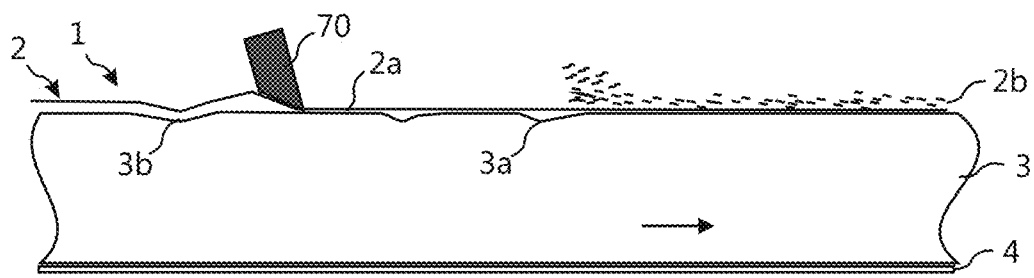

FIG. 12d shows a method to form a base layer on rough core materials 3 comprising cavities, cracks, splints or defects 3a, 3b. Such core material may be made of, for example, plywood or OSB. The problem is that a powder layer generally has the same thickness at the cavities and at the upper parts of the core surface and there will not be sufficient amount of powder to form a high quality surface after pressing since the density of the surface layer will be lower at surface portions with cavities. This problem may be solved with a first powder layer 2a that is applied as filler and pressed by, for example, a roller or a ruler into the cavities such that an essentially flat powder based surface layer 2a is formed. A second powder based layer 2b may be applied on the first filler layer 2a. The two layers may be pre-pressed as described above and a base layer may be formed that in a second step may printed with a preferably BAP print and thereafter cured by heat and pressure. The method may also be used without a print and only powder layers comprising fibres, binders and preferably pigments may be used. This embodiment is characterized in that the powder content above cavities is higher than the powder content above the upper parts of the core. The powder content may be measured by measuring the weight of the powder above a cavity and above an upper part of the surface. The base layer comprising a first filler layer 2a and as second powder layer 2b may be covered by a conventional decorative paper and also preferably with a protective layer, for example a conventional overlay or a transparent lacquer.

Figure 13A:
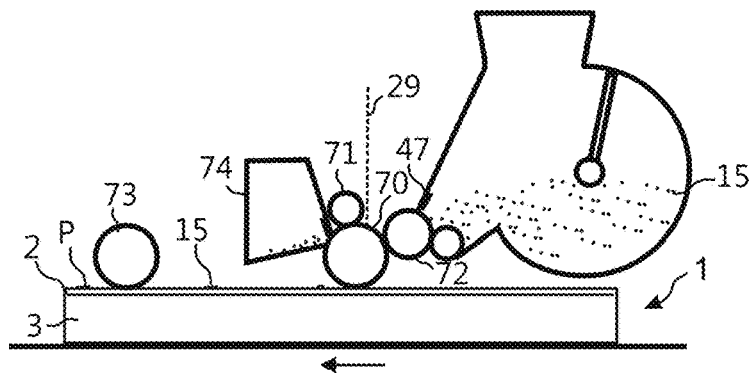
FIGS. 13a-d Illustrate application of colourants in patterns with methods where liquid blank ink is not used to bond colourants.

FIG. 13a shows that a conventional laser printing technology that uses electrical charges to attract and release dry ink particles may be adapted such that digital prints may be provided on a core material 3 comprising a surface 2 that preferably has a base colour. Negative charged dry ink particles 15 that may be conventional laser toner pigments, are applied by a developer roller 72 on a photo conductor drum 70, which is in contact with a charge roller 71. A laser beam 29 projects an image on the electrically charged photo conductor drum 70 and discharges the areas that are negatively charged and an electrostatic image is created. Dry ink particles are electrostatically picked up by the drum's discharged areas. The drum prints the print P on the surface 2 by direct contact. An electrical charge may be applied to the surface or the core such that the pigments are released from the drum and applied on the surface. A fuse roller 73 fuses the dry ink particles to the surface and bonds the dry ink particles. A roller-cleaning device 74 may be used to clean the photo conductor drum. The dry ink particles may comprise a thermoplastic or a thermosetting resin that may be used to bond the particles to the surface with heat and pressure.

Figure 13B:
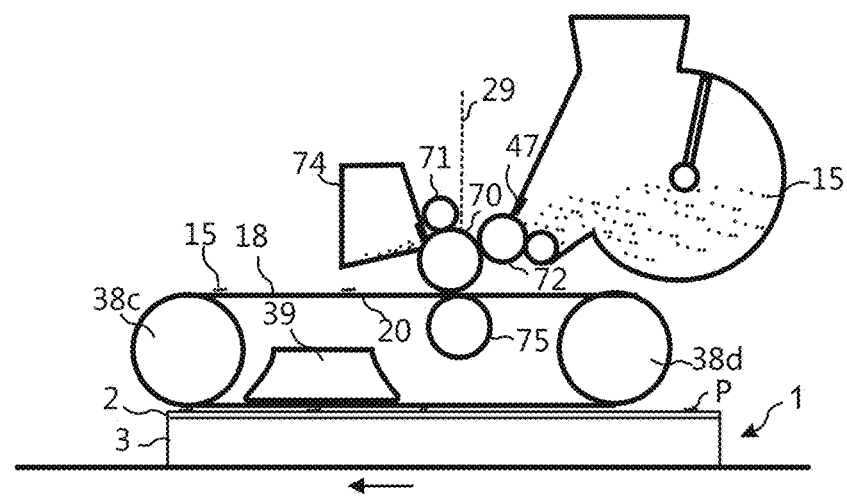

FIG. 13b shows that the laser printing technology may be used to apply a transfer print P on a surface 2. The dry ink particles are applied on a belt 20 comprising a transfer surface 18 and released from the photo conductor drum 70 by an electrical application roller 75 that applies an electrical charge on the belt 20. The dry ink particles are then fused by a pre-pressing table 39 that applies heat and pressure on the belt 20 and the transfer surface 15. Heating 38c and cooling 38d rollers may be used. The belt may be replaced by a transfer roller as shown in FIG. 12b.

Figure 13C:
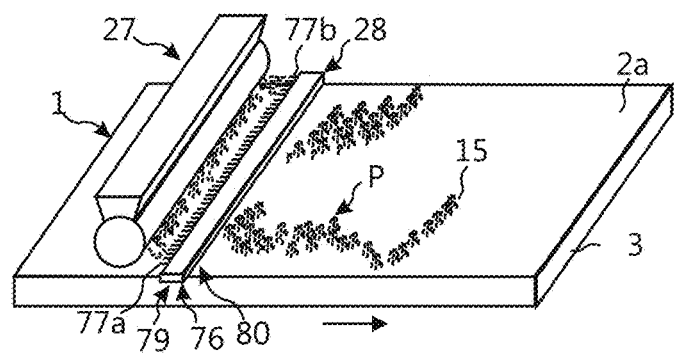

FIG. 13c shows schematically several other preferred principles that may be used to apply particles in well define patterns on a surface 2 without a digital drop application head that applies a liquid binder of blank ink.

A first principle is a method to create a base layer comprising at least two different colours. A first layer 2a with a first base colour is provided as powder or as a coloured paper. A second colour of dry ink 15 is scattered on the first basic colour. Some parts of the dry ink 15 particles are removed with a dry ink removal station 28 comprising several air nozzles 77a, 77b that may remove dry ink particles by, for example, vacuum before they reach the surface with the base colour 2a. The air nozzles 77a, 77b may be controlled digitally with preferably several valves and a dry ink pattern P may be formed. This may be repeated and several colour patterns may be formed without any digital drop application heads or blank ink. This method is particular suitable to form patterns that partly or completely may be used to copy wood or stone designs. This method may be combined with digital BAP printing or conventional digital printing. The method may also be used to create digital prints with high resolution. The dry ink 15 may comprise particles with high density, such as minerals, especially aluminium oxide particles or glass particles, that during scattering may fall in a pre-determined essentially straight direction towards the surface 2 and a precise partial removal may be made with vacuum when the pass the air nozzles 77a, 77b. The applied dry ink is preferably stabilized by water spraying prior or after the application.

The dry ink particles may according to a second principle pass through a set of electrodes, which impart a charge onto some particles. The charged particles may then pass a deflection plate 79, which uses an electrostatic field to select particles that are to be applied on the surface, and particles to be collected and returned for re-use by the dry ink application system.

According to a third principle a heating print head 80 that comprises small heating elements that produce varying amounts of heat similar to the print heads used in the dye-sublimation or thermal printing technologies, may be used to attach colourants to a surface. Several heating print heads 80 may be attached side by side such that they cover the whole width of a printed surface. Rather low temperatures of about 100 degrees C. may be used to obtain an application bonding of the dry ink particles. The heat may also be rather high, for example 200-250° C. and such heat will not destroy wood fibres in paper and powder based layers. Several methods may be used to form a digital print with dry ink where the dry ink particles are bonded to a surface in a pre-determined digitally print. Contrary to known technology such heating heads, combined with dry ink, may be used to apply a wide range of different colours without any heat sensitive papers or transfer foils. A thermo sensitive binder, that may be a thermosetting or thermoplastic resin, wax and similar materials with a low melting points, may be included in the surface layer or in the colourants of the dry ink. Powder comprising dye-sublimation particles of different colours may be used as dry ink. The heating print head 80 may apply digitally controlled heat directly on well-defined portions of the dry ink after application, or on the surface layer prior to the application of dry ink. The heating ink head may comprise heating elements arranged on an essentially flat surface or on a cylinder that rotates when a surface with dry ink is displaced under the heating print head. Alternatively a heat transfer foil 81 as shown in FIG. 4d, may be applied between the dry ink and the heating print head 80 and may slide against the heating elements and the ceramic substrate of the heating print head. The non-bonded colourants or non-vaporized dyes may be removed and reused.

FIG. 12a shows that a heating print head 80 may be used to provide heat on a transfer surface 18 that heats up the dry ink 15. The transfer surface may be used as a heat transfer foil 81. The heating print head 80 may be located such that it provides a heat through a transfer surface 18 or on the dry ink 15 applied on the transfer surface 18. The heating print head 80 may also heat up portions of a surface prior to the application of dry ink. The surface may be a board material, powder, paper, a foil, a base coating, a transfer surface, and all other surface materials described in this disclosure.

Figure 13D:
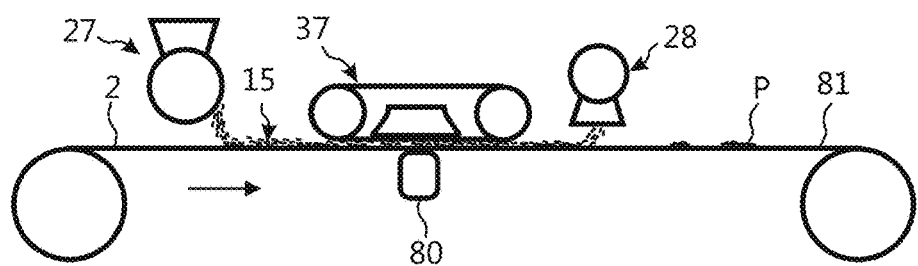

FIG. 13d shows that heating print heads 80 and dry ink 15 are especially suited to be used to form a digital print P on flexible thin surfaces 2 that preferably may be a paper, a foil, a textile material, and similar materials that generally have sufficient heat transfer abilities and heat resistance to function as a heat transfer foil 81. A powder and heat printing equipment may comprise a scattering station 27 that applies blank ink 12 on a surface, a heating print head 80 that bonds a part of the blank ink 15 with heat to the surface 2 and a dry ink removal station 28 that removes non-bonded dry ink 15. In some application a pre-pressing unit 37, vacuum applied on the lower side of the surface or oscillation may be used to increase the contact between the dry ink particles and the surface during the heat bonding. A separate heat transfer foil as shown in FIG. 4d may be used to increase the printing capacity. The pre-pressing unit 37 may also comprise heating print heads and heat may be applied from the upper and/or the lower side.

The heating print head 80, with or without a heat transfer foil 81 may replace all digital drop application heads 30' in the embodiments of this disclosure.

Embodiments of the three principles described above are based on the main method that colourants are applied as powder in dry form on a surface and bonded in a predetermined pattern that forms a print. The surface may be a transfer surface 18 and the three principles may be used to provide a transfer print.

Figure 14A:
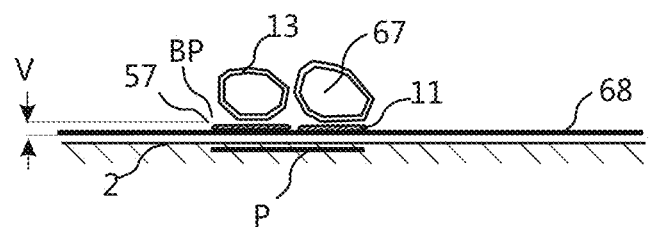
FIGS. 14a-d Illustrate digital embossing with press particles.
Figure 14B:
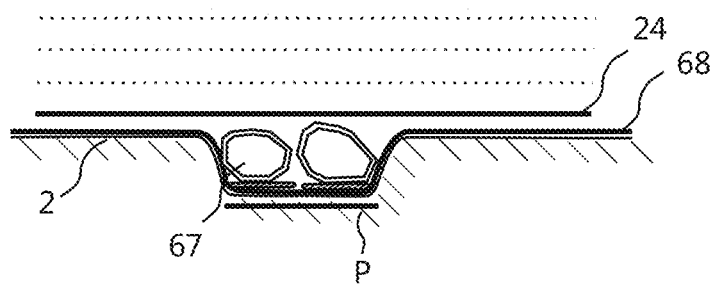
Figure 14C:
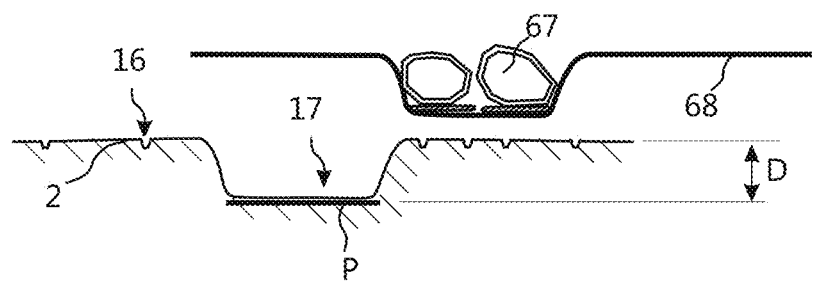

FIGS. 14a-14d shows a method to form a digital embossing on a surface 2 preferably an EIR structure, hereafter referred to as BAP embossing. A digital drop application head applies a pattern of blank ink on a carrier 68 as shown in FIG. 14a. Press particles 67 which are similar to the colourants shown in FIGS. 8d-8h may be applied on the carrier 68 that may be an aluminium foil, plastic foil, paper and similar. The application may be the same as for the BAP printing and all methods described above may be used to apply press particles 67 in a pattern on a carrier 68. However, the press particles 67 do not have to be coated with pigments. They may be coated with a thermosetting 13 or thermoplastic resin. In some application the blank ink is sufficient to provide an application bond. A heating print head may also be used to bond the press particles 67 to the carrier. The carrier 68 and/or the blank ink may also comprise a binder. The particles are preferably hard minerals such as aluminium oxide, sand, stone powder and similar. Such particles that essentially maintain the original shape during pressing and are not compressed during a pressing operation are referred to as hard press particles. The size of the particles should be adapted to the depth of the embossing. Particles with a diameter of about 0.2 mm may, for example, be used to create an embossing with a depth of at least 0.2 mm. The carrier 68 with the press particles 67 is positioned and coordinated with a printed pattern P that may be a conventional print or a BAP print applied on, for example, a powder or paper surface 2. FIG. 14b shows the pressing step where the press particles 67 and the carrier 68 are pressed by the press table 24 into the surface 2. FIG. 14c shows the embossed structure 17 when the carrier 68 with the press particles 67 is removed after pressing and a perfect digitally formed EIR surface is obtained that may be coordinated with any type of digital prints P without any conventional press plates. A part of the surface structure, especially the microstructure 16 that provides the gloss level, may be formed by the carrier. The deep embossed structures 17 are formed by the press particles and the carrier 68.

The BAP embossing provides the advantages that a deep embossing may be formed with only one or a few BAP application steps since considerable amount of press particles 68 may be applied with thin layers of blank ink 11. This method allows that the embossing depth D exceeds the vertical extension V of the blank ink spots 57 that connect the press particles to the carrier.

Figure 14D:
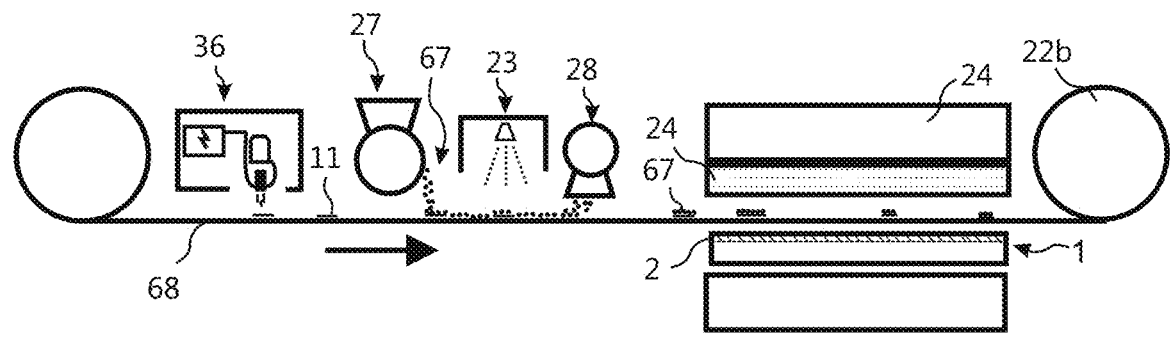

FIG. 14d shows a method to form the surface 2 of a panel with BAP embossing. A blank ink application station 36 applied blank ink 11 on a carrier 68 that in this embodiment preferably is aluminium foil or a coated release paper. A dry ink application station 27 is used to apply press particles 67 on the carrier. An IR lamp 23 may be used in some applications to create an application bonding. The press particles are removed by a dry ink removal station 28 and the carrier with the press particles is pressed against the substrate by a press table 24. The carrier and the press particles are thereafter removed and a BAP embossed structure is formed.

The method may be used to form a conventional embossing or an EIR embossing.

The carrier 68 surface that is pressed against the embossed surface 2 may be coated such that different gloss levels or microstructures may be obtained. Such coating is preferably made digitally according to a method described in this disclosure.

The press particles 67 may be bonded to the carrier with all methods described above. For example heating print heads 80 and laser 29 may be used.

Figure 15A:
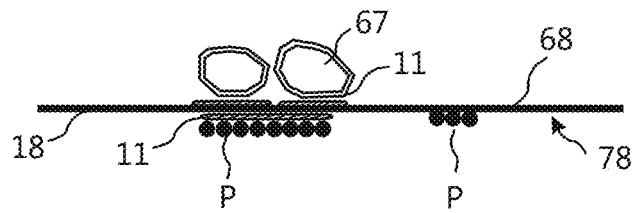
FIGS. 15a-d Illustrate digital embossing combined with digital transfer print.
Figure 15B:
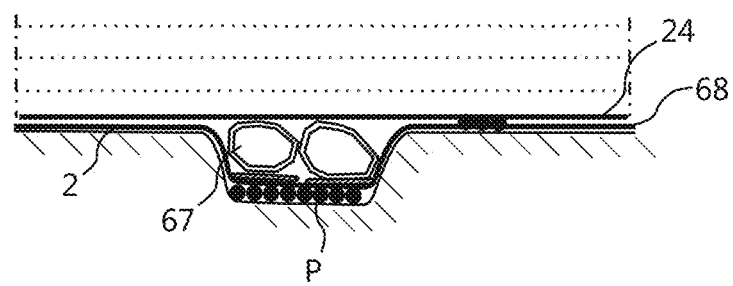
Figure 15C:
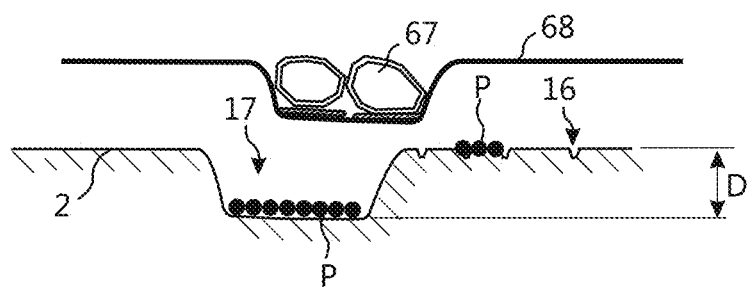
Figure 15D:
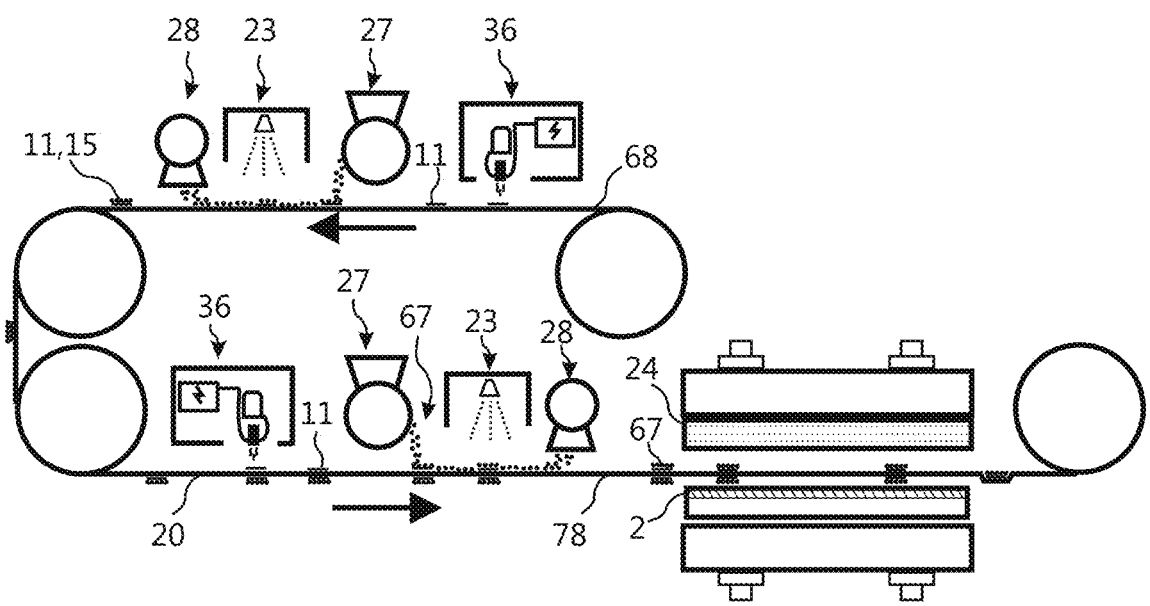

FIGS. 15a-15d shows that the BAP transfer print method may be combined with the BAP embossing method. Press particles 67 may be applied on one side of a carrier 68 and a BAP print may be applied on the opposite side of the carrier 68 that comprises a transfer surface 18 as shown in FIG. 15a. The carrier 68 may be a foil, paper, and similar as described above. The BAP print may also be replaced with a conventional digital print or even with a print provided with conventional rollers. Preferably the print P and the pattern of the press particles 67 are coordinated such that an EIR structure may be formed. FIG. 15b shows that the carrier 68 and the press particles 67 together with the print P are pressed on a surface 2. FIG. 15c shows that the print P is bonded to the surface 2 and that the carrier 68 with the press particles 67 forms an embossed structure 17 when removed after the pressing operation. The application of the press particles 67 and the dry ink print may be made in line with the pressing operation as shown in FIG. 15d or as a separate operation where a pre-printed and pre-embossed carrier 68 is formed that may be supplied as an individual carrier preferably as a foil. A combined BAP printing and embossing equipment may comprise blank ink application stations 36, dry ink application stations 27 and dry ink removal stations 28 that apply and remove dry ink 15 and press particles 67 on opposite sides of a carrier 68.

The particles may also be bonded to the carrier with a laser beam, heating print heads and all other methods described above.

The surface of the carrier 68 that is in contact with the panel surface 2 may be pre-pressed and different gloss levels or microstructures may be formed. Such pre-pressing may be made with conventional embossed cylinders or with a BAP embossing method. Various gloss levels and microstructures may also be formed with digital printing and a coating may be made according to any of the methods described in this disclosure. The carrier 68 with the press particles 67 and preferably also with a transfer print P may be supplied as a press matrix 78 and may be used to form an embossed structure on, for example, laminate, wood and powder based floors but also on tiles and LVT floors. The press matrix 78 may be used several times. The print P may be a conventional print, a digital ink jet print, a digital BAP print or similar.

The method may also be used to form a more durable "mirror shaped" press matrix that may be a sheet material where protrusions on the carrier 68 forms cavities in the sheet shaped press matrix. The carrier with the press particles may be pressed against impregnated paper, preferably phenol impregnated craft paper or powder comprising a thermosetting resin, and a structured sheet matrix may be formed that in a second step may be used as a press matrix.

Metal powder and glass fibres may be included in order to improve the strength and the heat transfer properties.

All the above described methods may be partly or completely combined in order to partly or completely create a digital print or and/or a digital embossing.

Water based blank ink may in some application be combined or replaced by oil or solvent based ink. The advantage with oil-based ink may be that it has a very long drying time and this may improve the function of the digital drop application head.

Example 1—Dry Fibre Based Ink

Dry ink powder was produced by mixing 20% (weight) spray dried melamine formaldehyde particles, 20% dark brown colour pigments and 60% wood fibres of pine with an average length of about 0.2 mm and a thickness of about 0.05 mm. The mix was applied as 1 mm thick layer by scattering equipment on a steal belt. The powder mix was thereafter heated and moisture was applied by steam from deionized water. The mix was dried by hot air such that a hard stabilized powder based surface layer was obtained with a semi cured melamine binder. The dried layer was removed from the belt by scraping and the dry wood particles coated with pigments and melamine resins were milled and sieved into dry ink colourants with a size similar to the size of the individual wood fibres. A dry ink comprising colourants with a wood fibre body and with a surface covered by pigments bonded to the fibres by the semi cured melamine resin was obtained.

Example 2—Digital Print with Heating Print Head

A 8 mm HDF board was sprayed with small water drops of deionized water and a powder mix of 300 g/m2 comprising wood fibres, melamine particles, light brown colour pigments and aluminium oxide particles was applied by scattering equipment on the HDF core. The mix was sprayed again with deionized water comprising a release agent and dried by IR light such that a hard stabilized partly semi cured powder based surface bonded to the HDF core and with a light brown basic colour was obtained. The panel with the stabilized powder surface was put on a conveyer and displaced under digital Kyocera Piezo print head. Dry ink as described in example 1 above, comprising a darker brown colour than the basic light brown powder based surface, was in a second step scattered over the whole powder based surface with a dry ink application station comprising a hopper and a rotating and oscillating engraved roller with a diameter of 5 cm. A dry ink layer of about 30 gr/m2 was applied on the panel surface. An aluminium foil was applied on the dry ink layer and the panel with the aluminium foil was displaced under a heating print head that formed a wood grain pattern. The aluminium foil was removed and the panel was thereafter displaced with a conveyor under a dry ink removal station comprising a vacuum-sucking profile with an opening that covered the whole width of the applied dry ink layer where essentially all non-bonded fibers with the pigments were removed and an air knife that applied an air pressure on the remaining non bonded particles that were released from the panel surface and blown into the vacuum—sucking profile such that essentially all visible dry ink particle were removed. A wood grain patter comprising a light brown base colour and a dark brown wood grains structure was obtained. A protective layer comprising dry a mix of dry melamine and aluminium oxide particles was scattered over the entire surface with the same type of scattering station as described above for the blank ink. The protective layer was sprayed with small water drops comprising a release agent and dried under IR lamps. The panel with the print and the protective layer was thereafter positioned in a pre-determined position in relation to a long and short edge in a hydraulic press and pressed against an embossed steel plate during 20 seconds under a temperature of 170° C. and 40 bars pressure and the powder-based surface with the wood grain pattern and the protective layer was cured to a hard wear resistant surface with a high quality digital print coordinated with the embossed surface structure. The décor of the panel was created by a basic colour and a wood grain design comprising wood fibres and pigments. The obtained copy of a wood design was very realistic since natural wood fibres were used to create the visible pattern.

EMBODIMENTS

1. A method of forming a digital print (P) on a surface (2) wherein the method comprises the steps of:
   applying colourants (7) on the surface (2);
   bonding a part of the colourants to the surface (2) with a binder (11); and
   removing non-bonded colourants (7) from the surface (2) such that a digital print (P) is formed by the bonded colourants (7).
2. The method as in embodiment 1, wherein the colourants (7) comprise pigments (12) mixed with the binder (11).
3. The method as in embodiments 1 or 2, wherein the binder (11) comprises a thermosetting resin.
4. The method as in any one of the preceding embodiments, wherein the binder (11) comprises a thermoplastic resin.
5. The method as in any one of the preceding embodiments, wherein the binder (11) is a powder.
6. The method as in any one of the preceding embodiments, wherein the surface (2) is a paper layer or a foil.
7. The method as in any one of the preceding embodiments, wherein the surface (2) comprises a powder layer.
8. The method as in any one of the preceding embodiments, wherein the surface (2) is a part of a building panel (1).
9. The method as in any one of the preceding embodiments, wherein the surface (2) is a part of a floor panel (1).
10. The method as in any one of the preceding embodiments, wherein the colourants (7) are removed by an airstream.
11. The method as in any one of the preceding embodiments, wherein the binder is a blank ink (11) comprising a liquid substance that is applied by a digital drop application head (30').
12. The method as in any one of the preceding embodiments 1-10, wherein a laser beam (29) or a heating print head (80) makes the bonding.
13. The method as in embodiment 11, wherein the liquid substance is water based.
14. The method as in embodiments 11 or 13, wherein the liquid substance is exposed to IR light (23) or hot air.
15. The method as in embodiment 14, wherein the liquid substance (11) is exposed to UV light.
16. The method as in embodiment 14, wherein the liquid substance is applied with a Piezo ink head.

17. The method as in embodiment 14, wherein the liquid substance is applied with a thermo ink head.
18. The method as in embodiments 16 or 17, wherein the liquid substance is applied with drops (56) arranged in a raster (R1-R4) and wherein the colourants (7) are bonded with several drops.
19. The method as in any one of the preceding embodiments, wherein the colourants (7) have a particle body (66) comprising fibres (61) or mineral material (63).
20. The method as in any one of the preceding embodiments, wherein the surface (2) with the bonded colourants (7) is pressed.
21. The method as in any one of the preceding embodiments, wherein the surface (2) with the bonded colourants (7) is heated and pressed.
22. The method as in any one of the preceding embodiments, wherein the surface (2) comprises another colour than the colourants (7).
23. The method as in any one of the preceding embodiments, wherein the method comprises additional steps of applying new colourants (7, 12*b*) with a different colour on the first bonded colourants (7, 12*a*) and on the surface (2), bonding a part of the new colourants (7, 12*b*) to the surface with a binder and removing non-bonded new colourants (7, 12*b*) from the surface such that a digital print (P) is formed with the first (12*a*) and the new (12*b*) colourants positioned side by side on the surface (2).
24. The method as in any one of the preceding embodiments, wherein the colourants (7) are applied by scattering.
25. The method as in any one of the preceding embodiments, wherein the colourants (7) are arranged in a wood grain or a stone pattern.
26. The method as in any one of the preceding embodiments, wherein the surface and the colourants are pressed and cured to a hard surface with an embossed (17) structure.
27. The method as in any one of the preceding embodiments, wherein the colourants (7) are macro colourant particles (64) larger than 20 microns.
28. The method as in any one of the preceding embodiments, wherein the colourants (7) are pressed into the surface (2).
29 The method as in any one of the preceding embodiments, wherein the surface (2) is a part of a panel (1) that is a laminate or wood floor, a powder based floor, a tile or a LVT floor.
30. An equipment (40) to provide a digital print (P) on a surface (2), comprising a digital drop application head (30'), a dry ink application station (27), and a dry ink removal station (28) wherein:
    the digital drop application head (30') is adapted to apply liquid blank ink (11) on the surface (2);
    the dry ink application station (27) is adapted to apply dry ink (15) comprising colourants (7) on the surface (2);
    the blank ink (11) is adapted to bond a part of the dry ink (15) to the surface (2); and
    the dry ink removal station (28) is adapted to remove the non-bonded colourants (7) from the surface (2).
31. An equipment as in embodiment 30, wherein the surface (2) is a part of a panel (1).
32. An equipment as in embodiments 30 or 31, wherein the dry ink (15) comprises a resin.
33. An equipment as in any one of the embodiments 30-32, wherein the blank ink (11) is water based.
34. An equipment as in any one of the embodiments 30-33, wherein the blank ink (11) is exposed to increased temperature after application.
35. Dry ink (15) comprising macro colourant particles (64) for bonding to a liquid print (P) applied on a surface (2) wherein the macro colourant particles (64) comprise a particle body (66) and colour pigments (12) attached to the particle body (66).
36. Dry ink as in embodiment 35, wherein the macro colourant particles (64) are larger than 20 microns.
37. Dry ink as in embodiments 35 or 36, wherein the particle body (66) is a mineral particle (63), a fibre (61) or a thermosetting resin (13).
38. Dry ink as in embodiments 35 or 36, wherein the particle body (66) is a mineral particle (63).
39. Dry ink as in embodiments 35 or 36, wherein, the particle body (66) is a fibre (61)
40. Dry ink as in any one of embodiments 35-39, wherein the particle body (66) is coated with a resin.
41. Dry ink as in embodiment 40, wherein the resin is a thermosetting resin (13).
42. Dry ink as in any one of embodiments 35-41, wherein the liquid print is water based and applied by a digital drop application head (30').
43. A panel (1) with a surface (2) comprising a digitally formed print (P) of macro colourants (64) comprising a particle body (66) and colour pigments (12) attached to the surface of the particle body (66) wherein the colourants (7) are arrange in patterns with pigments (12) on an upper and lower surface of the particle body (66).
44. A panel as in embodiment 43, wherein the particle body (66) comprises fibres (61).
45. A panel as in embodiment 43, wherein the particle body (66) is a mineral particle (63).
46. A panel as in any one of the embodiments 43-45, wherein the macro colourants (64) have a particle size exceeding 20 microns.
47. A panel as in any one of the preceding embodiments 43-46, wherein the macro courants (64) form a solid print with overlapping decorative particles.
48. A panel as in any one of the preceding embodiments 43-47, wherein the pane (1) is a laminate or wood floor, a powder based floor, a tile or a LVT floor.
49. A method of forming a digital embossing (17) on a surface (2) by bonding hard press particles (67) to a carrier (68) comprising the steps of:
    providing a liquid binder pattern (BP) on the carrier (68) by a digital drop application head (30') that applies a liquid substance (11) on the carrier;
    applying the hard press particles (67) on the carrier (68) and the binder pattern (BP) such that the hard press particles are bonded to the carrier (68) by the liquid binder pattern (BP);
    removing the non-bonded hard press particles (67) from the carrier (68);
    pressing the carrier (68) with the bonded hard press particles (67) to the surface (2); and
    removing the carrier (68) with the hard press particles (67) from the pressed surface (2).
50. The method as in embodiment 49, wherein the press particles (67) are mineral particles (63).
51. The method as in embodiments 49 or 50, wherein the carrier is a paper or a foil.
52. The method as in any one of the preceding embodiments 49-51, wherein the liquid substance is water based.

53. The method as in any one of the preceding embodiments 49-52, wherein the surface (2) is a powder or a paper or a foil.
54. The method as in any one of the preceding embodiments 49-53, wherein the surface (2) is a part of a panel (1).
55. A panel (1) having a surface (2) with a wood grain decor comprising a first surface portion (S1) that is formed by a continuous basic layer comprising wood fibres (61a) having a first colour and a second surface portion (S2) that is formed by wood fibres (61b) having a second colour wherein the wood fibres (61b) having the second colour are applied on and bonded to the continuous basic layer, and wherein the second surface portion (S2) covers a part of the first surface portion (S1).
56. The panel as in embodiment 55, wherein the continuous basic layer is a powder comprising a thermosetting resin
57. The panel as in embodiments 55 or 56, wherein the continuous basic layer is a paper.
58. The panel as in any one of the embodiments 55-57, wherein the second surface portion (S2) comprises smaller fibres than the first surface portion (S1)
59. An equipment to provide a digital print (P) on a surface (2) with a transfer printing method, wherein the equipment comprises a digital drop application head (30'), a dry ink application unit (27), a dry ink removal station (28) and a transfer surface (18) wherein:
    the digital drop application head (30') is adapted to apply liquid blank ink (11) on the transfer surface (18);
    the dry ink application unit (27) is adapted to apply dry ink (15) comprising colourants on the transfer surface (18);
    the blank ink (11) is adapted to bond a part of the dry ink (15) to the transfer surface (18);
    the dry ink removal station (28) is adapted to remove the non-bonded dry ink from the transfer surface (18); and
    the transfer surface (18) with the bonded dry ink is adapted to be pressed against the surface (2).
60. An equipment as in embodiment 59, wherein the dry ink (15) comprises a resin.
61. An equipment as in embodiments 59 or 60, wherein the blank ink (11) is water based.
62. An equipment as in any one of the embodiments 59-61, wherein the blank ink is exposed to increased temperature after application.
63. A press matrix (78) for forming an embossed structure (17) on a panel (1) wherein the press matrix comprises hard press particles (67) arranged in a pattern and bonded to a carrier (68) being a coated paper or a foil.
64. A press matrix (78) as in embodiment 63, wherein the hard press particles (67) are arranged on one side of the carrier and a print (P) is arranged on the opposite side of the carrier.
65. A press matrix (78) as in embodiments 63 or 64, wherein the hard press participles (67) and the print (P) are coordinated such that an in register embossed printed surface may be obtained when the press matrix is pressed against a panel surface (2).
66. A method of forming a digital print (P) on a surface (2) wherein the method comprises the steps of applying powder of dry ink (15) comprising colourants (7) on the surface, bonding a part of the dry ink (15) powder to the surface (2) by a digital heating print head (80) such that the digital print (P) is formed by the bonded dry ink colourants (7) and removing non bonded dry ink (15) from the surface (2).
67. The method as in embodiment 66, wherein the dry ink (15) comprises a heat sensitive resin.
68. The method as in embodiments 66 or 67, wherein the surface (2) comprises a heat sensitive resin.
69. The method as in embodiments 67 or 68, wherein the heat sensitive resin is a thermosetting or thermoplastic resin.
70. The method as in embodiment 69, wherein the heat sensitive resin is a thermosetting resin comprising melamine.
71. The method as in any one of the embodiments 66-69, wherein the heating print head (80) applies heat on a heat transfer foil (81).
72. The method as in embodiment 70, wherein the heat transfer foil (81) comprises copper or aluminium.
72. The method as in any one of the embodiments 66-68, wherein the surface (2) is a part of a building panel preferably a part of a floor panel (1).
73. The method as in any one of the embodiments 66-72, wherein the dry ink (15) comprises mineral particles.
74. The method as in embodiment 73, wherein the dry ink (15) comprises aluminium oxide particles.
75. A method of forming a digital print (P) on a surface (2) comprising applying drops (57) of blank ink (11) by a digital drop application head (30') on the surface (2) and attaching colourants (7) to the drops (57) of the blank ink for forming the digital print (P) wherein the digital print (P) comprises another colour than the blank ink (11).
76. The method as in embodiment 75, wherein the other colour is formed by colourants (7) bonded to the surface (2) by the blank ink (11).
77. The method as in embodiments 75 or 76, wherein the blank ink (11) is essentially a transparent liquid substance comprising water.
78. The method as in any one of the embodiments 75-77, wherein the blank ink (11) forms a first and a second part of the print (P) and wherein the blank ink, the first and the second parts all comprise different colours.
79. The method as in any one of the embodiments 75-78, wherein the digital print (P) comprises colourants (7) with different colours positioned horizontally offset in the same plane.
80. The method as in any one of the embodiments 75-79, wherein the vertical extension (V2) of the colourants (7) exceeds the vertical extension (V1) of blank ink drops (57).
81. The method as in any one of the embodiments 75-80, wherein the digitally applied blank ink drops (57) penetrate downwards and upwards from the surface (2) after application.
82. The method as in any one of the embodiments 75-81, wherein the drops of the blank ink (11) that provide a blank ink spot (57) on the surface (2) bonds colourants (7) having a size that is larger than the size of blank ink spot (57).
83. The method as in any one of the embodiments 75-82, wherein the blank ink (11) is applied in a raster pattern (R1-R4) and wherein the dry ink (15) is applied at random with overlapping colourants (7).
84. The method as in any one of the embodiments 75-83, wherein the horizontal extension (H2) of individual colourants (7) exceeds the horizontal extension (H1) of the ink spots (57) and the vertical extension (V2) of the dry ink layer, after the removal of the non-bonded particles, exceeds preferably the vertical extension (V1) of blank ink spots (57).

While illustrative embodiments of the invention have been described herein, the present invention is not limited to the various preferred embodiments described herein but includes any and all embodiments having equivalent elements, modifications, omissions, combinations (e.g. of aspects across various embodiments), adaptations and/or alterations as would be appreciated by those in the art based on the present disclosure. The limitations in the claims are to be interpreted broadly based on the language employed in the claims and not limited to the examples described in the present specification or during prosecution of the application, which examples are to be construed as non-exclusive.

The invention claimed is:

1. A method of forming a digital print on a surface of a building panel, wherein the method comprises:
   applying a liquid substance on the surface;
   applying mineral particles coated with a thermosetting resin on the liquid substance and the surface;
   bonding a part of the mineral particles to the surface with the liquid substance; and
   removing non-bonded mineral particles from the surface such that the digital print is formed by the bonded mineral particles.

2. The method as claimed in claim 1, wherein the mineral particles comprise aluminum oxide.

3. The method as claimed in claim 1, wherein the mineral particles comprise sand powder, stone powder, glass particles, glass powders or minerals derived from oxygen, silicon, aluminum, iron, magnesium, calcium, sodium or potassium.

4. The method as claimed in claim 1, wherein the mineral particles comprise color pigments.

5. The method as claimed in claim 4, wherein the color pigments are bonded to the mineral particles by the thermosetting resin.

6. The method as claimed in claim 4, wherein the color pigments are applied on an upper part and a lower part of the mineral particles.

7. The method as claimed in claim 4, wherein the mineral particles further comprise a content of thermosetting resin that is 10-30% and a pigment content that is 5-25% of the total weight of the mineral particles.

8. The method as claimed in claim 1, wherein the thermosetting resin is a melamine formaldehyde resin.

9. The method as claimed in claim 1, wherein the mineral particles are larger than 20 microns.

10. The method as claimed in claim 1, wherein the liquid substance comprises a binder.

11. The method as claimed in claim 1, wherein the liquid substance is water based.

12. The method as claimed in claim 1, wherein the liquid substance comprises ethylene glycol.

13. The method as claimed in claim 1, wherein the liquid substance is applied with a Piezo ink head.

14. The method as claimed in claim 1, wherein the liquid substance is applied as drops arranged in a raster.

15. The method as claimed in claim 1, the method further comprising permanently bonding said part of the mineral particles to the surface with heat and pressure after removing the non-bonded mineral particles.

16. The method as claimed in claim 1, wherein the surface of the building panel is a powder surface comprising wood fibers.

17. The method as claimed in claim 1, wherein the surface is part of a tile body comprising a basic glaze layer with a base color.

18. The method as claimed in claim 1, wherein the building panel is a floor panel, a furniture component, or a wall panel.

19. The method as claimed in claim 1, further comprising exposing the digital print to IR light, UV light, hot air, or microwave radiation.

* * * * *